(12) United States Patent
Lee et al.

(10) Patent No.: US 11,420,950 B2
(45) Date of Patent: Aug. 23, 2022

(54) HETEROCYCLICALKYL DERIVATIVE COMPOUNDS AS SELECTIVE HISTONE DEACETYLASE INHIBITORS AND PHARMACEUTICAL COMPOSITIONS COMPRISING THE SAME

(71) Applicant: Chong Kun Dang Pharmaceutical Corp., Seoul (KR)

(72) Inventors: Changsik Lee, Yongin-si (KR); Jaekwang Lee, Yongin-si (KR); Hyeseung Song, Yongin-si (KR); Daekwon Bae, Yongin-si (KR); Nina Ha, Yongin-si (KR); Hyang Kim, II, Yongin-si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 0 days.

(21) Appl. No.: 15/575,672

(22) PCT Filed: May 20, 2016

(86) PCT No.: PCT/KR2016/005411
§ 371 (c)(1),
(2) Date: Nov. 20, 2017

(87) PCT Pub. No.: WO2016/190630
PCT Pub. Date: Dec. 1, 2016

(65) Prior Publication Data
US 2018/0312482 A1 Nov. 1, 2018

(30) Foreign Application Priority Data
May 22, 2015 (KR) .......................... 10-2015-0071665

(51) Int. Cl.
*C07D 295/215* (2006.01)
*A61P 37/00* (2006.01)
(Continued)

(52) U.S. Cl.
CPC ............ *C07D 295/215* (2013.01); *A61P 9/00* (2018.01); *A61P 35/00* (2018.01); *A61P 37/00* (2018.01);
(Continued)

(58) Field of Classification Search
CPC ............. C07D 295/215; C07D 211/18; C07D 211/22; C07D 211/54; C07D 211/58;
(Continued)

(56) References Cited

U.S. PATENT DOCUMENTS

RE38,506 E    4/2004  Breslow et al.
7,250,514 B1  7/2007  Xiao
(Continued)

FOREIGN PATENT DOCUMENTS

EP    0 847 992        6/1998
JP    2001-523222 A    11/2001
(Continued)

OTHER PUBLICATIONS

Simone, Oncology: Introduction, Cecil Textbook of Medicine, 20th Edition, 1996 vol. 1, pp. 1004-1010. (Year: 1996).*
(Continued)

*Primary Examiner* — Savitha M Rao
*Assistant Examiner* — Andrew P Lee
(74) *Attorney, Agent, or Firm* — Crowell & Moring LLP; Yuezhong Feng

(57) ABSTRACT

The present invention relates to novel heterocyclicalkyl derivatives having histone deacetylase (HDAC) inhibitory activity, optical isomers thereof or pharmaceutically acceptable salts thereof, the use thereof for the preparation of
(Continued)

medicaments, pharmaceutical compositions containing the same, a method for treating diseases using the composition, and methods for preparing the novel heterocyclicalkyl derivatives. The novel heterocyclicalkyl derivatives according to the present invention are selective histone deacetylase (HDAC) inhibitors, and may be effectively used for the treatment of histone deacetylase-mediated diseases, such as cell proliferative diseases, inflammatory diseases, autosomal dominant diseases, genetic metabolic diseases, autoimmune diseases, acute/chronic neurological disease, hypertrophy, heart failure, ocular diseases, or neurodegenerative diseases.

6 Claims, 1 Drawing Sheet

(51) Int. Cl.
| A61P 9/00 | (2006.01) |
| A61P 35/00 | (2006.01) |
| C07D 241/04 | (2006.01) |
| C07D 471/10 | (2006.01) |
| C07D 211/18 | (2006.01) |
| C07D 211/22 | (2006.01) |
| C07D 211/58 | (2006.01) |
| C07D 211/62 | (2006.01) |
| C07D 213/36 | (2006.01) |
| C07D 295/205 | (2006.01) |
| C07D 211/96 | (2006.01) |
| C07D 211/54 | (2006.01) |

(52) U.S. Cl.
CPC .......... *C07D 211/18* (2013.01); *C07D 211/22* (2013.01); *C07D 211/54* (2013.01); *C07D 211/58* (2013.01); *C07D 211/62* (2013.01); *C07D 211/96* (2013.01); *C07D 213/36* (2013.01); *C07D 241/04* (2013.01); *C07D 295/205* (2013.01); *C07D 471/10* (2013.01)

(58) Field of Classification Search
CPC .. C07D 211/62; C07D 211/96; C07D 213/36; C07D 241/04; C07D 295/205; C07D 471/10; C07D 213/40; C07D 211/34; A61P 9/00; A61P 35/00; A61P 37/00; A61K 31/435; A61K 31/496; A61K 31/4965

See application file for complete search history.

(56) References Cited

U.S. PATENT DOCUMENTS

| 2002/0119962 A1 | 8/2002 | Jacobs et al. |
| 2005/0119305 A1 | 6/2005 | Naka et al. |
| 2007/0207950 A1 | 9/2007 | Yao et al. |
| 2008/0167287 A1 | 7/2008 | Zhuo et al. |
| 2008/0262073 A1 | 10/2008 | Cossio Mora et al. |
| 2010/0266531 A1 | 10/2010 | Hsieh et al. |
| 2011/0059118 A1 | 3/2011 | de Vicente Fidalgo |
| 2011/0300134 A1 | 12/2011 | van Duzer et al. |
| 2012/0015942 A1 | 1/2012 | Calderwood et al. |
| 2012/0015943 A1 | 1/2012 | Blackburn et al. |
| 2012/0028963 A1 | 2/2012 | Lee et al. |
| 2016/0083354 A1 | 3/2016 | Lee et al. |
| 2017/0096405 A1 | 4/2017 | Song et al. |

FOREIGN PATENT DOCUMENTS

| JP | 2005-527556 A | 9/2005 |
| JP | 2007-512367 A | 5/2007 |
| JP | 2009-509923 A | 3/2009 |
| JP | 2012-521982 A | 9/2012 |
| JP | 2013-518050 A | 5/2013 |
| JP | 2014-517831 A | 7/2014 |
| JP | 2016-524597 A | 8/2016 |
| WO | 01/44178 | 6/2001 |
| WO | 02/22577 | 3/2002 |
| WO | 02/30879 | 4/2002 |
| WO | WO0226696 A1 | 4/2002 |
| WO | 2002/72298 A1 | 9/2002 |
| WO | WO2003076395 A1 | 9/2003 |
| WO | WO2003082288 A1 | 10/2003 |
| WO | 2004/069823 | 8/2004 |
| WO | WO2007017728 A2 | 2/2007 |
| WO | 2007-022638 | 3/2007 |
| WO | WO2010085377 A2 | 7/2010 |
| WO | WO2010110545 A2 | 9/2010 |

OTHER PUBLICATIONS

Chondrex, A Protocol for Adjuvant-Induced Arthritis (AIA) in Rats, 2020, www.chondrex.com (Year: 2020).*
Zhang, Yingjie, et al., "Design, synthesis and primary activity assay of tripeptidomimetics as histone deacetylase inhibitors with linear linker and branched cap group"., European J. Med. Chem. 46: 5387-5397 (2011).
Strahl, Brian D., et al. "The language of covalent histone modifications", Nature, Jan. 6, 2000, p. 41-45, vol. 403.
Marks, Paul A., et al. "Histone deacetylases and cancer: cause and thereapies", Nature, Dec. 2001, p. 194-202, vol. 1.
Sonia, S., et al., Histone deacetylase inhibitors: apoptotic effects and clinical implications (Review), International Journal of Onocology, 2008, p. 637-646, vol. 33.
Marks, Paul A., et al. "Histone deacetylase inhibitors as new cancer drugs", Curr Opin. Oncol. 2001, p. 477-483, vol. 13.
Johnstone, R.W, "Histone-deacetylase inhibitors: Novel drugs for the treatment of cancer" Nat. Rev. Drug. Discov., 2002, p. 287-299, vol. 1.
Maiso, Patricia, et al.,"The histone-deacetylase inhibitor LBH589 is a potent antimyeloma agent that overcomes drug resistance", Cancer Res, Jun. 1, 2006, p. 5781-5789, vol. 66.
Subramanian, S., et al., "Clinical Toxicities of histone deacetylase inhibitors", Pharmaceuticals, 2010, p. 2751-2767, vol. 3.
Witt, Olaf et al., "HDAC family: What are the cancer relevant targets", Cancer Letters, 2009, p. 8-21, vol. 277.
Kovacs, J.J., et al. HDAC6 regulates Hsp90 acetylation and chaperone-depenent activation of clucocorticoid receptor, Mol. Cell, May 27, 2005, p. 601-607, vol. 18.
Santo, L., et al., "Preclinical activity, pharmacodynamic, and pharmacokinetic properties of a selective HDAC6 inhibitor, ACY-1215, in combination with bortezomib in multiple myeloma", Blood, Mar. 15, 2012, p. 2579-2589, vol. 119.
Vishwakarma, S., et al. "Tubastatin, a selective histone deacetylase 6 inhibitor shows anti-inflammatory and anti-rheumatic effects", International Immunopharmacology, 2013, p. 72-78, vol. 16.
Li, G., et al. "HDAC6 α-tubulin deacetylase: A potential therapeutic target in neurodegenerative diseases", Journal of the Neurological Sciences, 2011, p. 1-8, vol. 304.
Jung, M. et al., "Analogues of trichostatin a and trapoxin B as histone deacetylase inhibitors", Bioorganic & Medicinal Chemistry Letters, 1997, pp. 1655-1658, vol. 7, No. 13.
Yingxiu, Li et at., "Histone deacetylase 6 plays a role as a distinct regulator of diverse cellular processes" FEBS Journal, 2013, p. 775-793, vol. 280.
Seidel, C., et al., "Histone deacetylase 6 in health and disease", Epigenomics, 2015, p. 103-118, vol. 7, No. 1.
Wang, Z., et al., "Tubastatin A, an HDAC6 inhibitor, alleviates stroke-induced brain infarction and functional deficits: potential roles of α-tubulin acetylation and FGF-21 upregulation", Scientific Reports, 2016, p. 1-12, vol. 6:19626.
Zhang, Yu, et al., "Mice lacking histone deacetylase 6 have hyperacetylated tubulin but are viable and develop normally", Molecular and Cellular Biology, Mar. 2008, p. 1688-1701, vol. 28, No. 5.

(56) References Cited

OTHER PUBLICATIONS

Kee, H.J., et al. "HDAC Inhibition Suppresses Cardiac Hypertrophy and Fibrosis in DOCA-Salt Hypertensive Rats via Regulation of HDAC6/HDAC8 Enzyme Activity", Kidney Blood Press Res, 2013, p. 229-239, vol. 37.
Demos-Davies, K.M., et al. "HDAC6 contributes to pathological responses of heart and skeletal muscle to chronic angiotensinII signaling", Am J Physiol Heart Circ Physiol. Jul. 15, 2014; p. H252-H258, vol. 307, No. 2.
Zhang Y. et al., "Design, synthesis and primary activity assay of tripeptidomimetics as histone deacetylase inhibitors with linear linker and branched cap grou", European Journal of Medicinal Chemistry, 2011, vol. 46, pp. 5387-5397.
Yee, A. J. et al., "Ricolinostat (ACY-1215), the First Selective HDAC6 Inhibitor, in Combonation with Lenalidomide and Dexamethasone in Patients with Relapsed and Relapsed-and-Refractory Multiple Myeloma: Phase 1b Results (ACE-MM-101 Study)", Blood, 2015, 126:3055.
Juvale, D. C. et al. "3D-QSAR of histone deacetylase inhibitors: hydroxamate analogues", Org. Biomol. Chem., 2006, vol. 4, pp. 2858-2868.
Dai, Y. et al., "Indole Amide Hydroxamic Acids as Potent Inhibitors of Histone Deacetylases", Bioorg. Med. Chem. Lett. 2003, vol. 13, pp. 1897-1901.

\* cited by examiner

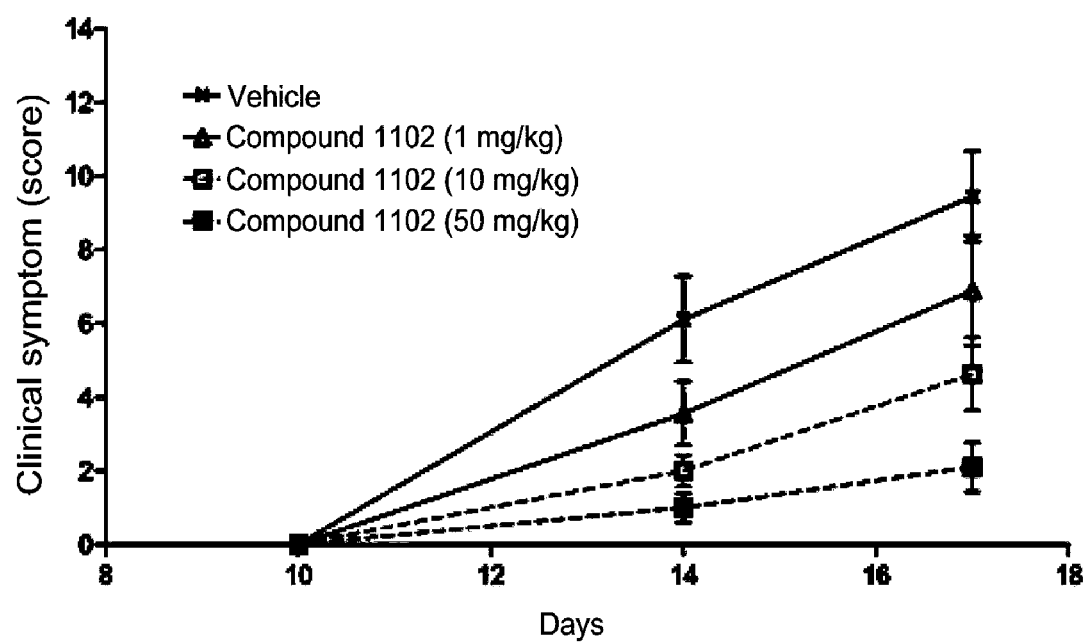

HETEROCYCLICALKYL DERIVATIVE COMPOUNDS AS SELECTIVE HISTONE DEACETYLASE INHIBITORS AND PHARMACEUTICAL COMPOSITIONS COMPRISING THE SAME

This application is a National Stage application of PCT International Application No. PCT/KR2016/005411 filed May 20, 2016. This application also claims priority under 35 U.S.C. § 119 to Korean Patent Application No. 10-2015-0071665, filed May 22, 2015.

TECHNICAL FIELD

The present invention relates to novel heterocyclicalkyl derivatives, and more particularly to novel heterocyclicalkyl derivatives having histone deacetylase (HDAC) inhibitory activity, optical isomers thereof or pharmaceutically acceptable salts thereof, the use thereof for the preparation of medicaments for treating HDAC-mediated diseases, pharmaceutical compositions containing the same, a method of treating diseases using the pharmaceutical compositions, and methods for preparing the novel heterocyclicalkyl derivatives.

BACKGROUND ART

Transcriptional regulation in cells is a complex biological process. One basic principle in transcriptional regulation is based on the posttranslational modification of histone proteins, namely histone proteins H2A/B, H3 and H4 forming the octameric histone core complex. The complex N-terminal modifications at lysine residues by acetylation or methylation and at serine residues by phosphorylation constitute part of the so called "histone code" (see Strahl & Ellis, Nature 403, 41-45, 2000).

In a simple model, acetylation of positively charged lysine residues decreases affinity to negatively charged DNA, thus transcription factors may be easily entered.

Histone acetylation and deacetylation is catalyzed by histone acetyltransferases (HATs) and histone deacetylases (HDACs), respectively. HDACs are associated with transcriptional repressor complexes, switching chromatin to a silence structure, transcriptionally inactive. (see Marks et al., Nature cancer Rev. 1, 189-202, 2001). The opposite is activated by HATs which are associated with transcriptional activator complexes. Three different classes of HDACs have been known so far, namely class I (HDAC 1-3, 8; Mr=42-55 kDa) primarily located in the nucleus and sensitive toward inhibition by Trichostatin A (TSA), class II (HDAC 4-7, 9, 10; Mr=120-130 kDa), which exhibits TSA sensitivity, and class III (SIRT1~7) that are distinct by their NAD+ dependency and TSA insensitivity.

Histone deacetylase (HDAC) inhibitors constitute a new class of anti-cancer drugs having cell differentiation and apoptosis inducing activity. By targeting histone deacetylases (HDACs), HDAC inhibitors affect Chromatin structure by histone acetylation, inducing reprogramming of a complex transcription, for example, reactivation of tumor suppressor genes and repression of oncogenes. Besides acetylate the N-terminal lysine residue in core histone protein, HDAC inhibitors target non-histone protein, important for cancer biology, including heat-shock-protein 90 (HSP90), tubulin or the p53 tumor suppressor protein. Thus, HDAC inhibitors may be used not only for anticancer therapy, but also for the treatment of genetic metabolic diseases, autoimmune diseases and the like, since efficacy in animal models for inflammatory diseases, rheumatoid arthritis and neurodegeneration has been shown.

Examples of histone deacetylase-mediated diseases associated with HDAC inhibition include cell proliferative diseases such as malignant tumor diseases, for example, cancers; inflammatory diseases such as inflammatory bowel diseases, Crohn's disease or ulcerative enteritis; autosomal dominant diseases such as Huntington's disease, Downs syndrome, Edwards syndrome or Pataus syndrome; genetic metabolic diseases such as diabetes, Niemann-Pick disease, Gaucher disease, phenylketonuria, Wilson's disease, or fibrosis diseases, for example, cystic fibrosis, hepatic fibrosis, kidney fibrosis, pulmonary fibrosis or skin fibrosis; autoimmune diseases such as rheumatoid arthritis, asthma, Lupus, psoriasis, psoriatic arthritis, multiple sclerosis, Beh's disease, or organ transplantation rejection; acute/chronic neurological diseases such as stroke or polycystic kidney disease; hypertrophy such as cardiac hypertrophy; heart failure such as congestive heart failure or hemorrhagic heart failure; ocular diseases such as glaucoma, dry eye syndrome, dry macular degeneration, wet macular degeneration, diabetic retinopathy, or uveitis; neurodegenerative diseases such as Alzheimer's disease, amyotrophic lateral sclerosis, Charcot Marie Tooth disease, or spinal muscular atrophy, as well as conditions and diseases caused by the abnormal function of HDAC enzymes.

HDAC inhibitors known up to now can be classified according to their structure into four categories: 1) short-chain fatty acids (butyric acid and valproic acid); 2) hydroxamic acids (trichostatin A, SAHA, and LBH-589); 3) cyclic peptides (desipeptide); and 4) benzamides (MS-275, and MGCD-0103) (Sonia et. al., International Journal of onocology 33,637-646, 2008). These many histone deacetylase (HDAC) inhibitors (SAHA, LBH-589 and MS-275 etc.) inhibit cell growth, and effectively induce cell differenciation and apoptosis of various transformed cells not only in culture media but also in animal models (Paul A. Marks et. al., Curr Opin. Oncol. 13,477-483, 2001). Therefore, HDAC inhibitors such as SAHA, LBH-589 and MS-275 have been assessed in clinical studies for the purpose of treating various cancers (Johnstone. R. W, Nat. Rev. Drug. Discov. 1, 287-299, 2002). Representative compounds, currently known as HDAC inhibitors, include SAHA (U.S. Reissue Pat. No. 385,069, Zolinza, Vorinostat), PXD101 (WO 02/30879, Belinostat) and LBH-589 (WO 02/22577, Panobinostat), which are hydroxamate compounds, and MS-275 (EP Patent No. 0847992 Entinostat) and MGCD0103 (WO 04/69823, Mocetinostat), which are benzamide compounds. Among these compounds, SAHA was approved on October 2006 and has been used as an agent for treating CTCL (cutaneous T-cell lymphoma), and indications thereof have been expanded additionally, but it is known that SAHA is insufficient in terms of efficacy and side effects (Paul A. Marks et al., Cancer Res 66, 5781-5789, 2006).

Various HDAC inhibitors are in preclinical or clinical development, but to date, only non-selective HDAC inhibitors have been identified as anticancer agents. Non-selective HDAC inhibitors are known to cause side effects such as fatigue and nausea, generally at high doses (Piekarz et al., Pharmaceuticals 2010, 3, 2751-2767). Such side effects have been reported to be due to the inhibition of class I HDACs. Due to such side effects, the use of non-selective HDAC inhibitors in the development of drugs other than anticancer drugs has been limited (Witt et al., Cancer Letters, 2009, 277, 8-21).

Meanwhile, it was reported that the selective inhibition of class II HDACs would not show toxicity shown in the inhibition of class I HDACs. Also, when selective HDAC inhibitors are developed, side effects such as toxicity, which are caused by the non-selective HDAC inhibition, can be overcome. Thus, selective HDAC inhibitors have potential to be developed as therapeutic agents effective for the treatment of various diseases (Matthias et al., Mol. Cell. Biol. 2008, 28, 1688-1701).

It is known that HDAC 6, a member of Class IIb HDACs, is present mainly in the cytoplasm and is involved in the deacetylation of a number of non-histone substrates (HSP90, cortactin, etc.), including tubulin (Yao et al., Mol. Cell 2005, 18, 601-607). Furthermore, HDAC 6 has two catalytic domains, and the C-terminal zinc finger domain thereof can bind to ubiquitinated proteins. It is known that HDAC 6 has a number of non-histone proteins as substrates, and thus plays an important role in various diseases, such as cancer, inflammatory diseases, autoimmune diseases, neurological diseases and neurodegenerative disorders (Santo et al., Blood 2012 119: 2579-258; Vishwakarma et al., International Immunopharmacology 2013, 16, 72-78; Hu et al., J. Neurol. Sci. 2011, 304, 1-8).

Accordingly, there is a need for the development of selective HDAC 6 inhibitors for treatment of cancer, inflammatory diseases, autoimmune diseases, neurological diseases and neurodegenerative disorders, which cause no side effects, unlike non-selective inhibitors.

DISCLOSURE OF INVENTION

Technical Problem

It is an object of the present invention to provide novel compounds having selective HDAC inhibitory activity, optical isomers thereof or pharmaceutically acceptable salts thereof.

Another object of the present invention is to provide pharmaceutical compositions containing novel compounds having highly selective HDAC inhibitory activity, optical isomers thereof or pharmaceutically acceptable salts thereof.

Still another object of the present invention is to provide methods for preparing the novel compounds.

Still another object of the present invention is to provide pharmaceutical compositions for treatment of HDAC activity-associated diseases, including cancer, inflammatory diseases, autoimmune diseases, neurological diseases or neurodegenerative disorders, which contain the above compounds.

Still another object of the present invention is to provide the use of the compounds for the preparation of medicaments for treating HDAC-mediated diseases, including cancer, inflammatory diseases, autoimmune diseases, neurological diseases or neurodegenerative disorders.

Yet another object of the present invention is to provide methods for treating HDAC-mediated diseases, including cancer, inflammatory diseases, autoimmune diseases, neurological diseases or neurodegenerative disorders, which comprise administering a therapeutically effective amount of the pharmaceutical compositions containing the compounds.

Solution to Problem

The inventors have found a novel compounds having HDAC inhibitory activity, and have used these compounds for inhibiting or treating histone deacetylase-mediated disease, thus completing the present invention.

Novel HDAC Inhibitors

To achieve the above objects, the present invention provides a compound of formula I below, an optical isomers thereof, or a pharmaceutically acceptable salts thereof.

[Formula I]

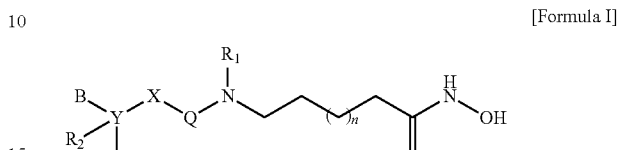

wherein

X is a heterocyclicalkyl selected from the group consisting of

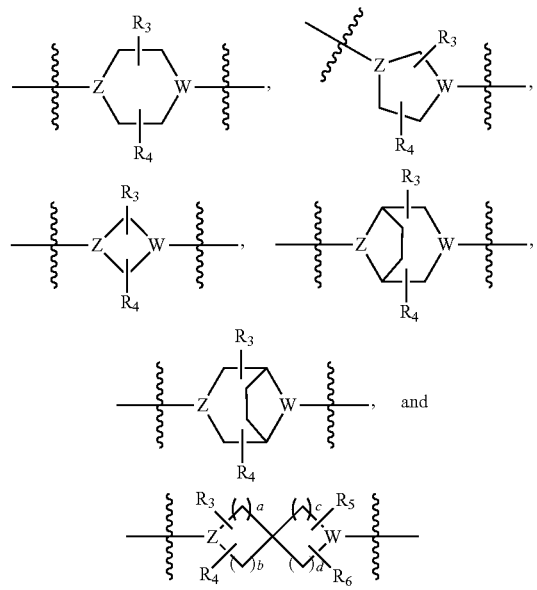

{wherein Z and W are each independently C or N, at least one of Z and W is N, a, b, c and d are each independently 1, 2 or 3, and $R_3$, $R_4$, $R_5$ and $R_6$ are each independently —H or —$C_1$-$C_4$ alkyl};

Y is C or N;

A and B are each independently —$C_1$-$C_4$alkyl, —$C_6$-$C_{10}$ aryl, —$C_3$-$C_{12}$ heteroaryl, —$C_3$-$C_{10}$ cycloalkyl, —$C_2$-$C_{10}$ heterocycloalkyl, or —$C_3$-$C_{10}$ cycloalkenyl {wherein one or more hydrogen atoms of the —$C_1$-$C_4$ alkyl may be substituted with —OH or halogen, and the —$C_6$-$C_{10}$ aryl, —$C_3$-$C_{12}$ heteroaryl, —$C_3$-$C_{10}$ cycloalkyl, —$C_2$-$C_{10}$ heterocycloalkyl and —$C_3$-$C_{10}$ cycloalkenyl may be each independently unsubstituted or substituted with —OH, —$C_1$-$C_4$ alkyl, —$OC_1$-$C_4$alkyl, —$CF_3$ or halogen at one or more hydrogen atoms thereof};

Q is C=O or $SO_2$;

$R_1$ is —H or —$C_1$-$C_4$ alkyl;

$R_2$ is —H, —OH, —$C_1$-$C_4$ alkyl, —$C_1$-$C_4$ alkylhydroxy, halogen or null {provided that when Y is C, $R_2$ is —H, —OH, —$C_1$-$C_4$alkyl or —$C_1$-$C_4$alkylhydroxy, and when Y is N, $R_2$ is null}; and n is 1, 2, 3 or 4.

According to one embodiment of the present invention, X is

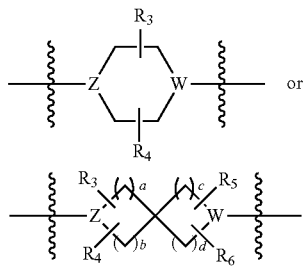

or

{wherein Z and W are each independently C or N, and at least one of Z and W is N, a, b, c and d are each independently 1, 2 or 3, and $R_3$, $R_4$, $R_5$ and $R_6$ are each independently —H or —$C_1$-$C_4$ alkyl};

Y is C or N;

A and B are each independently —$C_1$-$C_4$ alkyl, —$C_6$-$C_{10}$ aryl or —$C_3$-$C_{12}$ heteroaryl {wherein one or more hydrogen atoms of the —$C_1$-$C_4$ alkyl may be substituted with —OH or halogen, and the —$C_6$-$C_{10}$ aryl or —$C_3$-$C_{12}$ heteroaryl may be each independently unsubstituted or substituted with —OH, —$C_1$-$C_4$ alkyl, —$OC_1$-$C_4$alkyl, —$CF_3$ or halogen at one or more hydrogen atoms thereof};

Q is C=O or $SO_2$;

$R_1$ is —H or —$C_1$-$C_4$ alkyl;

$R_2$ is —H, —OH, halogen or null {provided that when Y is C, $R_2$ is —H, —OH or halogen, and when Y is N, $R_2$ is null}; and n is 1, 2, 3 or 4.

According to another embodiment of the present invention, X is

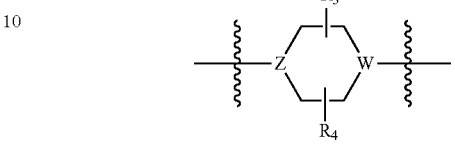

{wherein Z and W are each independently C or N, at least one of Z and W is N, and $R_3$ and $R_4$ are each independently —H or $C_1$-$C_4$ alkyl};

Y is C or N;

A and B are each independently —$C_1$-$C_4$ alkyl, —$C_6$-$C_{10}$ aryl or —$C_3$-$C_{12}$ heteroaryl {wherein one or more hydrogen atoms of the —$C_1$-$C_4$alkyl may be substituted with —OH or halogen, and the $C_6$-$C_{10}$ aryl and $C_3$-$C_{12}$ heteroaryl may be each independently unsubstituted or substituted with —OH, —$C_1$-$C_4$ alkyl, —$OC_1$-$C_4$ alkyl, —$CF_3$ or halogen at one or more hydrogen atoms thereof};

Q is C=O;

$R_1$ is —H or —$C_1$-$C_4$ alkyl;

$R_2$ is —H, —OH, halogen or null {provided that when Y is C, $R_2$ is —H, —OH or halogen, and when Y is N, $R_2$ is null}; and n is 3.

The compounds represented by formula I are shown in Tables 1 to 3 below:

TABLE 1

| Compound | Structure |
|---|---|
| 1102 | 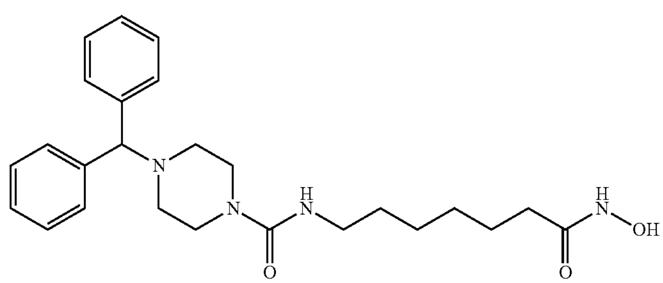 [SMILES: O=C(CCCCCCNC(=O)N1CCN(C(c2ccccc2)c2ccccc2)CC1)NO] |
| 1124 | 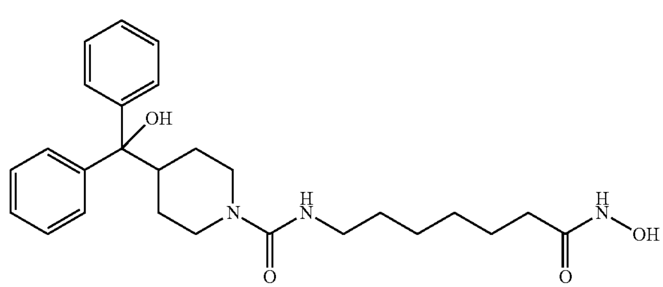 [SMILES: O=C(CCCCCCNC(=O)N1CCC(C(O)(c2ccccc2)c2ccccc2)CC1)NO] |

TABLE 1-continued

| Compound | Structure |
|---|---|
| 1188 | (2,6-dimethylpiperazine with N-benzhydryl and N-C(O)NH-(CH2)5-C(O)NHOH) |
| 1189 | (2-methylpiperazine with N-benzhydryl and N-C(O)NH-(CH2)5-C(O)NHOH) |
| 1190 | (2-methylpiperazine with N-benzhydryl and N-C(O)NH-(CH2)5-C(O)NHOH) |
| 1209 | (4-benzhydrylpiperidine-4-C(O)NH-(CH2)5-C(O)NHOH) |
| 1210 | (4-(hydroxydiphenylmethyl)piperidine-N-SO2-NH-(CH2)5-C(O)NHOH) |

TABLE 1-continued
| Compound | Structure |
|---|---|
| 1213 | 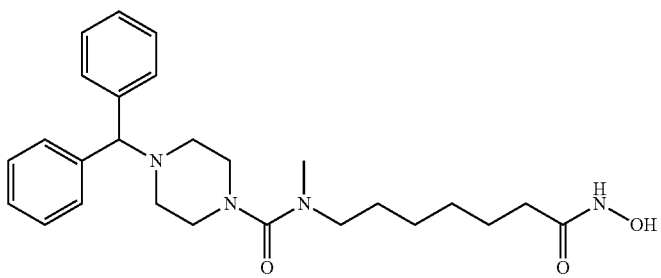 [SMILES: CN(CCCCCCC(=O)NO)C(=O)N1CCN(C(c2ccccc2)c2ccccc2)CC1] |
| 1221 | 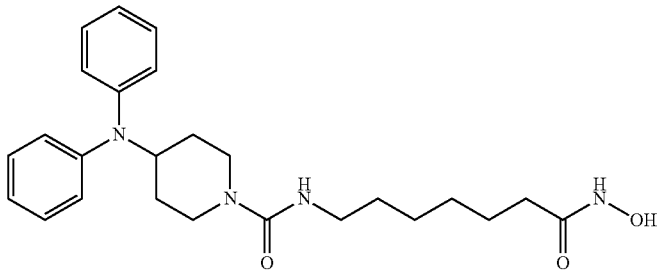 [SMILES: O=C(CCCCCCNC(=O)N1CCC(N(c2ccccc2)c2ccccc2)CC1)NO] |
| 1222 | 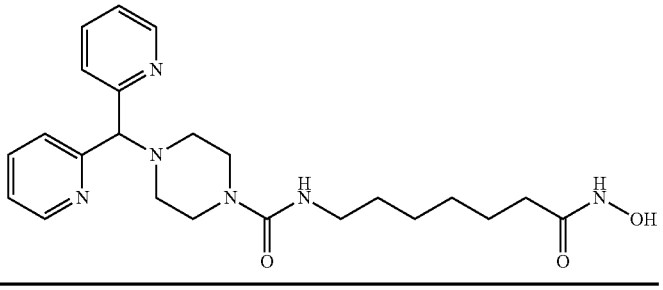 |
TABLE 2
| Compound | Structure |
|---|---|
| 1223 | 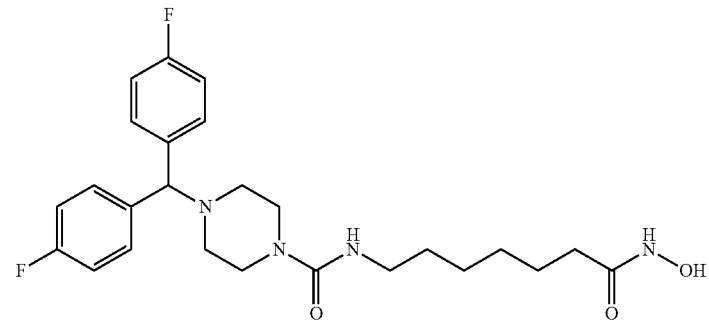 [SMILES: O=C(CCCCCCNC(=O)N1CCN(C(c2ccc(F)cc2)c2ccc(F)cc2)CC1)NO] |

TABLE 2-continued
| Compound | Structure |
|---|---|
| 1224 | 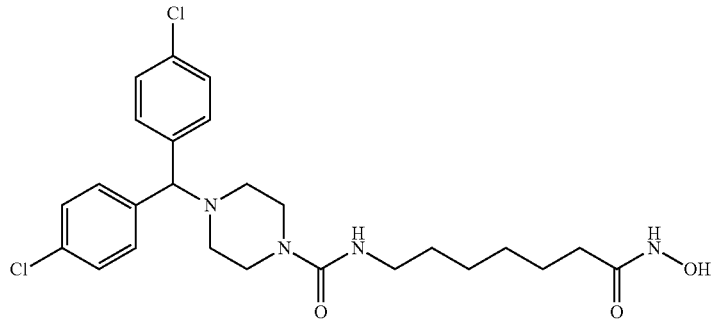 [SMILES: O=C(CCCCCCNC(=O)N1CCN(C(c2ccc(Cl)cc2)c2ccc(Cl)cc2)CC1)NO] |
| 1240 | 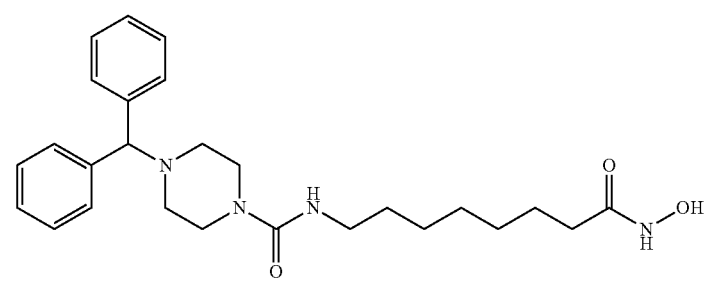 [SMILES: O=C(CCCCCCCNC(=O)N1CCN(C(c2ccccc2)c2ccccc2)CC1)NO] |
| 1241 | 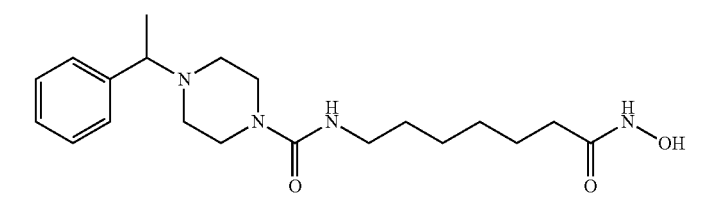 [SMILES: CC(c1ccccc1)N1CCN(C(=O)NCCCCCCC(=O)NO)CC1] |
| 1243 | 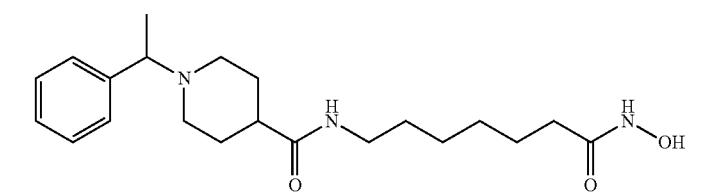 [SMILES: CC(c1ccccc1)N1CCC(C(=O)NCCCCCCC(=O)NO)CC1] |
| 1256 | 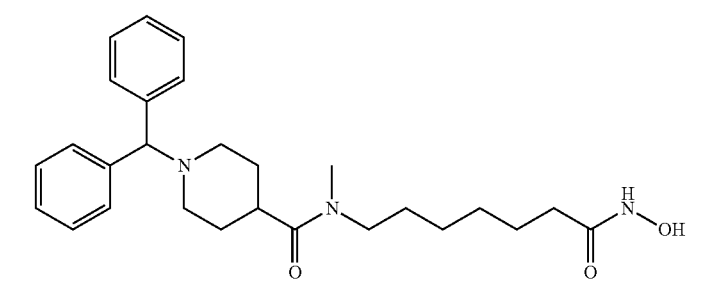 |
| 1257 | 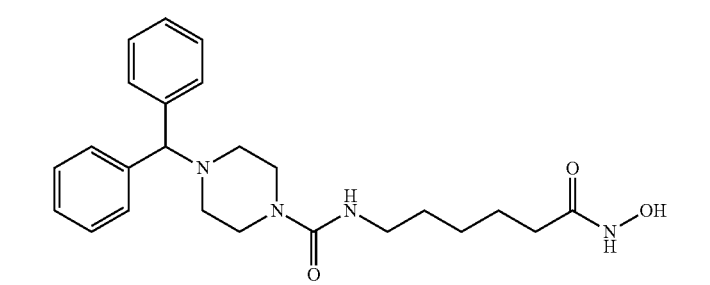 [SMILES: O=C(CCCCCNC(=O)N1CCN(C(c2ccccc2)c2ccccc2)CC1)NO] |

TABLE 2-continued

| Compound | Structure |
|---|---|
| 1316 | 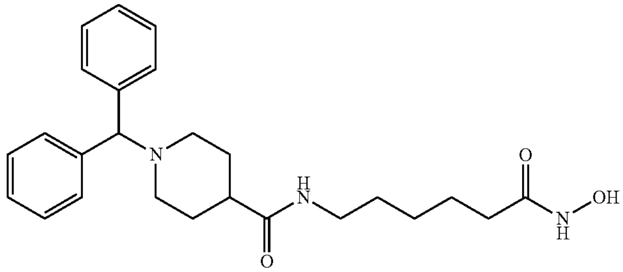 [SMILES: O=C(CCCCCNC(=O)C1CCN(C(c2ccccc2)c2ccccc2)CC1)NO] |
| 1317 | 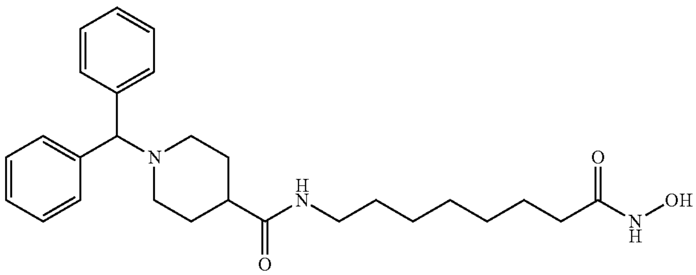 [SMILES: O=C(CCCCCCCNC(=O)C1CCN(C(c2ccccc2)c2ccccc2)CC1)NO] |
| 1647 | 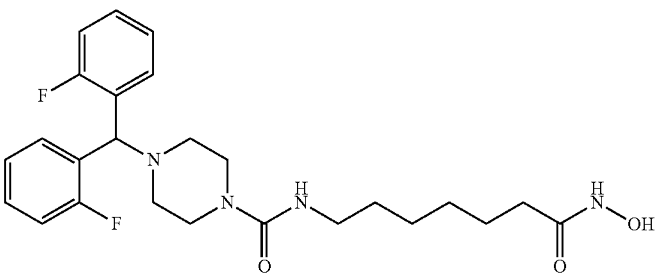 [SMILES: O=C(CCCCCCNC(=O)N1CCN(C(c2ccccc2F)c2ccccc2F)CC1)NO] |

TABLE 3

| Compound | Structure |
|---|---|
| 1648 | 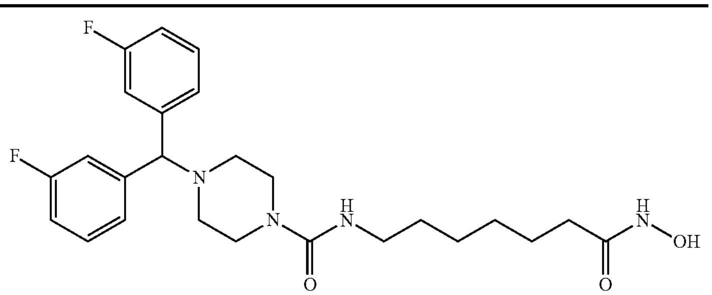 |
| 1649 | 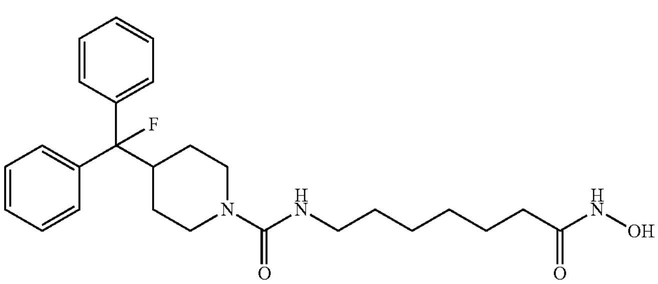 [SMILES: O=C(CCCCCCNC(=O)N1CCC(C(F)(c2ccccc2)c2ccccc2)CC1)NO] |

TABLE 3-continued
| Compound | Structure |
|---|---|
| 1719 | 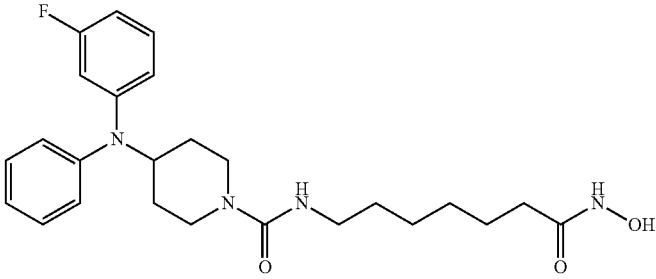 [SMILES: O=C(CCCCCCNC(=O)N1CCC(N(c2ccccc2)c2cccc(F)c2)CC1)NO] |
| 1726 | 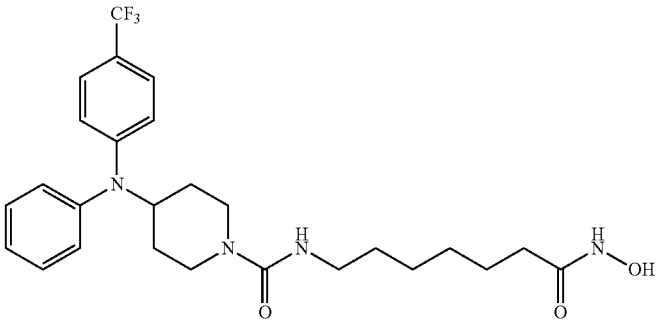 [SMILES: O=C(CCCCCCNC(=O)N1CCC(N(c2ccccc2)c2ccc(C(F)(F)F)cc2)CC1)NO] |
| 1734 | 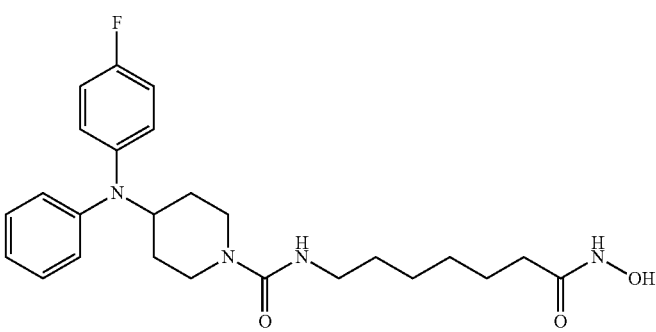 [SMILES: O=C(CCCCCCNC(=O)N1CCC(N(c2ccccc2)c2ccc(F)cc2)CC1)NO] |
| 1763 | 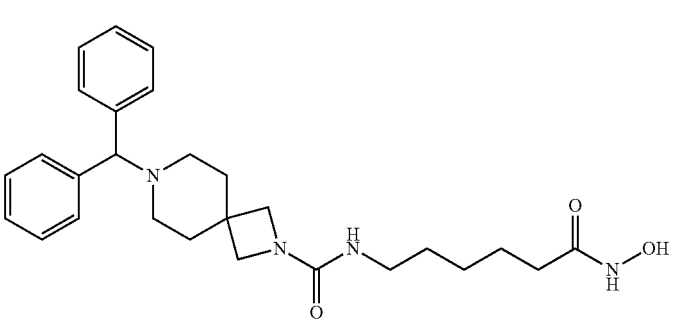 [SMILES: O=C(CCCCCNC(=O)N1CC2(CCN(C(c3ccccc3)c3ccccc3)CC2)C1)NO] |
| 1764 | 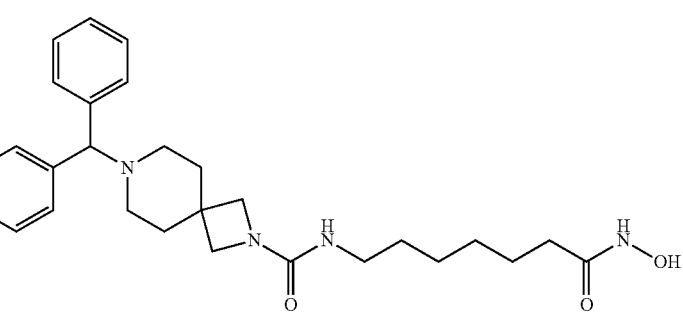 |

In the present invention, the compounds described in Tables 1 to 3 above or pharmaceutically acceptable salts thereof are preferably selected from the group consisting of compounds 1102, 1124, 1188, 1189, 1190, 1209, 1221, 1224, 1241 and 1243, and are more preferably selected from the group consisting of compounds 1102, 1124, 1188 and 1209.

As used herein, the term "pharmaceutically acceptable salt" means any salt that is generally used in the pharmaceutical field. Examples of the pharmaceutically acceptable salt include, but are not limited to, salts with inorganic ions such as calcium, potassium, sodium or magnesium ions, salts with inorganic acids such as hydrochloric acid, nitric acid, phosphoric acid, bromic acid, iodic acid, perchloric acid or sulfuric acid, salts with organic acids such as acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid or hydroiodic acid, salts with sulfonic acids such as methanesulfonic acid, ethane-sulfonic acid, benzenesulfonic acid, p-toluenesulfonic acid or naphthalenesulfonic acid, salts with amino acids such as glycine, arginine or lysine, and salts with amines such as trimethylamine, triethylamine, ammonia, pyridine or picoline.

The compounds of formula I may contain one or more asymmetrical carbon, and thus may exist in the form of racemates, racemic mixtures, single enantiomers, diastereomeric mixtures, and individual diastereomers. The compounds of formula I can be separated into such isomers by methods known in the art, for example, column chromatography or HPLC. Alternatively, individual stereoisomers of the compounds of formula I may be synthesized by stereospecific synthesis using optically pure starting materials and/or reagents of known configuration.

Composition comprising novel HDAC inhibiting compound, the use thereof and a method for treating disease using the same.

The present invention provides a pharmaceutical composition for preventing or treating a histone deacetylase-mediated disease, which contains, as an active ingredient, a compound represented by the following formula I, an optical isomer thereof or a pharmaceutically acceptable salt thereof.

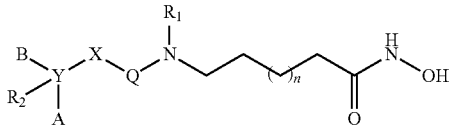

[Formula I]

wherein $R_1$, $R_2$, A, B, X, Y, Q and n are as defined above.

Examples of histone deacetylase-mediated diseases include cell proliferative diseases such as malignant tumor diseases, for example, cancers; inflammatory diseases such as inflammatory bowel diseases, Crohn's disease or ulcerative enteritis; autosomal dominant diseases such as Huntington's disease, Downs syndrome, Edwards syndrome or Pataus syndrome; genetic metabolic diseases such as diabetes, Niemann-Pick disease, Gaucher disease, phenylketonuria, Wilson's disease, or fibrosis diseases, for example, cystic fibrosis, hepatic fibrosis, kidney fibrosis, pulmonary fibrosis or skin fibrosis; autoimmune diseases such as rheumatoid arthritis, asthma, Lupus, psoriasis, psoriatic arthritis, multiple sclerosis, Beh's disease, or organ transplantation rejection; acute/chronic neurological diseases such as stroke, or polycystic kidney disease; hypertrophy such as cardiac hypertrophy; heart failure such as congestive heart failure or hemorrhagic heart failure; ocular diseases such as glaucoma, dry eye syndrome, dry macular degeneration, wet macular degeneration, diabetic retinopathy, or uveitis; neurodegenerative diseases such as Alzheimer's disease, amyotrophic lateral sclerosis, Charcot Marie Tooth disease, or spinal muscular atrophy, as well as conditions and diseases caused by the abnormal function of HDAC enzymes.

The pharmaceutically acceptable salt is as described above with respect to a pharmaceutically acceptable salt of the compound represented by formula I according to the present invention.

For administration, the pharmaceutical composition according to the present invention may further contain at least one pharmaceutically acceptable carrier in addition to the compound of formula I, an isomer thereof or a pharmaceutically acceptable salt thereof. The pharmaceutically acceptable carrier that is used in the present invention may be at least one of physiological saline, sterile water, Ringer solution, buffered saline, dextrose solution, maltodextrin solution, glycerol, ethanol, and a mixture of two or more thereof. If necessary, the composition may contain other conventional additives such as an antioxidant, a buffer or a bacteriostatic agent. In addition, the composition can be formulated into injectable formulations such as solutions, suspensions, turbid fluid, etc., pills, capsules, granules or tablets using a diluent, a dispersing agent, a surfactant, a binder and a lubricant. Thus, the composition of the present invention may be in the form of patches, liquids, pills, capsules, granules, tablets, suppositories, etc. These formulations can be prepared either by conventional methods that are used for formulation in the art or by the method disclosed in Remington's Pharmaceutical Science (the latest edition), Mack Publishing Company, Easton Pa.

The pharmaceutical composition of the present invention may be administered orally or parenterally (e.g., intravenously, subcutaneously, intraperitoneally or topically) depending on the intended use. The dose of the pharmaceutical composition varies depending on the patient's weight, age, sex, health conditions and diet, the time of administration, the mode of administration, excretion rate, the severity of the disease, and the like. The daily dose of the compound of formula I according to the present invention may be about 1 to 500 mg/kg, preferably 5 to 100 mg/kg, and may be administered once to several times a day.

The pharmaceutical composition of the present invention may further contain, in addition to the compound represented by formula I, an optical isomer thereof or a pharmaceutically acceptable salt thereof, one or more active ingredients that exhibit medicinal efficacy identical or similar thereto.

The present invention also provides a method for preventing or treating a histone deacetylase-mediated disease, which comprises administering a therapeutically effective amount of the compound represented by formula I, an optical isomer thereof or a pharmaceutically acceptable salt thereof.

As used herein, the term "therapeutically effective amount" refers to the amount of the compound represented by formula I, which is effective for the prevention or treatment of histone deacetylase mediated diseases.

The present invention also provides a method for inhibiting histone deacetylase (HDAC), by administering the compound represented by formula I, an optical isomer thereof or a pharmaceutically acceptable salt thereof to mammals including humans.

The method for preventing or treating histone deacetylase madiated disease according to the present invention includes inhibiting or averting the disease, as well as addressing the disease itself, prior to the onset of symptoms by administering the compound represented by formula I. In the management of diseases, a prophylactic or therapeutic dose of a particular active ingredient will vary with the nature and severity of the disease or condition, and may also vary according to the route by which the active ingredient is administered. The dose and the dose frequency will also vary according to the age, body weight, and response of the individual patient. Suitable dosing regimens can be readily selected by those skilled in the art with due consideration of such factors. In addition, the method for preventing or treating histone deacetylase mediated disease according to the present invention may further comprise administering a therapeutically effective amount of an additional active agent helpful for the treatment of the disease together with the compound represented by formula I, in which the additional active agent can exhibit a synergistic or assistant effect with the compound of formula I.

The present invention is also intended to provide the use of the compound represented by formula I, an optical isomer thereof or a pharmaceutically acceptable salt thereof, for the preparation of a medicament for treating histone deacetylase mediated disease. For the preparation of the medicament, the compound represented by formula I may be mixed with a pharmaceutically acceptable adjuvant, diluent, carrier or the like, and combined with other active agents such that the active ingredients can have synergistic effects.

The particulars mentioned in the use, composition and treatment method of the present invention may be appropriately combined unless contradictory to one another.

Methods for Preparing Novel HDAC Inhibitor Compounds

The present invention also provides methods for preparing the compounds represented by formula I, optical isomers thereof or pharmaceutically acceptable salts thereof. These preparation methods will now be described with reference to the following reaction schemes 1 to 10.

[Reaction scheme 1]

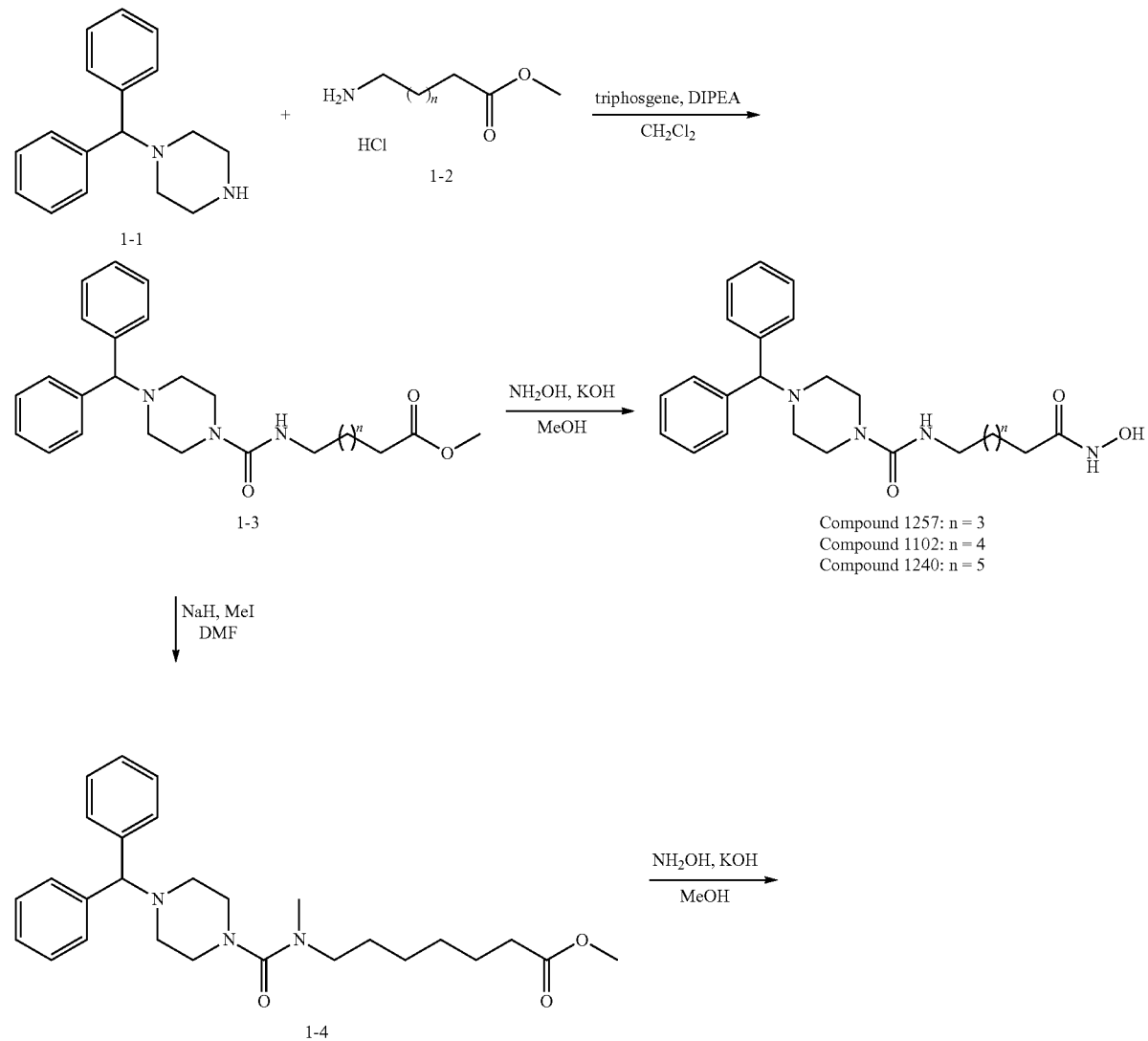

-continued

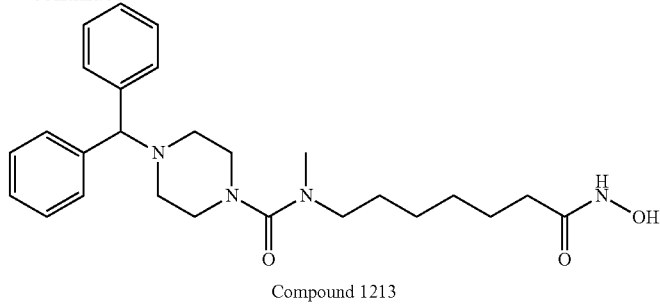

Compound 1213

As shown in reaction scheme 1 above, a compound of formula 1-1 is subjected to a urea forming reaction with methyl 6-aminohexanoate hydrochloride, methyl 7-aminoheptanoate hydrochloride or methyl 8-aminoctanoate hydrochloride (formula 1-2) to synthesize a compound of formula 1-3. Potassium hydroxide (KOH), methanol and aqueous hydroxylamine solution are added to the compound of formula 1-3 and reacted at room temperature, thereby synthesizing final compounds 1102, 1240 and 1257.

In addition, the compound of formula 1-3, which has methyl 7-aminoheptanoate introduced therein, is reacted with iodomethane to synthesize a compound of formula 1-4. Potassium hydroxide (KOH), methanol and aqueous hydroxylamine solution are added to the compound of formula 1-4 and reacted at room temperature, thereby synthesizing final compound 1213.

[Reaction scheme 2]

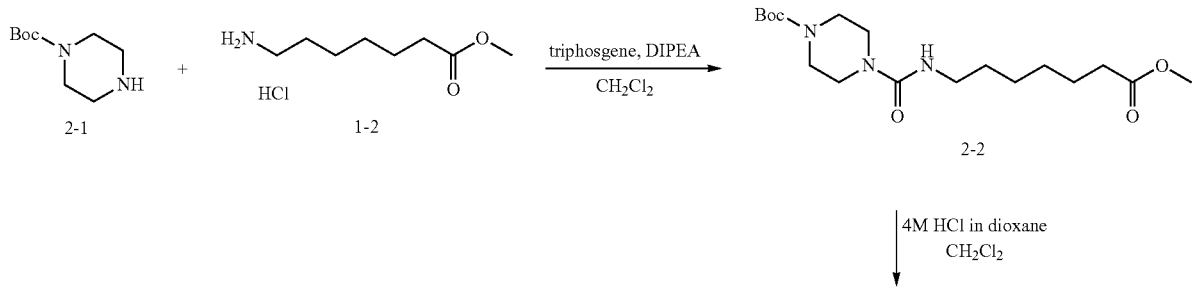

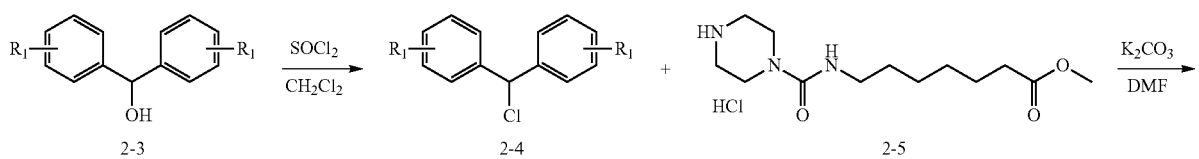

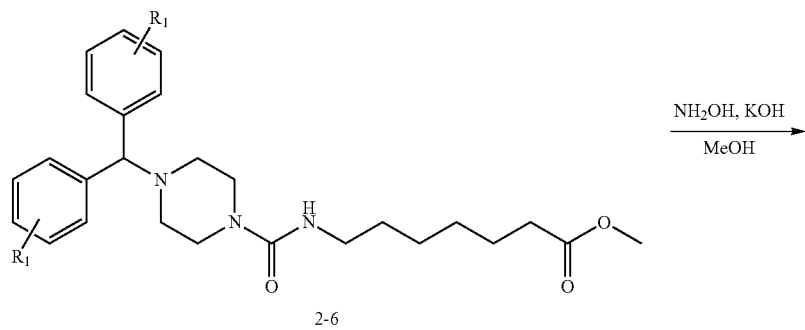

-continued

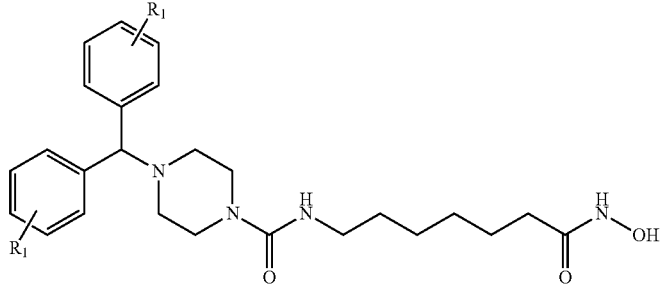

Compound 1223; R₁ = p-F
Compound 1224; R₁ = p-Cl
Compound 1647; R₁ = o-F
Compound 1648; R₁ = m-F As shown in reaction scheme 2 above, a compound of formula 2-1 is subjected to a urea forming reaction with methyl 7-aminoheptanoate hydrochloride (formula 1-2) to synthesize a compound of formula 2-2, which is then reacted with 4 M hydrochloric acid solution to remove the amino protecting group (Boc), thereby synthesizing a compound of formula 2-5. A compound of formula 2-3 is reacted with thionyl chloride to synthesize a compound of formula 2-4, which is then subjected to a substitution reaction with the compound of formula 2-5 to synthesize a compound of formula 2-6. Potassium hydroxide (KOH), methanol and aqueous hydroxylamine solution are added to the compound of formula 2-6 and reacted at room temperature, thereby synthesizing final compounds 1223, 1224, 1647 and 1648.

[Reaction scheme 3]

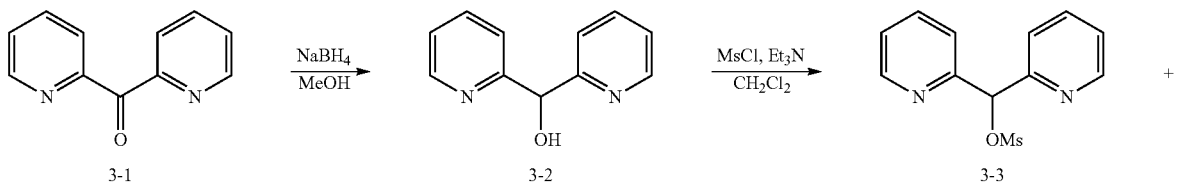

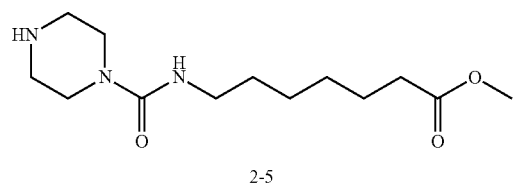

2-5

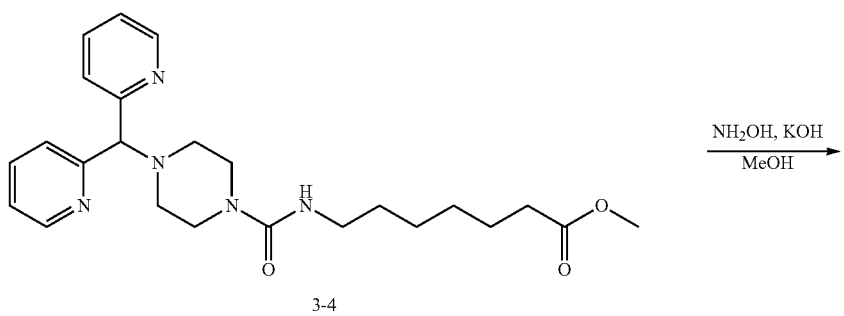

3-4

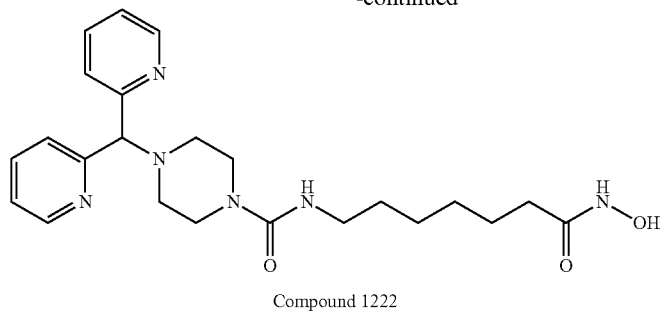

Compound 1222

As shown in reaction scheme 3 above, a compound of formula 3-1 is reduced with sodium borohydride to synthesize a compound of formula 3-2, which is then reacted with methanesulfonyl chloride to synthesize a compound of formula 3-3. The compound of formula 3-3 is subjected to a substitution reaction with a compound of formula 2-5 to synthesize a compound of formula 3-4. Then, potassium hydroxide (KOH), methanol and aqueous hydroxylamine solution are added to the compound of formula 3-4 and reacted at room temperature, thereby synthesizing final compound 1222.

[Reaction Scheme 4]

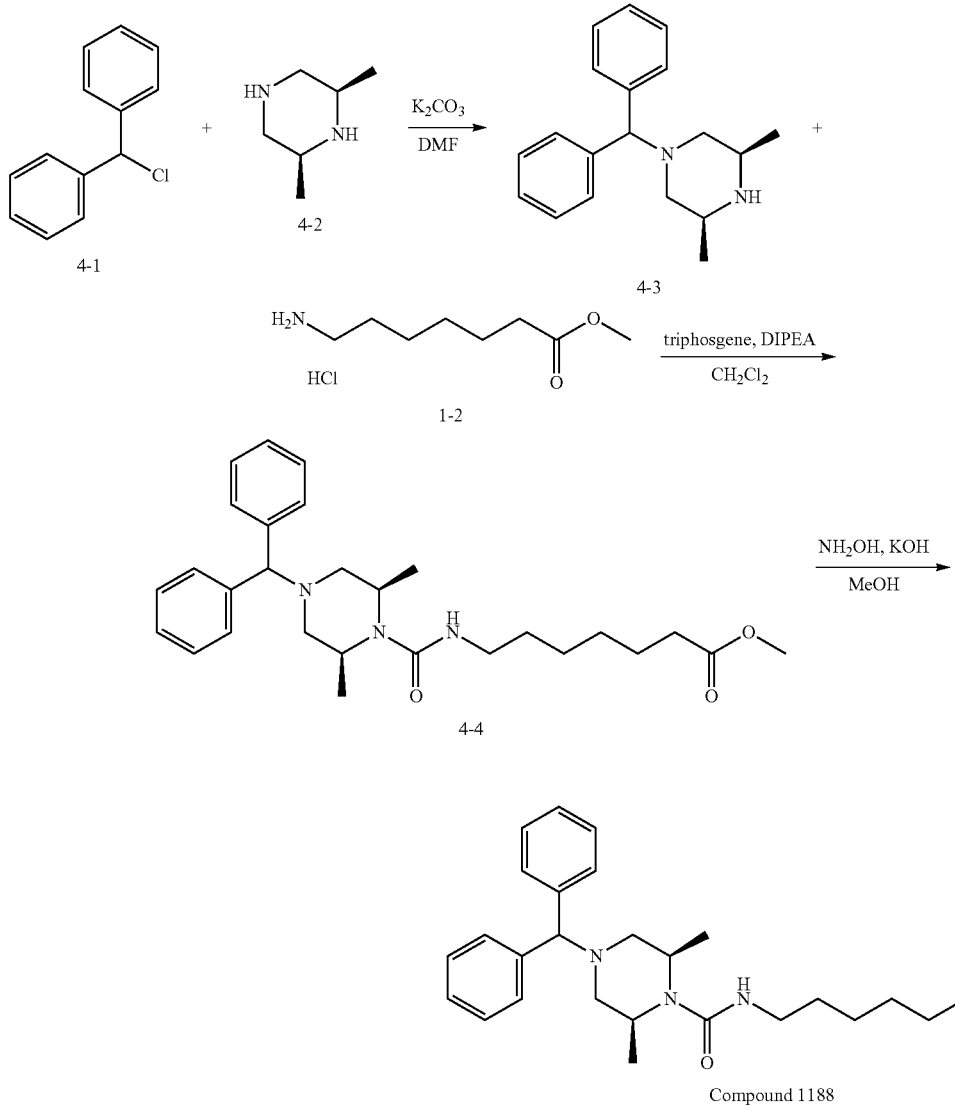

Compound 1188

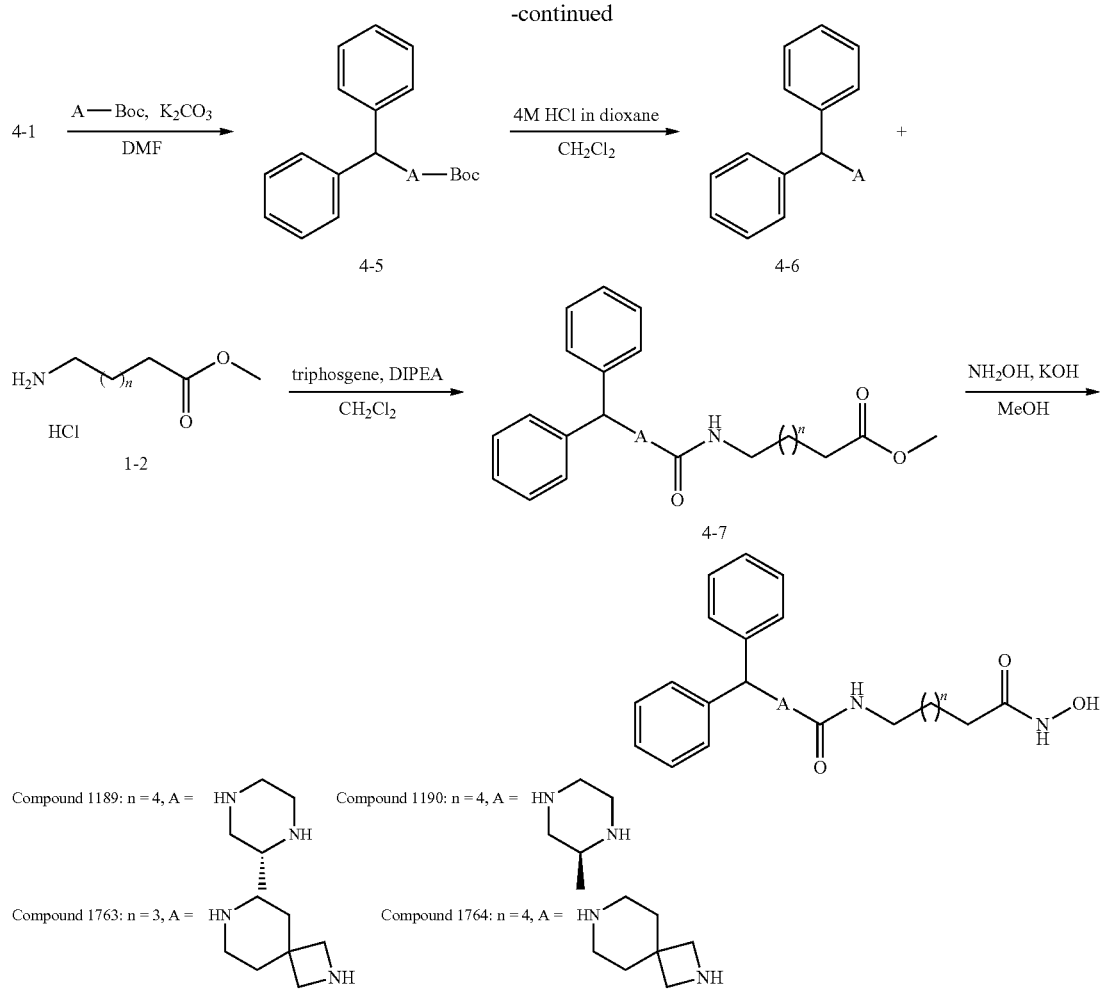

As shown in reaction scheme 4 above, a compound of formula 4-1 is subjected to a substitution reaction with (2S,6R)-2,6-dimethylpiperazine (formula 4-2) to synthesize a compound of formula 4-3, which is then subjected to a urea forming reaction with methyl 7-aminoheptanoate hydrochloride to synthesize a compound of formula 4-4. Then, potassium hydroxide (KOH), methanol and aqueous hydroxylamine solution are added to the compound of formula 4-4 and reacted at room temperature, thereby synthesizing final compound 1188.

In addition, the compound of formula 4-1 is reacted with an A-Boc compound, and then treated with 4 M hydrochloric acid solution to remove the protecting group (Boc), thereby synthesizing a compound of formula 4-6. The compound of formula 4-6 is subjected to a urea forming reaction with a compound of formula 1-2 to synthesize a compound of formula 4-7. Then, potassium hydroxide (KOH), methanol and aqueous hydroxylamine solution are added to the compound of formula 4-7 and reacted at room temperature, thereby synthesizing final compounds 1189, 1190, 1763 and 1764.

[Reaction scheme 5]

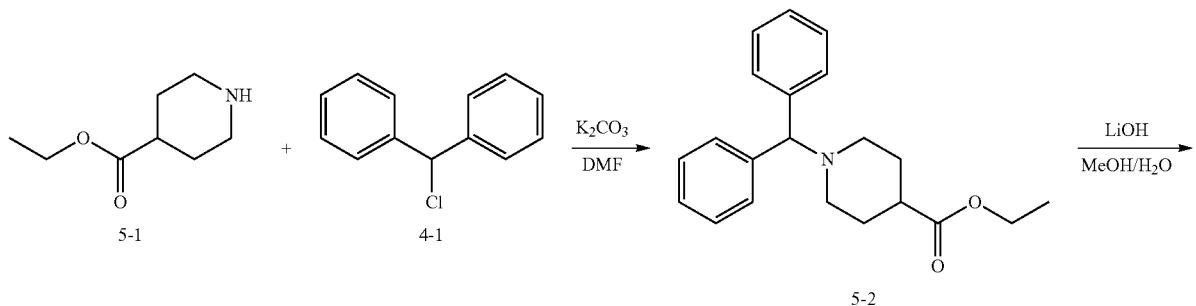

-continued

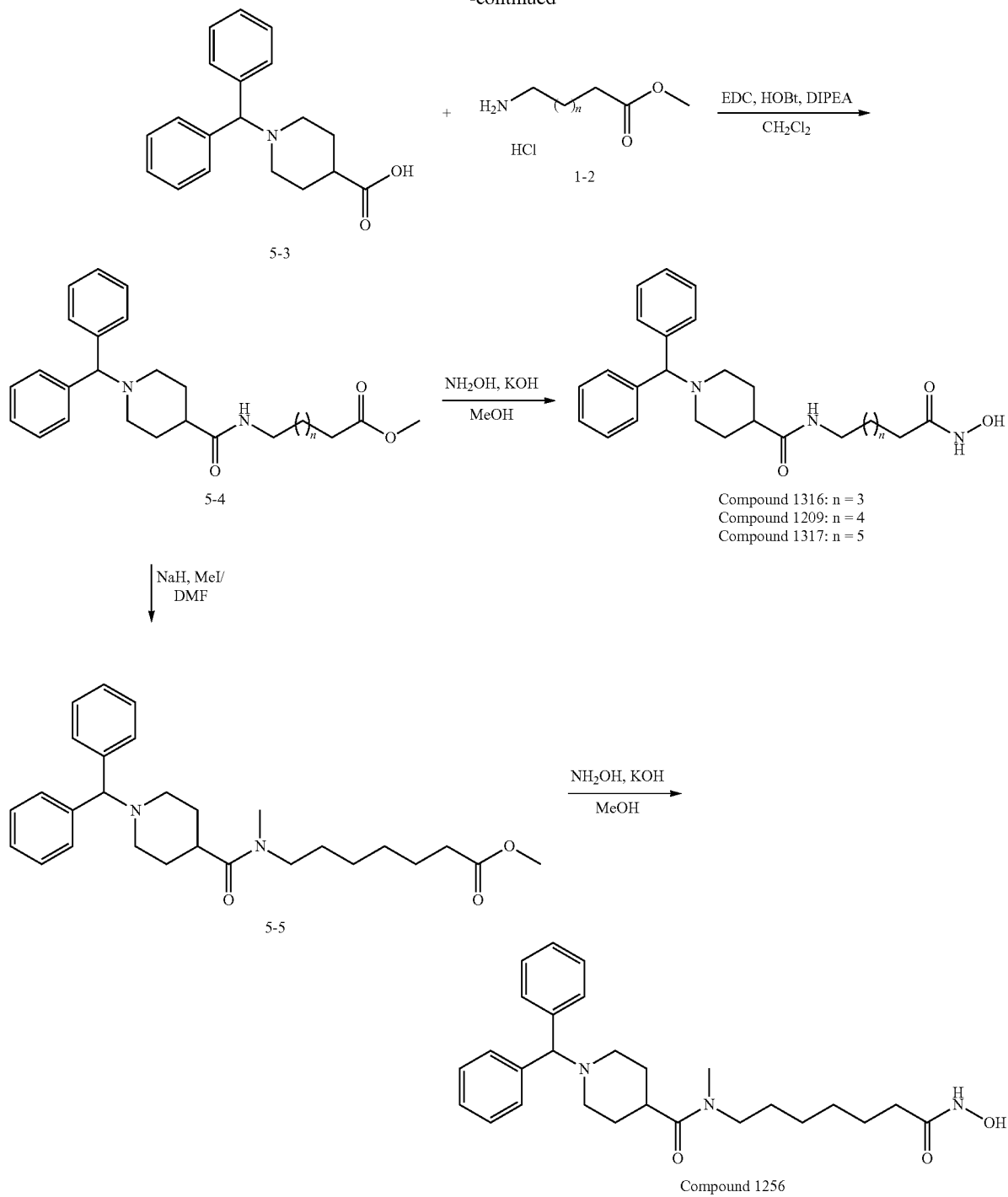

As shown in reaction scheme 5, a compound of formula 5-1 is subjected to a substitution reaction with (chloromethylene)dibenzene (formula 4-1) to synthesize a compound of formula 5-2, which is then hydrolyzed with lithium hydroxide (LiOH) to synthesize a compound of formula 5-3. The compound of formula 5-3 is subjected to amide coupling with methyl 6-aminohexanoate hydrochloride, methyl 7-aminoheptanoate hydrochloride or methyl 8-aminoctanoate hydrochloride to synthesize a compound of formula 5-4. Then, potassium hydroxide (KOH), methanol and aqueous hydroxylamine solution are added to the compound of formula 5-4 and reacted at room temperature, thereby synthesizing final compounds 1209, 1316 and 1317.

In addition, the compound of formula 5-4, which has methyl 7-aminoheptanoate introduced therein, is reacted with iodomethane to synthesize a compound of formula 5-5. Then, potassium hydroxide (KOH), methanol and aqueous hydroxylamine solution are added to the compound of formula 5-5 and reacted at room temperature, thereby synthesizing final compound 1256.

[Reaction scheme 6]

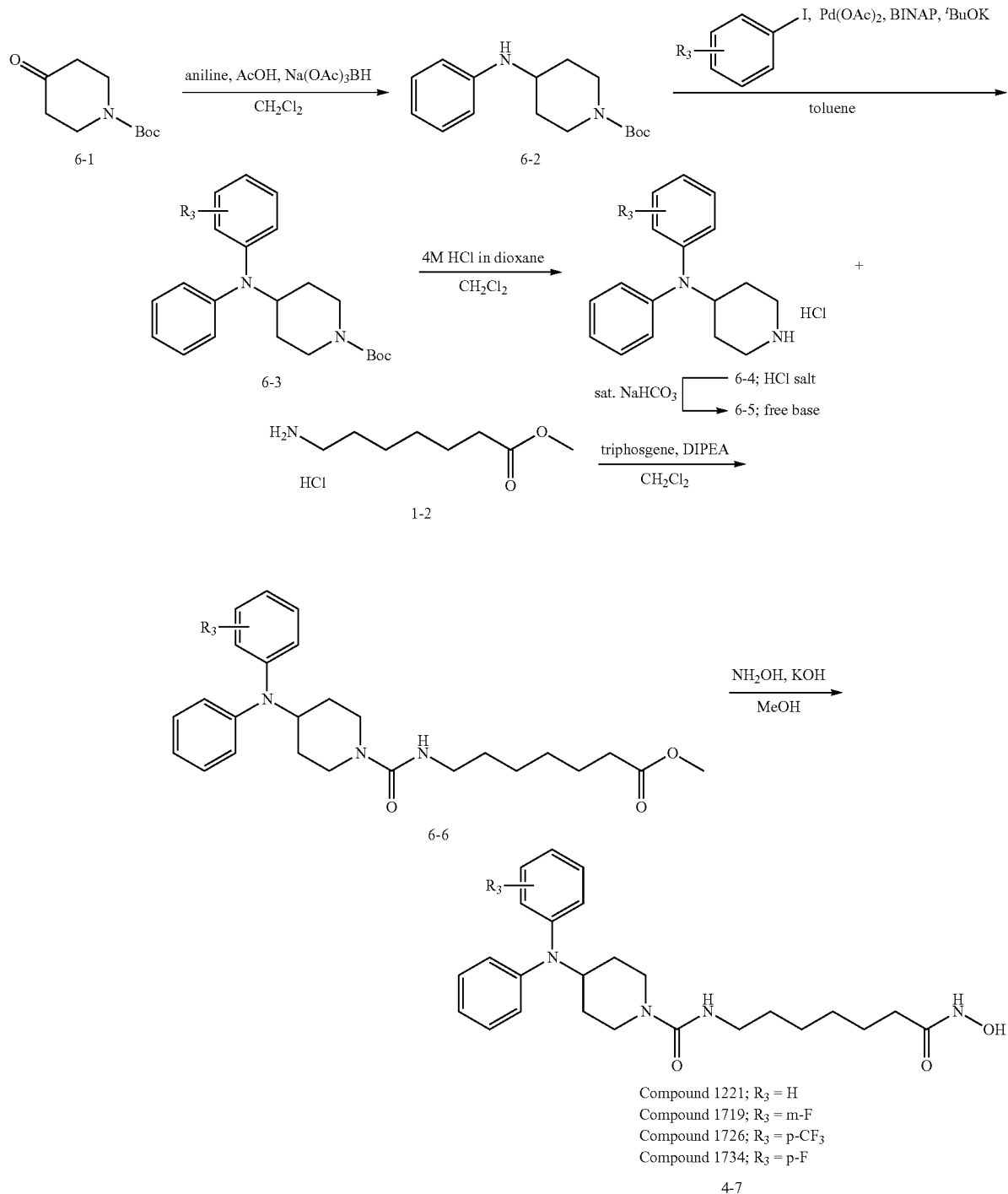

Compound 1221; R$_3$ = H
Compound 1719; R$_3$ = m-F
Compound 1726; R$_3$ = p-CF$_3$
Compound 1734; R$_3$ = p-F 4-7

As shown in reaction scheme 6 above, a compound of formula 6-1 is subjected to reductive amination with aniline to synthesize a compound of formula 6-2, which is then subjected to a Buckwald reaction to synthesize a compound of formula 6-3. The compound of formula 6-3 is reacted with 4 M hydrochloric acid solution to remove the amino protecting group (Boc), and then reacted with a saturated sodium bicarbonate solution to synthesize a compound of formula 6-5. The compound of formula 6-5 is subjected to a urea forming reaction with methyl 7-aminoheptanoate hydrochloride (formula 1-2) to synthesize a compound of formula 6-6. Then, potassium hydroxide (KOH), methanol and aqueous hydroxylamine solution are added to the compound of formula 6-6 and reacted at room temperature, thereby synthesizing final compounds 1221, 1719, 1726 and 1734.

[Reaction scheme 7]
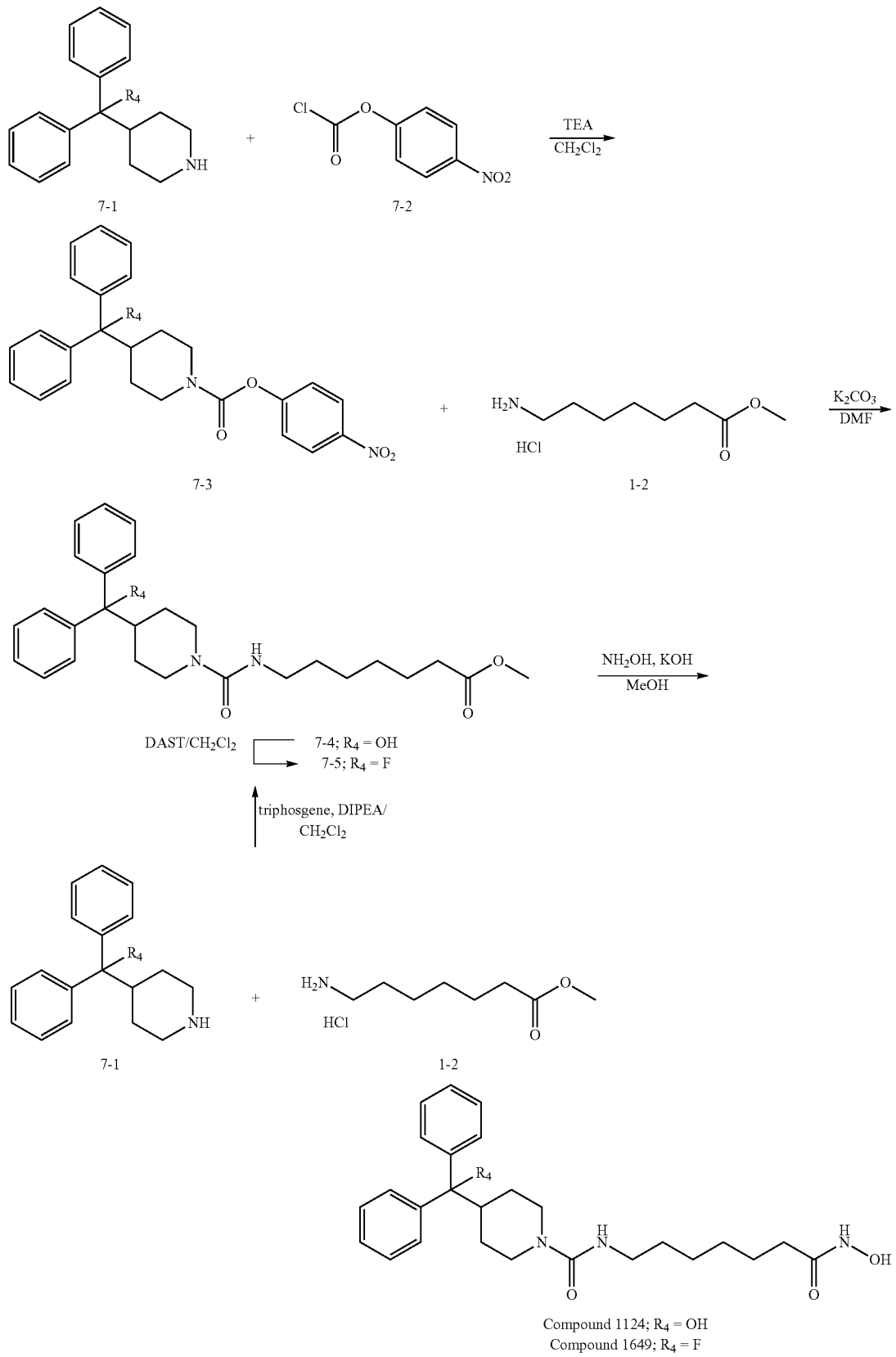
Compound 1124; R₄ = OH
Compound 1649; R₄ = F

As shown in reaction scheme 7, a compound of formula 7-1 is reacted with 4-nitrophenyl carbonochloridate (formula 7-2) to synthesize a compound of formula 7-3, which is then subjected to a substitution reaction with methyl 7-aminoheptanoate hydrochloride (formula 1-2) to synthesize a compound of formula 7-4. Then, potassium hydroxide (KOH), methanol and aqueous hydroxylamine solution are added to the compound of formula 7-4 and reacted at room temperature, thereby synthesizing final compound 1124.

In addition, the compound of formula 7-1 is subjected to a urea forming reaction with methyl 7-aminoheptanoate hydrochloride (formula 1-2) to synthesize a compound of formula 7-4, which is then reacted with diethylaminosulfur trifluoride (DAST) to synthesize a compound of formula 7-5. Then, potassium hydroxide (KOH), methanol and aqueous hydroxylamine solution are added to the compound of formula 7-5 and reacted at room temperature, thereby synthesizing final compound 1649.

[Reaction scheme 8]

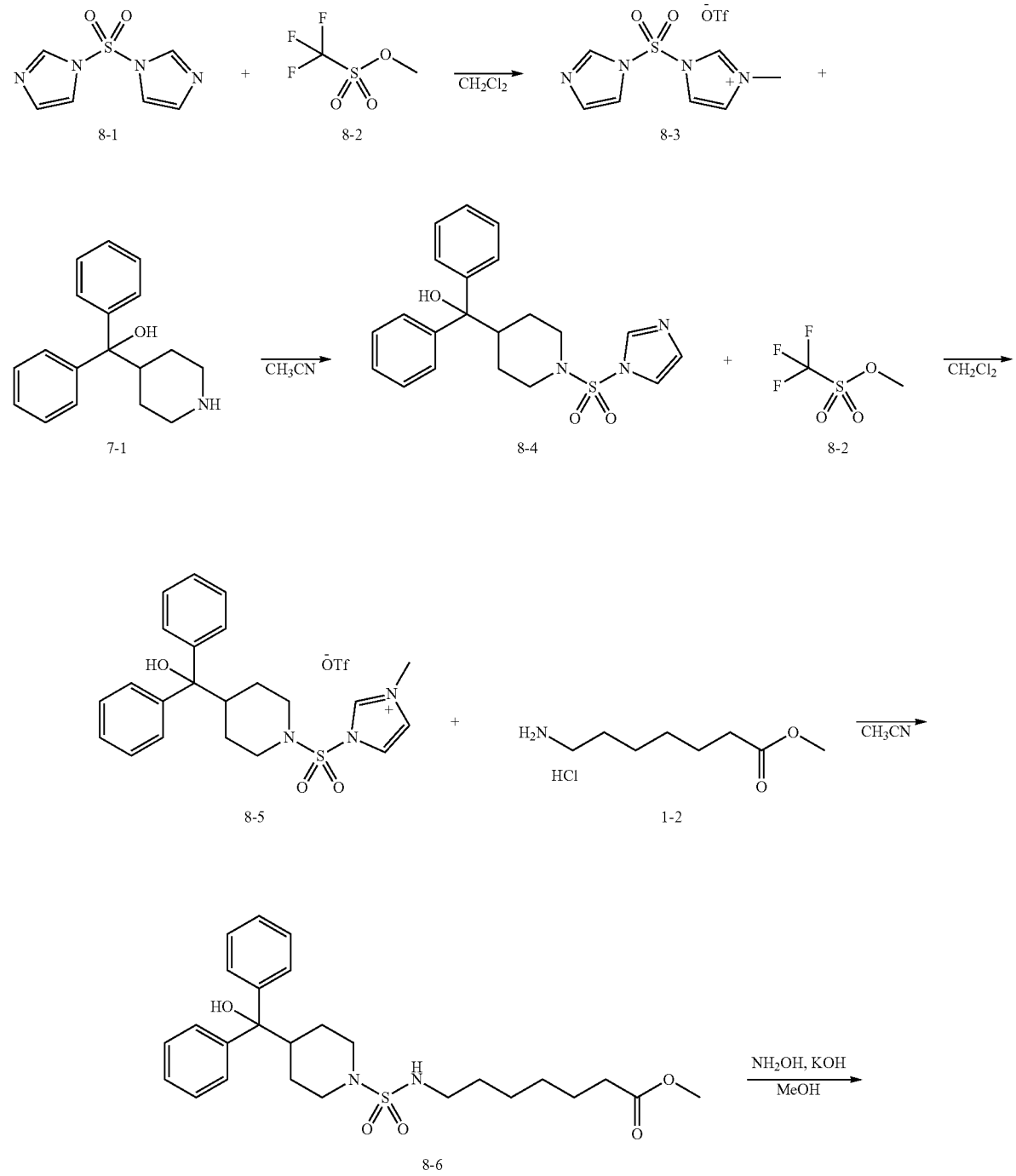

-continued

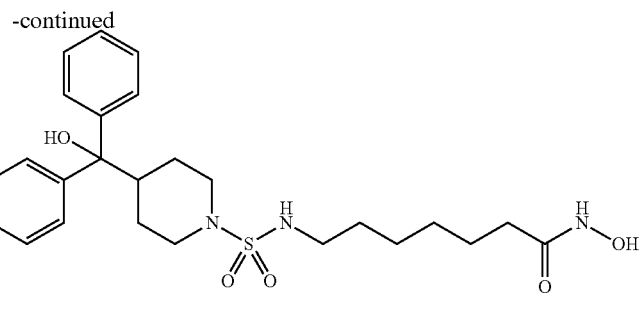
Compound 1210

As shown in reaction scheme 8 above, a compound of formula 8-1 is reacted with methyl trifluoromethanesulfonate (formula 8-2) to synthesize a compound of formula 8-3. The compound of formula 8-3 is reacted with diphenyl(piperidin-4-yl)methanol (formula 7-1) to synthesize a compound of formula 8-4, which is then reacted with methyl trifluoromethanesulfonate (formula 8-2) to synthesize a compound of formula 8-5. The compound of formula 8-5 is reacted with methyl 7-aminoheptanoate hydrochloride (formula 1-2) to synthesize a compound of formula 8-6. Then, potassium hydroxide (KOH), methanol and aqueous hydroxylamine solution are added to the compound of formula 8-6 and reacted at room temperature, thereby synthesizing final compound 1210.

[Reaction scheme 9]

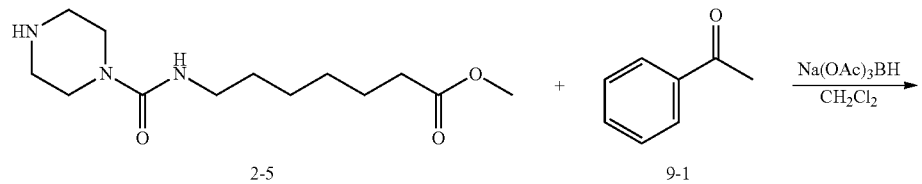

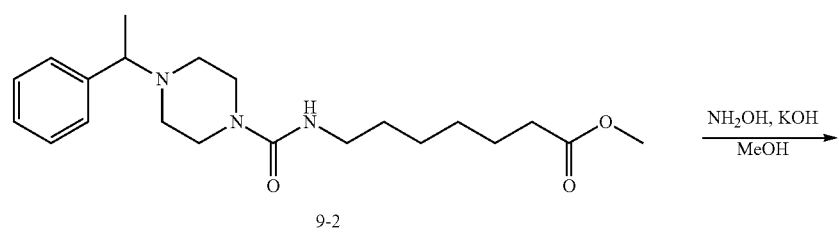
9-2

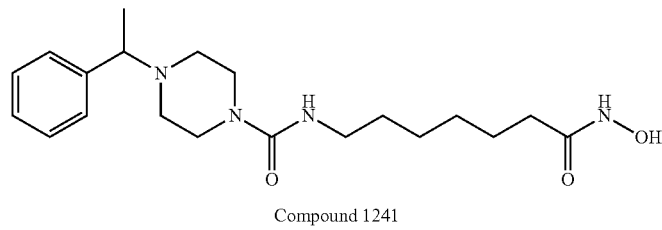
Compound 1241

As shown in reaction scheme 9 above, a compound of formula 2-5 is subjected to reductive amination with acetophenone to synthesize a compound of formula 9-2. Then, potassium hydroxide (KOH), methanol and aqueous hydroxylamine solution are added to the compound of formula 9-2 and reacted at room temperature, thereby synthesizing final compound 1241.

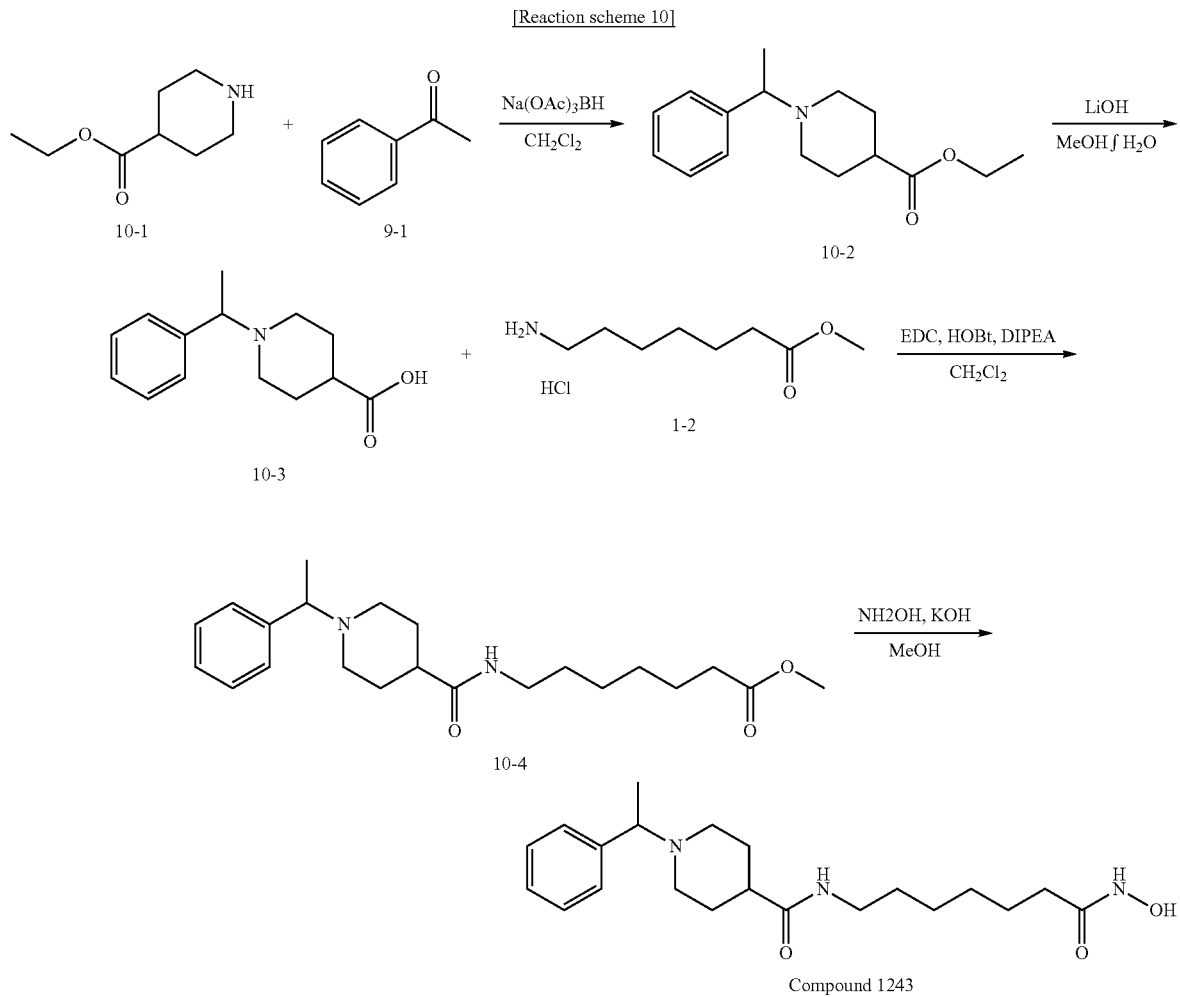

As shown in reaction scheme 10 above, a compound of formula 10-1 is subjected to reductive amination with acetophenone to synthesize a compound of formula 10-2, which is then hydrolyzed with lithium hydroxide (LiOH) to synthesize a compound of formula 10-3. The compound of formula 10-3 is subjected to amide coupling with methyl 7-aminoheptanoate hydrochloride to synthesize a compound of formula 10-4. Then, potassium hydroxide (KOH), methanol and aqueous hydroxylamine solution are added to the compound of formula 10-4 and reacted at room temperature, thereby synthesizing final compound 1243.

Advantageous Effects of Invention

The compounds represented by formula I according to the present invention, optical isomers thereof or pharmaceutically acceptable salts thereof can selectively inhibit HDAC and thus exhibit excellent effects on the prevention or treatment of histone deacetylase-mediated diseases.

BRIEF DESCRIPTION OF DRAWINGS

FIG. 1 shows the results of analyzing the effect of compound 1102 on the alleviation of arthritis in adjuvant-induced arthritis models.

MODE FOR THE INVENTION

Hereinafter, preferred examples will be presented to assist in the understanding of the present invention. However, these examples are provided only for a better understanding of the present invention and are not intended to limit the scope of the present invention.

The reagents and solvents mentioned below were purchased from Sigma-Aldrich and TCI unless otherwise specified, and HPLC was performed using Waters e2695. As silica gel for column chromatography, silica gel (230-400 mesh) from Merck was used.

$^1$H-NMR data were measured using Bruker 400 MHz, and mass spectra were obtained using Agilent 1100 series.

EXAMPLE 1

Synthesis of Compound 1102

Step 1: Synthesis of methyl 7-(4-benzhydrylpiperazine-1-carboxamido)heptanoate (formula 1-3)

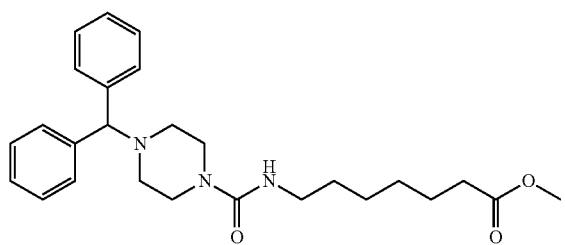

(1-3)

1-benzhydrylpiperazine (0.200 g, 0.793 mmol), methyl 7-aminoheptanoate (0.151 g, 0.951 mmol), triphosgene (0.118 g, 0.396 mmol) and DIPEA (0.415 mL, 2.378 mmol) were dissolved in methylene chloride (5 mL) at room temperature, and the solution was stirred at the same temperature for 1 hour. A saturated aqueous solution of sodium bicarbonate was added to the reaction mixture, followed by extraction with methylene chloride. The extract was filtered through a plastic filter to remove the solid residue and the aqueous layer, and then concentrated under reduced pressure. The concentrate was purified by column chromatography (Waters, $C_{18}$; 1%-formic acid (methanoic acid) aqueous solution/acetonitrile=from 100% to 20%) and concentrated by passage through an SPE cartridge (PL-$HCO_3$ resin), thereby obtaining the desired compound of formula 1-3 (0.075 g, 21.6%) as alight yellow oil.

Step 2: Synthesis of 4-benzhydryl-N-(7-(hydroxyamino)-7-oxoheptyl)piperazine-1-carboxamide (Compound 1102)

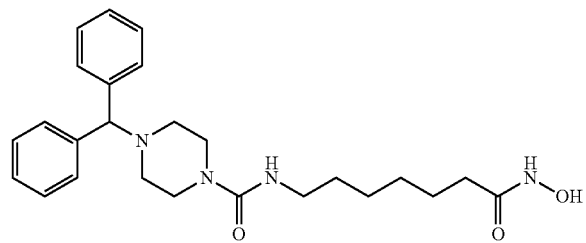

(Compound 1102)

The compound of formula 1-3 (0.075 g, 0.171 mmol) prepared in step 1, hydroxylamine (50.00% aqueous solution, 0.210 mL, 3.428 mmol) and potassium hydroxide (0.096 g, 1.714 mmol) were dissolved in methanol (3 mL) at room temperature, and the solution was stirred at the same temperature for 30 minutes. The reaction mixture was concentrated under reduced pressure to remove the solvent, and a saturated aqueous solution of sodium bicarbonate (20 mL) to the concentrate, followed by stirring. The precipitated solid was filtered, washed with water, and dried, thereby obtaining the desired compound 1102 (0.047 g, 62.5%) as a yellow solid.

$^1$H NMR (400 MHz, DMSO-$d_6$) δ 9.39 (brs, 1H), 7.42 (d, 4H, J=7.2 Hz), 7.29 (t, 4H, J=7.5 Hz), 7.18 (t, 2H, J=7.3 Hz), 6.40 (t, 1H, J=5.3 Hz), 4.28 (s, 1H), 3.27 (s, 4H), 2.98-2.93 (m, 2H), 2.08 (s, 4H), 1.89 (t, 2H, J=7.3 Hz), 1.44-1.43 (m, 2H), 1.34-1.33 (m, 2H), 1.20 (s, 4H); MS (ESI) m/z 439.6 ($M^+$+H).

EXAMPLE 2

Synthesis of Compound 1124

Step 1: Synthesis of 4-nitrophenyl 4-(hydroxydiphenylmethyl)piperidine-1-carboxylate (formula 7-3)

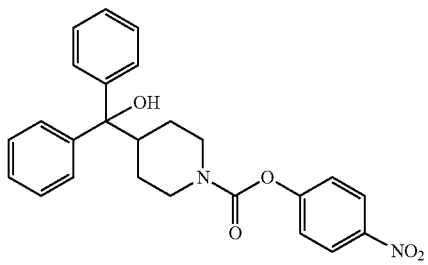

(7-3)

Diphenyl(piperidin-4-yl)methanol (0.100 g, 0.374 mmol) and triethylamine (0.104 mL, 0.748 mmol) were dissolved in methylene chloride (5 mL) at 0° C., and 4-nitrophenyl chloroformate (0.083 g, 0.411 mmol) was added to the solution, followed by stirring at the same temperature for 1 hour. A saturated aqueous solution of sodium bicarbonate was added to the reaction mixture, followed by extraction with methylene chloride. The extract was filtered through a plastic filter to remove the solid residue and the aqueous layer, and then concentrated under reduced pressure. The concentrate was purified by column chromatography (Sift, 4 g cartridge; ethyl acetate/hexane=from 0% to 20%) and concentrated, thereby obtaining the desired compound of formula 7-3 (0.152 g, 94.0%) as a colorless oil.

Step 2: Synthesis of methyl 7-(4-(hydroxydiphenylmethyl)piperidine-1-carboxamido)heptanoate (Formula 7-4)

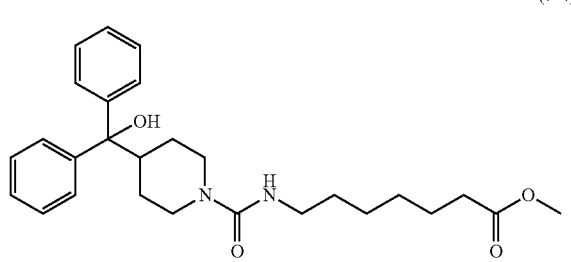

(7-4)

The compound of formula 7-3 (0.152 g, 0.351 mmol) prepared in step 1, methyl 7-aminoheptanoate hydrochloride (0.280 g, 1.757 mmol) and potassium carbonate (0.097 g, 0.703 mmol) were dissolved in N,N-dimethylformamide (5 mL) at room temperature, and the solution was stirred at 100° C. for 17 hours. Then, the temperature was lowered to room temperature to terminate the reaction. The reaction mixture was concentrated under reduced pressure to remove the solvent, and the concentrate was purified by column chromatography (SiO$_2$, 12 g cartridge; ethyl acetate/hexane=from 10% to 40%) and concentrated, thereby obtaining the compound of formula 7-4 (0.075 g, 39.4%) as an orange oil.

Step 3: N-(7-(hydroxyamino)-7-oxoheptyl)-4-(hydroxydiphenylmethyl)piperidine-1-carboxamide (Compound 1124)

(Compound 1124)

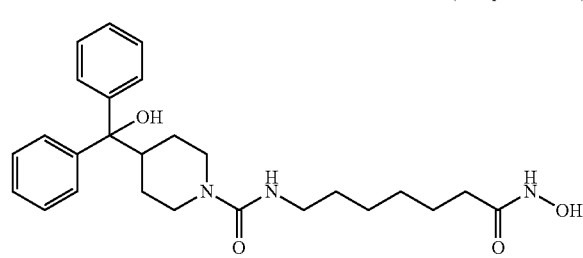

The compound of formula 7-4 (0.075 g, 0.166 mmol) prepared in step 2, hydroxylamine (50.00% aqueous solution, 0.203 mL, 3.314 mmol) and potassium hydroxide (0.093 g, 1.657 mmol) were dissolved in methanol (3 mL) at room temperature, and the solution was stirred at the same temperature for 1 hour. The reaction mixture was concentrated under reduced pressure to remove the solvent, and water was added to the concentrate, followed by extraction with methylene chloride. The organic layer was washed with a saturated aqueous solution of sodium chloride, dried with anhydrous magnesium sulfate, filtered, and then concentrated under reduced pressure. The precipitated solid was filtered, washed with hexane, and dried to afford the desired compound 1124 (0.007 g, 9.3%) as a white solid.

$^1$H NMR (400 MHz, DMSO-d$_6$) δ 9.36 (brs, 1H), 7.52 (d, 4H, J=7.6 Hz), 7.27 (t, 4H, J=7.7 Hz), 7.13 (t, 2H, J=7.3 Hz), 6.30 (t, 1H, J=5.3 Hz), 5.32 (brs, 1H), 3.94 (d, 2H, J=13.4 Hz), 2.99-2.94 (m, 2H), 2.67-2.58 (m, 3H), 1.91 (t, 2H, J=7.4 Hz), 1.48-1.46 (m, 2H), 1.35-1.34 (m, 2H), 1.30-1.25 (m, 6H).

EXAMPLE 3

Synthesis of Compound 1188

Step 1: Synthesis of (3S,5R)-1-benzhydryl-3,5-dimethylpiperazine (Compound 4-3)

(4-3)

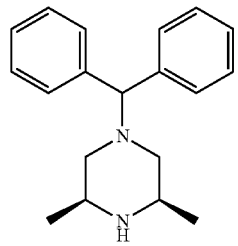

(2R,6S)-2,6-dimethylpiperazine (1.000 g, 8.757 mmol), (chloromethylene)dibenzene (3.550 g, 17.515 mmol) and potassium carbonate (6.052 g, 43.787 mmol) were dissolved in N,N-dimethylformamide (10 mL) at room temperature, and the solution was stirred at the same temperature for 17 hours. The reaction mixture was concentrated under reduced pressure to remove the solvent, and water was added to the concentrate, followed by extraction with methylene chloride. The extract was filtered through a plastic filter to remove the solid residue and the aqueous layer, and then concentrated under reduced pressure. The concentrate was purified by column chromatography (Sift, 12 g cartridge; methanol/methylene chloride=from 0% to 10%) and concentrated to afford the desired compound of formula 4-3 (0.798 g, 32.5%) as a white solid.

Step 2: Synthesis of methyl 7-((2S,6R)-4-benzhydryl-2,6-dimethylpiperazine-1-carboxamido)heptanoate (Formula 4-4)

(4-4)

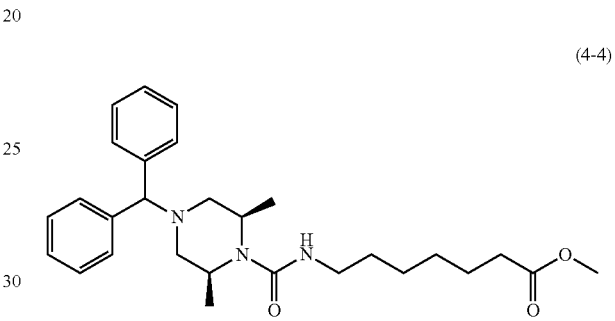

Triphosgene (0.159 g, 0.535 mmol) and diisopropylamine (0.561 mL, 3.210 mmol) were dissolved in methylene chloride (5 mL) at 0° C., and methyl 7-aminoheptanoate hydrochloride (0.251 g, 1.284 mmol) was added to the solution, followed by stirring at the same temperature. The compound of formula 4-3 (0.300 g, 1.070 mmol) prepared in step 1 was added to the reaction mixture, followed by stirring at the same temperature for 30 minutes. Water was added to the reaction mixture, followed by extraction with methylene chloride. The extract was filtered through a plastic filter to remove the solid residue and the aqueous layer, and then concentrated under reduced pressure. The concentrate was purified by column chromatography (SiO$_2$, 12 g cartridge; ethyl acetate/hexane=from 0% to 30%) and concentrated to afford the desired compound of formula 4-4 (0.212 g, 42.6%) as a white solid.

Step 3: Synthesis of (2S,6R)-4-benzhydryl-N-(7-(hydroxyamino)-7-oxoheptyl)-2,6-dimethylpiperazine-1-carboxyamide (Compound 1188)

(Compound 1188)

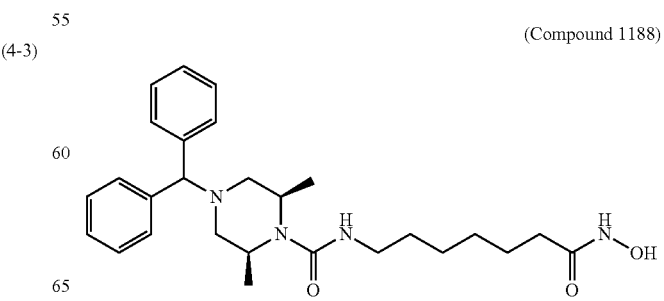

The compound of formula 4-4 (0.100 g, 0.215 mmol) prepared in step 2, hydroxylamine (50.00% aqueous solution, 0.263 mL, 4.295 mmol) and potassium hydroxide (0.121 g, 2.148 mmol) were dissolved in methanol (3 mL) at room temperature, and the solution was stirred at the same temperature for 1 hour. The reaction mixture was concentrated under reduced pressure to remove the solvent, and a saturated aqueous solution of sodium bicarbonate (30 mL) was added to the concentrate, followed by stirring. The precipitated solid was filtered, washed with water and dried to afford the desired compound 1188 (0.099 g, 98.8%) as a white solid.

$^1$H NMR (400 MHz, DMSO-d$_6$) δ 7.51 (d, 4H, J=7.5 Hz), 7.30 (t, 4H, J=7.6 Hz), 7.19 (t, 2H, J=7.3 Hz), 6.23 (t, 1H, J=5.3 Hz), 4.23 (s, 1H), 3.94 (brs, 2H), 3.03-2.98 (m, 2H), 2.60 (d, 2H, J=10.9 Hz), 1.96-1.90 (m, 4H), 1.46-1.45 (m, 2H), 1.38-1.36 (m, 2H), 1.26-1.22 (m, 10H).

EXAMPLE 4

Synthesis of Compound 1189

Step 1: Synthesis of tert-butyl (R)-4-benzhydryl-2-methylpiperazine-1-carboxylate (Formula 4-5)

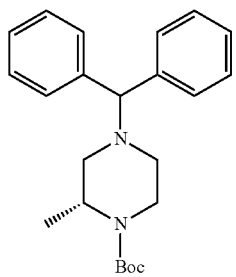

(4-5)

(R)-tert-butyl 2-methylpiperazine-1-carboxylate (1.000 g, 4.993 mmol), (chloromethylene)dibenzene (2.024 g, 9.986 mmol) and potassium carbonate (3.450 g, 24.965 mmol) were dissolved in N,N-dimethylformamide (10 mL) at room temperature, and the solution was stirred at 80° C. for 17 hours and then cooled to room temperature to terminate the reaction. The reaction mixture was concentrated under reduced pressure to remove the solvent, and water was added to the concentrate, followed by extraction with methylene chloride. The extract was filtered through a plastic filter to remove the solid residue and the aqueous layer, and then concentrated under reduced pressure. The concentrate was purified by column chromatography (SiO$_2$, 12 g cartridge; ethyl acetate/hexane=from 0% to 10%) and concentrated to afford the desired compound of formula 4-5 (0.813 g, 44.4%) as a white solid.

Step 2: Synthesis of (R)-1-benzhydryl-3-methylpiperazine (Formula 4-6)

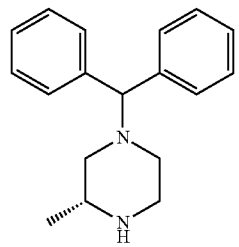

(4-6)

The compound of formula 4-5 (0.813 g, 2.218 mmol) prepared in step 1 was dissolved in methylene chloride (10 mL) at room temperature and hydrochloric acid (4.00 M dioxane solution, 5.546 mL, 22.183 mmol) was added to the solution, followed by stirring at the same temperature for 17 hours. A saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered and then concentrated under reduced pressure. The desired compound of formula 4-6 (0.590 g, 99.8%) was obtained as a white solid without additional purification.

Step 3: Synthesis of methyl (R)-7-(4-benzhydryl-2-methylpiperazine-1-carboxamido)heptanoate (Formula 4-7)

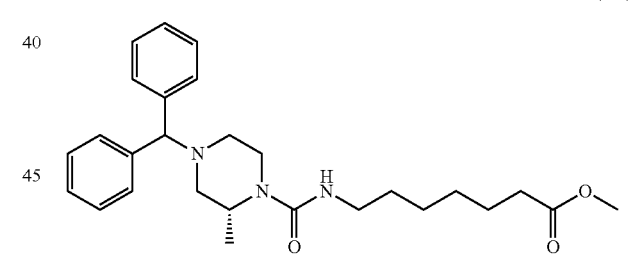

(4-7)

Triphosgene (0.167 g, 0.563 mmol) and DIPEA (1.180 mL, 6.757 mmol) were dissolved in methylene chloride (5 mL) at 0° C., and methyl 7-aminoheptanoate hydrochloride (0.264 g, 1.351 mmol) was added to the solution, followed by stirring at the same temperature. The compound of formula 4-6 (0.300 g, 1.126 mmol) was added to the reaction mixture, followed by stirring at the same temperature for 30 minutes. A saturated aqueous solution of sodium bicarbonate was added to the reaction mixture, followed by extraction with methylene chloride. The extract was filtered through a plastic filter to remove the solid residue and the aqueous layer, and then concentrated under reduced pressure. The concentrate was purified by column chromatography (SiO$_2$, 12 g cartridge; ethyl acetate/hexane=from 0% to 30%) and concentrated. Then, the concentrate was purified again by chromatography (Waters, C$_{18}$; 1%-formic acid (methanoic acid) aqueous solution/acetonitrile=from 75% to 5%) and concentrated by passage through an SPE cartridge (PL-HCO₃ resin) to afford the desired compound of formula 4-7 (0.106 g, 20.8%).

Step 4: Synthesis of (R)-4-benzhydryl-N-(7-(hydroxyamino)-7-oxoheptyl)-2-methylpiperazine-1-carboxamide (Compound 1189)

(Compound 1189)

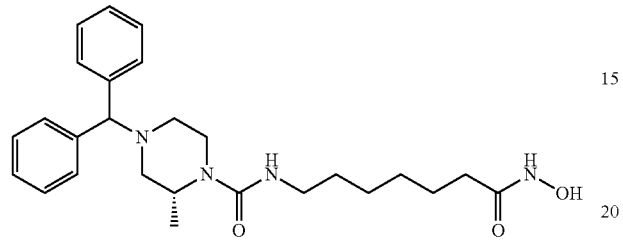

The compound of formula 4-7 (0.100 g, 0.221 mmol) prepared in step 3, hydroxylamine (50.00% aqueous solution, 0.271 mL, 4.429 mmol) and potassium hydroxide (0.124 g, 2.214 mmol) were dissolved in methanol (3 mL) at room temperature, and the solution was stirred at the same temperature for 1 hour. The reaction mixture was concentrated under reduced pressure to remove the solvent, and an aqueous solution of sodium bicarbonate (30 mL) was added to the concentrate, followed by stirring. The precipitated solid was filtered, washed with water and dried to afford the desired compound 1189 (0.099 g, 98.8%) as a white solid.

¹H NMR (400 MHz, DMSO-d₆) δ 9.42 (brs, 2H), 7.45 (t, 4H, J=6.3 Hz), 7.30 (t, 4H, J=7.6 Hz), 7.19 (t, 2H, J=6.8 Hz), 6.36-6.34 (m, 1H), 4.23 (s, 1H), 4.04 (brs, 1H), 3.62 (d, 1H, J=12.4 Hz), 3.01-2.93 (m, 3H), 2.67 (d, 1H, J=9.6 Hz), 2.60 (d, 1H, J=10.8 Hz), 1.95 (dd, 1H, J=11.0, 3.0 Hz), 1.88 (t, 2H, J=7.3 Hz), 1.78 (t, 1H, J=10.1 Hz), 1.44-1.43 (m, 2H), 1.36-1.35 (m, 2H), 1.20-1.18 (m, 7H).

EXAMPLE 5

Synthesis of Compound 1190

Step 1: Synthesis of tert-butyl (S)-4-benzhydryl-2-methylpiperazine-1-carboxylate (Formula 4-5)

(4-5)

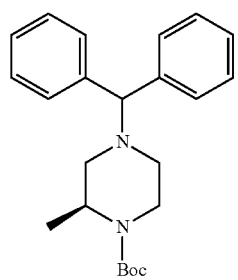

(S)-tert-butyl 2-methylpiperazine-1-carboxylate (1.000 g, 4.993 mmol), (chloromethylene)dibenzene (2.024 g, 9.986 mmol) and potassium carbonate (3.450 g, 24.965 mmol) were dissolved in N,N-dimethylformamide (10 mL) at room temperature, and the solution was stirred at 80° C. for 17 hours, and then cooled to room temperature to terminate the reaction. The reaction mixture was concentrated under reduced pressure to remove the solvent, and water was added to the concentrate, followed by extraction with methylene chloride. The extract was filtered through a plastic filter to remove the solid residue and the aqueous layer, and then concentrated under reduced pressure. The concentrate was purified by column chromatography (SiO₂, 12 g cartridge; ethyl acetate/hexane=from 0% to 10%) and concentrated to afford the desired compound of formula 4-5 (0.742 g, 40.5%) as a white solid.

Step 2: Synthesis of(S)-1-benzhydryl-3-methylpiperazine (Formula 4-6)

(4-6)

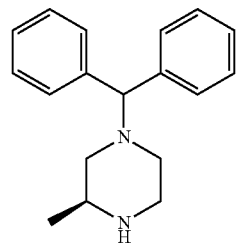

The compound of formula 4-5 (0.742 g, 2.025 mmol) prepared in step 1 was dissolved in methylene chloride (10 mL) at room temperature, and hydrochloric acid (4.00 M dioxane solution, 5.061 mL, 20.246 mmol) was added to the solution, followed by stirring at the same temperature for 17 hours. A saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered and then concentrated under reduced pressure. The product (0.530 g, 98.3%, white solid) was used without additional purification.

Step 3: Synthesis of methyl (S)-7-(4-benzhydryl-2-methylpiperazine-1-carboxamido)heptanoate (Formula 4-7)

(4-7)

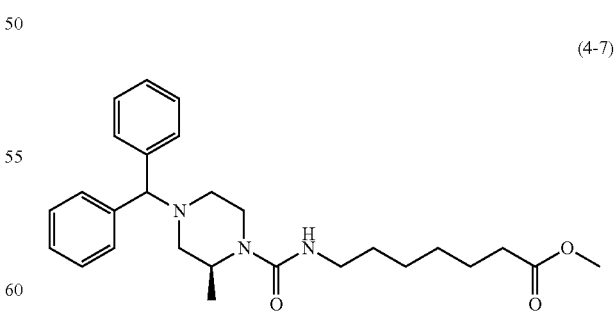

Triphosgene (0.111 g, 0.375 mmol) and DIPEA (0.582 g, 4.505 mmol) were dissolved in methylene chloride (5 mL) at 0° C., and methyl 7-aminoheptanoate hydrochloride (0.176 g, 0.901 mmol) was added to the solution, followed by stirring at the same temperature. The compound of formula 4-6 (0.200 g, 0.751 mmol) prepared in step 2 was added to the reaction mixture, followed by stirring at the same temperature for 30 minutes. Water was added to the reaction mixture, followed by extraction with methylene chloride. The extract was filtered through a plastic filter to remove the solid residue and the aqueous layer, and then concentrated under reduced pressure. The concentrate was purified by column chromatography ($SiO_2$, 12 g cartridge; ethyl acetate/hexane=from 0% to 30%) and concentrated to afford the desired compound of 4-7 (0.213 g, 62.8%) as a light yellow oil.

Step 4: Synthesis of (S)-4-benzhydryl-N-(7-(hydroxyamino)-7-oxoheptyl)-2-methylpiperazine-1-carboxamide (Compound 1190)

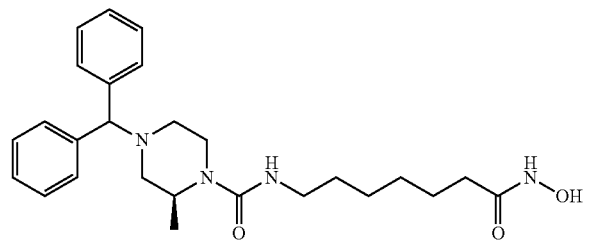

(Compound 1190)

The compound of formula 4-7 (0.100 g, 0.221 mmol) prepared in step 3, hydroxylamine (50.00% aqueous solution, 0.271 mL, 4.429 mmol) and potassium hydroxide (0.124 g, 2.214 mmol) were dissolved in methanol (3 mL) at room temperature, and the solution was stirred at the same temperature for 1 hour. The reaction mixture was concentrated under reduced pressure to remove the solvent, and an aqueous solution of sodium bicarbonate (30 mL) was added to the concentrate, followed by stirring. The precipitated solid was filtered, washed with water and dried to afford the desired compound 1190 (0.093 g, 92.8%) as a light orange solid.

$^1$H NMR (400 MHz, DMSO-$d_6$) δ 9.43 (brs, 2H), 7.45 (t, 4H, J=6.3 Hz), 7.30 (t, 4H, J=7.6 Hz), 6.35 (t, 1H, J=5.5 Hz), 4.23 (s, 1H), 4.04 (brs, 1H), 3.62 (d, 1H, J=12.6 Hz), 3.03-2.92 (m, 3H), 2.67 (d, 1H, J=10.6 Hz), 2.60 (d, 1H, J=11.2 Hz), 1.95 (dd, 1H, J=11.1, 3.1 Hz), 1.88 (t, 2H, J=7.4 Hz), 1.80-1.75 (m, 1H), 1.45-1.43 (m, 2H), 1.36-1.34 (m, 2H), 1.20-1.18 (m, 7H).

EXAMPLE 6

Synthesis of Compound 1209

Step 1: Synthesis of ethyl 1-benzhydrylpiperidine-4-carboxylate (Formula 5-2)

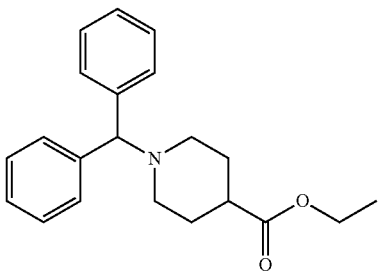

(5-2)

Ethyl piperidine-4-carboxylate (3.000 g, 19.083 mmol), (chloromethylene)dibenzene (5.802 g, 28.624 mmol) and potassium carbonate (13.187 g, 95.414 mmol) were dissolved in N,N-dimethylformamide (50 mL), and the solution was stirred at room temperature for 17 hours, and then stirred at 80° C. for 3 hours. Then, the solution was cooled to room temperature to terminate the reaction. The reaction mixture was concentrated under reduced pressure to remove the solvent, and water was added to the concentrate, followed by extraction with ethyl acetate. The organic layer was washed with a saturated aqueous solution of sodium chloride, dried with anhydrous magnesium sulfate, filtered and then concentrated under reduced pressure. The concentrate was purified by column chromatography ($SiO_2$, 40 g cartridge; ethyl acetate/hexane=from 0% to 15%) and concentrated to afford the desired compound of formula 5-2 (1.410 g, 22.8%) as a colorless oil.

Step 2: Synthesis of 1-benzhydrylpiperidine-4-carboxylic acid (Formula 5-3)

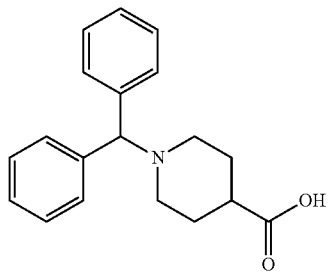

(5-3)

The compound of formula 5-2 (1.410 g, 4.360 mmol) prepared in step 1 and LiOH (0.209 g, 8.719 mmol) were dissolved in methanol (10 mL)/water (5 mL) at room temperature, and the solution was stirred at 60° C. for 17 hours, and then cooled to room temperature to terminate the reaction. The reaction mixture was concentrated under reduced pressure to remove the solvent, and then neutralized with an aqueous solution of 1 N hydrochloric acid and concentrated under reduced pressure to remove the solvent. The product (1.300 g, 101.0%, white solid) was used without additional purification.

Step 3: Synthesis of methyl 7-(1-benzhydrylpiperidine-4-carboxamido)heptanoate (Formula 5-4)

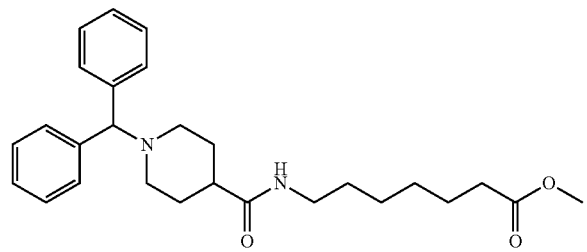

(5-4)

The compound of formula 5-3 (1.500 g, 5.078 mmol) prepared in step 2, methyl 7-aminoheptanoate hydrochloride (1.988 g, 10.156 mmol), EDC (1.947 g, 10.156 mmol), HBOt (1.372 g, 10.156 mmol) and diisopropylamine (4.435 mL, 25.391 mmol) were dissolved in methylene chloride (30 mL) at room temperature, and the solution was stirred at the same temperature for 17 hours. A saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered and then concentrated under reduced pressure. The concentrate was purified by column chromatography (SiO$_2$, 40 g cartridge; ethyl acetate/hexane=from 0% to 40%) and concentrated to afford the desired compound of formula 5-4 (1.810 g, 81.6%) as a colorless oil.

Step 4: Synthesis of 1-benzhydryl-N-(7-(hydroxyamino)-7-oxoheptyl)piperidine-4-carboxamide (Compound 1209)

(Compound 1209)

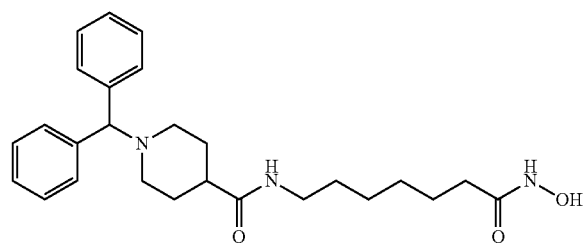

The compound of formula 5-4 (1.000 g, 2.290 mmol) prepared in step 3, hydroxylamine (50.00% aqueous solution, 2.802 mL, 45.809 mmol) and potassium hydroxide (1.285 g, 22.904 mmol) were dissolved in methanol (15 mL) at 0° C., and the solution was stirred at the same temperature for 1 hour. The reaction mixture was concentrated under reduced pressure to remove the solvent, and a saturated aqueous solution of sodium bicarbonate was added to the concentrate, followed by extraction with methylene chloride. The organic layer was washed with a saturated aqueous solution of sodium chloride, dried with anhydrous magnesium sulfate, filtered and then concentrated under reduced pressure.

The desired compound 1209 (1.000 g, 99.8%) was obtained as a light orange solid without additional purification.

$^1$H NMR (400 MHz, DMSO-d$_6$) δ 7.71 (t, 1H, J=5.4 Hz), 7.40 (d, 4H, J=7.3 Hz), 7.27 (t, 4H, J=7.5 Hz), 7.16 (t, 2H, J=7.3 Hz), 4.25 (s, 1H), 2.98 (q, 2H, J=6.4 Hz), 2.79 (d, 2H, J=11.0 Hz), 2.09~2.02 (m, 1H), 1.89 (t, 2H, J=7.3 Hz), 1.77 (t, 2H, J=9.8 Hz), 1.66~1.59 (m, 4H), 1.45~1.39 (m, 2H), 1.34~1.32 (m, 2H), 1.29~1.27 (m, 4H); MS (ESI) m/z 438.2 (M$^+$+H).

EXAMPLE 7

Synthesis of Compound 1210

Step 1: Synthesis of 1-((1H-imidazol-1-yl)sulfonyl)-3-methyl-1H-imidazol-3-ium trifluoromethanesulfonate (Formula 8-3)

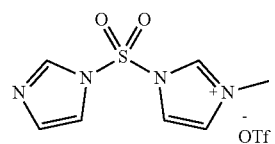

(8-3)

1,1'-sulfonylbis(1H-imidazole) (5.000 g, 25.227 mmol) and methyl trifluoromethanesulfonate (2.855 mL, 25.227 mmol) were dissolved in methylene chloride (100 mL) at room temperature, and the solution was stirred at the same temperature for 3 hours. The precipitated solid was filtered and dried to afford the desired compound of formula 8-3 (5.160 g, 45.3%) as a light yellow oil.

Step 2: Synthesis of (1-((1H-imidazol-1-yl)sulfonyl)piperidin-4-yl)diphenylmethanol (Formula 8-4)

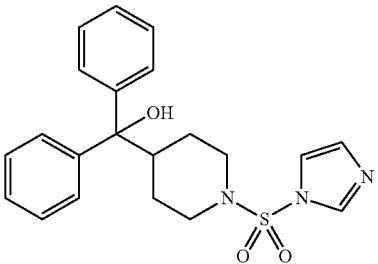

(8-4)

Diphenyl(piperidin-4-yl)methanol (1.000 g, 3.740 mmol) and the compound of formula 8-3 (2.033 g, 5.610 mmol) prepared in step 1 were dissolved in acetonitrile (20 mL) at room temperature, and the solution was stirred at the same temperature for 17 hours. The reaction mixture was concentrated under reduced pressure, and the concentrate was purified by column chromatography (Sift, 12 g cartridge; ethyl acetate/hexane=from 0% to 40%) and concentrated to afford the desired compound of formula 8-4 (0.487 g, 32.8%) as a white solid.

Step 3: (1-((3-methyl-1H-3-ium-imidazol-1-yl)sulfonyl)piperidin-4-yl)diphenylmethanol trifluoromethanesulfonate (formula 8-5)

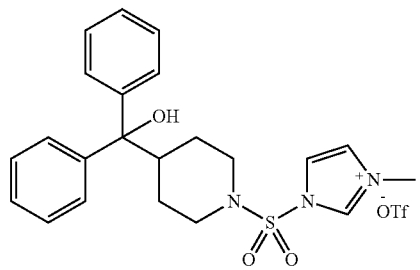

(8-5)

The compound of formula 8-4 (0.487 g, 1.225 mmol) prepared in step 2 and methyl trifluoromethanesulfonate (0.146 mL, 1.286 mmol) were dissolved in methylene chloride (10 mL) at 0° C., and the solution was stirred at room temperature for 2 hours. The precipitated solid was filtered, washed with methylene chloride and dried to afford the desired compound of formula 8-5 (0.670 g, 97.4%) as a white solid.

Step 4: Synthesis of methyl 7-((4-(hydroxydiphenylmethyl)piperidine)-1-sulfonamido)hepatanoate (Formula 8-6)

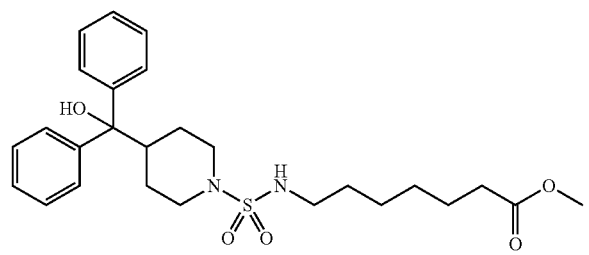

(8-6)

The compound of formula 8-5 (0.504 g, 0.897 mmol) prepared in step 3 and methyl 7-aminoheptanoate hydrochloride (0.228 g, 1.167 mmol) were dissolved in acetonitrile (3 mL) at 80° C., and the solution was stirred at the same temperature for 12 hours, and then cooled to room temperature to terminate the reaction. Water was added to the reaction mixture, followed by extraction with ethyl acetate. The organic layer was washed with a saturated aqueous solution of sodium chloride, dried with anhydrous magnesium sulfate, filtered and then concentrated under reduced pressure. The concentrate was purified by column chromatography (Sift, 12 g cartridge; ethyl acetate/hexane=from 10% to 60%) and concentrated to afford the desired compound of formula 8-6 (0.147 g, 33.5%) as a white solid.

Step 5: Synthesis of N-hydroxy-7-((4-(hydroxydiphenylmethyl)piperidine)-1-sulfonamido)heptanamide (Compound 1210)

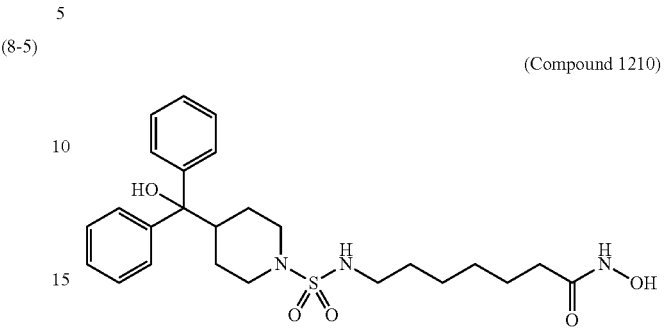

(Compound 1210)

The compound of formula 8-6 (0.150 g, 0.307 mmol) prepared in step 4, potassium hydroxide (0.172 g, 3.070 mmol) and hydroxylamine (50.00% solution, 0.188 mL, 3.070 mmol) were dissolved in methanol (1 mL) at room temperature, and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered and then concentrated under reduced pressure. The desired compound 1210 (0.067 g, 44.6%) was obtained as a white solid and used without additional purification.

$^1$H NMR (400 MHz, DMSO-$d_6$) δ 10.34 (s, 1H), 8.68 (s, 1H), 7.52 (d, 4H, J=7.4 Hz), 7.26 (t, 4H, J=7.6 Hz), 7.12 (m, 3H), 3.46 (m, 2H), 2.82 (m, 2H), 2.63 (m, 3H), 1.93 (t, 2H, J=7.3 Hz), 1.48-1.22 (m, 13H); MS (ESI) m/z 490.6 (M$^+$+H).

EXAMPLE 8

Synthesis of Compound 1213

Step 1: Synthesis of methyl 7-(4-benzhydryl-N-methylpiperizine-1-carboxamido)heptanoate (Formula 1-4)

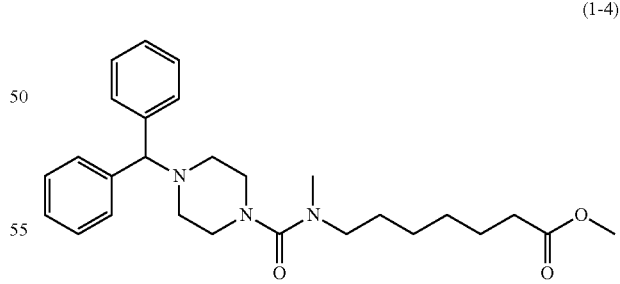

(1-4)

Methyl 7-(4-benzhydrylpiperazine-1-carboxamido)heptanoate (0.100 g, 0.229 mmol) and sodium hydride (60.00%, 0.046 g, 1.143 mmol) were dissolved in N,N-dimethylformamide (3 mL) at 0° C., and iodomethane (0.071 mL, 1.143 mmol) was added to the solution, followed by stirring at the same temperature for 10 minutes. Water was added to the reaction mixture, followed by extraction with ethyl acetate. The organic layer was washed with a saturated aqueous solution of sodium chloride, dried with anhydrous magnesium sulfate, filtered and then concentrated under reduced pressure. The concentrate was purified by column chromatography (Sift, 4 g cartridge; ethyl acetate/hexane=from 10% to 40%) and concentrated to afford the desired compound of formula 1-4 (0.097 g, 94.0%) as a colorless oil.

Step 2: Synthesis of 4-benzhydryl-N-(7-(hydroxyamino)-7-oxoheptyl)-N-methylpiperazine-1-carboxamide (Compound 1213)

(Compound 1213)

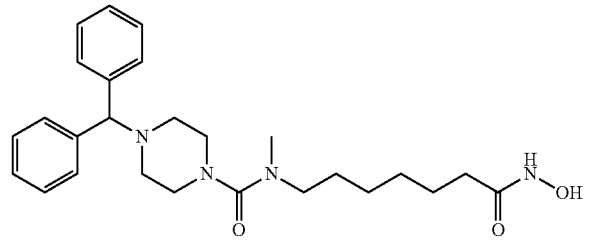

The compound of formula 1-4 (0.097 g, 0.215 mmol) prepared in step 1, hydroxylamine (50.00% aqueous solution, 0.263 mL, 4.296 mmol) and potassium hydroxide (0.121 g, 2.148 mmol) were dissolved in methanol (3 mL) at room temperature, and the solution was stirred at the same temperature for 1 hour. A saturated aqueous solution of sodium bicarbonate was added to the reaction mixture, followed by extraction with methylene chloride. The extract was filtered through a plastic filter to remove the solid residue and the aqueous layer, and then concentrated under reduced pressure. The desired compound 1213 (0.010 g, 10.3%) was obtained as a white solid without additional purification.

$^1$H NMR (400 MHz, CD$_3$OD) δ 7.44 (d, 4H, J=7.4 Hz), 7.27 (t, 4H, J=7.5 Hz), 7.17 (t, 2H, J=7.3 Hz), 4.26 (s, 1H), 3.24-3.22 (m, 4H), 3.17 (t, 2H, J=7.2 Hz), 2.81 (s, 3H), 2.41-2.38 (m, 4H), 2.07 (t, 2H, J=7.4 Hz), 1.62-1.52 (m, 4H), 1.33-1.24 (m, 4H); MS (ESI) m/z 453.4 (M$^+$+H).

EXAMPLE 9

Synthesis of Compound 1221

Step 1: Synthesis of N,N-diphenylpiperidine-4-amine hydrochloride (Formula 6-4)

(6-4)

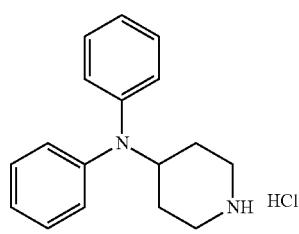

Tert-butyl 4-(diphenylamino)piperidine-1-carboxylate (1.000 g, 2.837 mmol) was dissolved in methylene chloride (10 mL) at room temperature, and hydrochloric acid (4.00 M 1,4-dioxane solution, 3.546 mL, 14.185 mmol) was added to the solution, followed by stirring at the same temperature for 17 hours. The precipitated solid was filtered, washed with methylene chloride and dried to afford the desired compound of formula 6-4 (0.800 g, 97.6%) as a white solid.

Step 2: Synthesis of N,N-diphenylpiperidine-4-amine (Formula 6-5)

(6-5)

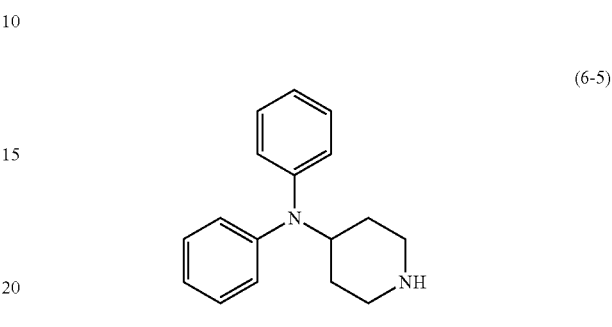

The compound of formula 6-4 (0.600 g, 2.077 mmol) prepared in step 1 was dissolved in water (5 mL) at room temperature, and a saturated aqueous solution of sodium bicarbonate (50 mL) was added to the solution, followed by stirring at the same temperature for 1 hour. A saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered and then concentrated under reduced pressure. The product (0.496 g, 94.6%, colorless oil) was used without additional purification.

Step 3: Synthesis of methyl 7-(4-(diphenylamino)piperidine-1-carboxamido)heptanoate (Formula 6-6)

(6-6)

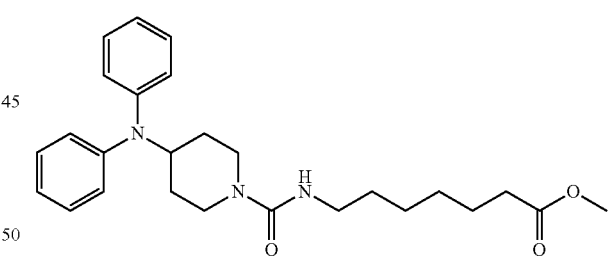

The compound of formula 6-5 (0.100 g, 0.396 mmol) prepared in step 2, methyl 7-aminoheptanoate hydrochloride (0.078 g, 0.396 mmol), triphosgene (0.059 g, 0.198 mmol) and DIPEA (0.415 mL, 2.378 mmol) were dissolved in methylene chloride (3 mL) at 0° C., and the solution was stirred at the same temperature for 1 hour. Then, a saturated aqueous solution of sodium bicarbonate (50 mL) was added to the reaction mixture at 0° C., followed by stirring for 10 minutes. After completion of the reaction, water was added to the reaction mixture, followed by extraction with ethyl acetate. The organic layer was washed with a saturated aqueous solution of sodium chloride, dried with anhydrous magnesium sulfate, filtered and then concentrated under reduced pressure. The concentrate was purified by column chromatography (Sift, 4 g cartridge; ethyl acetate/hexane=from 10% to 60%) and concentrated to afford the desired compound of formula 6-6 (0.096 g, 55.4%) as a light yellow oil.

Step 4: Synthesis of 4-(diphenylamino)-N-(7-(hydroxyamino)-7-oxoheptyl)piperidine-1-carboxamide (Compound 1221)

(Compound 1221)

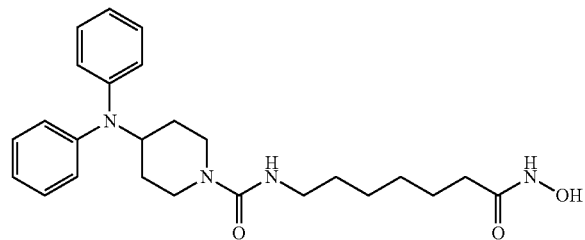

The compound of formula 6-6 (0.096 g, 0.219 mmol) prepared in step 3, hydroxylamine (50.00% aqueous solution, 0.268 mL, 4.388 mmol) and potassium hydroxide (0.123 g, 2.194 mmol) were dissolved in methanol (3 mL) at room temperature, and the solution was stirred at the same temperature for 1 hour. The reaction mixture was concentrated under reduced pressure to remove the solvent, and a saturated aqueous solution of sodium bicarbonate (20 mL) and methylene chloride (5 mL) were added to the concentrate, followed by stirring. The precipitated solid was filtered, washed with water and dried to afford the desired compound 1221 (0.076 g, 79.0%) as a white solid.

$^1$H NMR (400 MHz, DMSO-$d_6$) δ 7.27 (t, 4H, J=7.8 Hz), 6.97 (t, 2H, J=7.2 Hz), 6.79 (d, 4H, J=7.8 Hz), 6.35 (t, 1H, J=5.4 Hz), 4.10-4.04 (m, 1H), 3.97 (d, 2H, J=13.1 Hz), 2.90 (q, 2H, J=6.4 Hz), 2.78 (t, 2H, J=12.5 Hz), 1.90 (t, 2H, J=7.3 Hz), 1.84 (d, 2H, J=12.5 Hz), 1.46-1.39 (m, 2H), 1.31-1.27 (m, 2H), 1.17-1.10 (m, 4H), 1.08-1.01 (m, 2H).

EXAMPLE 10

Synthesis of Compound 1222

Step 1: Synthesis of di(pyridin-2-yl)methanol (Formula 3-2)

(3-2)

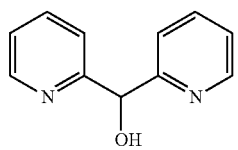

Di(pyridin-2-yl)methanone (2.000 g, 10.858 mmol) was dissolved in methanol (20 mL) at 0° C., and NaBH$_4$ (0.452 g, 11.944 mmol) was added to the solution, followed by stirring at the same temperature for 1 hour. Then, a saturated aqueous solution of sodium bicarbonate (10 mL) was added to the reaction mixture at 0° C., followed by stirring for 10 minutes. After completion of the reaction, water was added to the reaction mixture, followed by extraction with methylene chloride. The organic layer was washed with a saturated aqueous solution of sodium chloride, dried with anhydrous magnesium sulfate, filtered and then concentrated under reduced pressure. The desired compound of formula 3-2 (2.000 g, 98.9%) was obtained as a red oil and used without additional purification.

Step 2: Synthesis of di(pyridin-2-yl)methylmethanesulfonate (Formula 3-3)

(3-3)

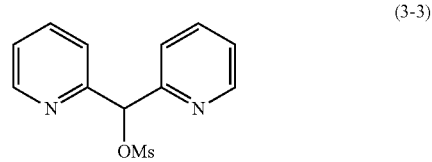 [SMILES: CS(=O)(=O)OC(c1ccccn1)c1ccccn1]

The compound of formula 3-2 (1.000 g, 5.370 mmol) prepared in step 1, methanesulfonyl chloride (0.623 mL, 8.055 mmol) and triethylamine (2.246 mL, 16.111 mmol) were dissolved in methylene chloride (10 mL) at 0° C., and the solution was stirred at the same temperature for 1 hour. Water was added to the reaction mixture, followed by extraction with ethyl acetate. The organic layer was washed with a saturated aqueous solution of sodium chloride, dried with anhydrous magnesium sulfate, filtered and then concentrated under reduced pressure. The concentrate was purified by column chromatography (SiO$_2$, 12 g cartridge; ethyl acetate/hexane=from 0% to 30%) and concentrated to afford the desired compound of formula 3-3 (0.670 g, 47.2%) as a pink solid.

Step 3: Synthesis of methyl 7-(4-(di(pyridin-2-yl)methyl)piperazine-1-carboxamido)heptanoate (Formula 3-4)

(3-4)

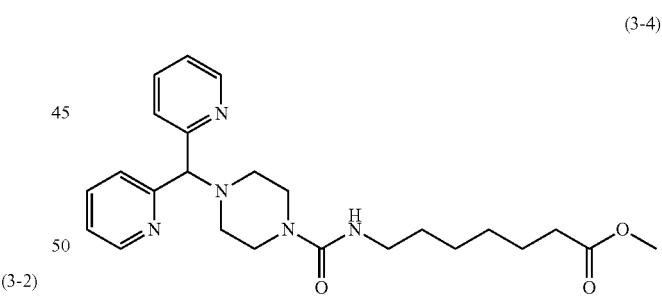

The compound of formula 3-3 (0.258 g, 0.975 mmol) prepared in step 2, the compound of formula 2-5 (0.200 g, 0.650 mmol) and potassium carbonate (0.449 g, 3.249 mmol) were dissolved in N,N-dimethylformamide (4 mL) at room temperature, and the solution was stirred at 80° C. for 17 hours and then cooled to room temperature to terminate the reaction. The reaction mixture was concentrated under reduced pressure to remove the solvent, and water was added to the concentrate, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/ methylene chloride=from 0% to 10%) and concentrated to afford the desired compound of formula 3-4 (0.255 g, 89.3%) as an orange oil.

Step 4: Synthesis of 4-(di(pyridin-2-yl)methyl)-N-(7-(hydroxyamino)-7-oxoheptyppiperazine-1-carboxamide (Compound 1222)

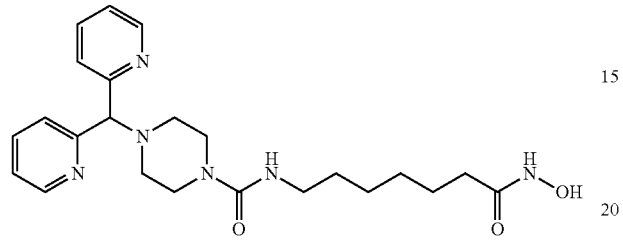
(Compound 1222)

The compound of formula 3-4 (0.255 g, 0.580 mmol) prepared in step 3, hydroxylamine (50.00% aqueous solution, 0.710 mL, 11.603 mmol) and potassium hydroxide (0.326 g, 5.801 mmol) were dissolved in methanol (3 mL) at room temperature, and the solution was stirred at the same temperature for 1 hour. The reaction mixture was concentrated under reduced pressure to remove the solvent, and the concentrate was purified by column chromatography (Waters, $C_{18}$; 1%-formic acid (methanoic acid) aqueous solution/acetonitrile aqueous solution=from 70% to 5%) and concentrated by passage through an SPE cartridge (PL-HCO$_3$ resin), thereby obtaining the desired compound 1222 (0.051 g, 20.0%) as a white solid.

$^1$H NMR (400 MHz, DMSO-d$_6$) δ 8.46 (dt, 2H, J=4.8, 0.8 Hz), 7.77 (td, 2H, J=7.7, 1.7 Hz), 7.62 (d, 2H, J=7.8 Hz), 7.25-7.22 (m, 2H), 6.40 (t, 1H, J=5.2 Hz), 4.64 (s, 1H), 3.28-3.27 (m, 4H), 2.96 (q, 2H, J=6.6 Hz), 2.25 (t, 4H, J=4.7 Hz), 1.92 (t, 2H, J=7.3 Hz), 1.48-1.43 (m, 2H), 1.35-1.33 (m, 2H), 1.21-1.20 (m, 4H).

EXAMPLE 11

Synthesis of Compound 1223

Step 1: Synthesis of tert-butyl 4-((7-methoxy-7-oxoheptyl)carbamoyl)piperazine-1-carboxylate (Formula 2-2)

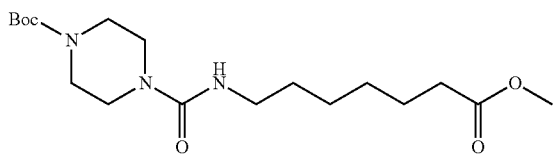
(2-2)

Triphosgene (4.780 g, 16.107 mmol) and diisopropylamine (16.879 mL, 96.644 mmol) were dissolved in methylene chloride (100 mL) at 0° C., and methyl 7-aminoheptanoate hydrochloride (6.304 g, 32.215 mmol) was added to the solution, followed by stirring at the same temperature. Tert-butyl piperazine-1-carboxylate (6.000 g, 32.215 mmol) was added to the reaction mixture, followed by stirring at the same time for 1 hour. Then, a saturated aqueous solution of sodium bicarbonate (100 mL) was added to the reaction mixture at 0° C., followed by stirring for 10 minutes. After completion of the reaction, water was added to the reaction mixture, followed by extraction with methylene chloride. The organic layer was washed with a saturated aqueous solution of sodium chloride, dried with anhydrous magnesium sulfate, filtered and then concentrated under reduced pressure. The concentrate was purified by column chromatography (SiO$_2$, 80 g cartridge; methanol/methylene chloride=from 0% to 5%) and concentrated to afford the desired compound of formula 2-2 (3.430 g, 28.7%) as a light yellow oil.

Step 2: Synthesis of methyl 7-(piperazine-1-carboxamido)heptanoate hydrochloride (Formula 2-5)

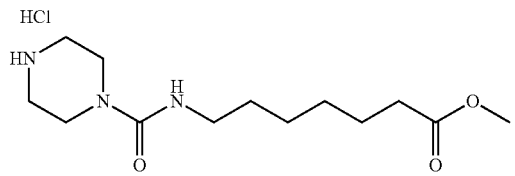
(2-5)

The compound of formula 2-2 (3.430 g, 9.233 mmol) prepared in step 1 was dissolved in methylene chloride (50 mL) at room temperature, and hydrochloric acid (4.00M dioxane solution, 11.542 mL, 46.167 mmol) was added to the solution, followed by stirring at the same temperature for 17 hours. The reaction mixture was concentrated under reduced pressure to remove the solvent, and ethyl acetate (50 mL) was added to the concentrate, followed by stirring. The precipitated solid was filtered, washed with ethyl acetate and dried to afford the desired compound of formula 2-5 (2.300 g, 80.9%) as a white solid.

Step 3: Synthesis of 4,4'-(chloromethylene)bis(fluorobenzene) (Formula 2-4)

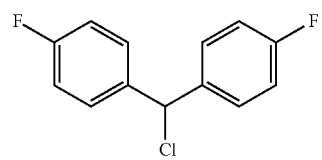
(2-4)

Bis(4-fluorophenyl)methanol (5.000 g, 22.706 mmol) was dissolved in methylene chloride (50 mL), and the solution was stirred at room temperature for 4 hours, and thionyl chloride (1.812 mL, 24.976 mmol) was added thereto. Then, the solution was stirred at 40° C. for 2 hours, and then cooled to room temperature to terminate the reaction. The reaction mixture was concentrated under reduced pressure to remove the solvent. As the product, the desired compound of formula 2-4 (5.350 g, 98.7%) was obtained as an orange oil and used without additional purification.

Step 4: Synthesis of methyl 7-(4-(bis(4-fluorophenyl)methyl)piperazine-1-carboxamido)heptanoate (Formula 2-6)

(2-6)

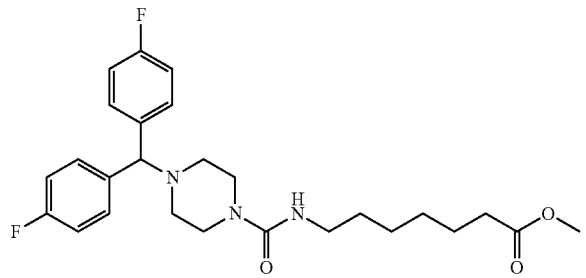

The compound of formula 2-4 (0.233 g, 0.975 mmol) prepared in step 3, methyl 7-(piperazine-1-carboxamido)heptanoate hydrochloride (0.200 g, 0.650 mmol) and potassium carbonate (0.449 g, 3.249 mmol) were dissolved in N,N-dimethylformamide (4 mL) at room temperature, and the solution was stirred at 80° C. for 17 hours, and then cooled to room temperature to terminate the reaction. The reaction mixture was concentrated under reduced pressure to remove the solvent, and water was added to the concentrate, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) and concentrated to afford the desired compound of formula 2-6 (0.101 g, 32.8%) as a light brown oil.

Step 5: Synthesis of 4-(bis(4-fluorophenyl)methyl)-N-(7-(hydroxyamino)-7-oxoheptyppiperazine-1-carboxamide (Compound 1223)

(Compound 1223)

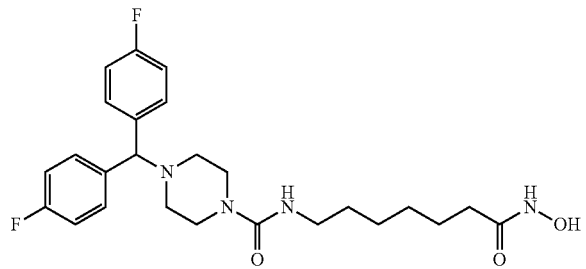

The compound of formula 2-6 (0.101 g, 0.213 mmol) prepared in step 4, hydroxylamine (50.00% aqueous solution, 0.261 mL, 4.266 mmol) and potassium hydroxide (0.120 g, 2.133 mmol) were dissolved in methanol (3 mL) at room temperature, and the solution was stirred at the same temperature for 1 hour. The reaction mixture was concentrated under reduced pressure to remove the solvent, and the concentrate was purified by column chromatography (Waters, C$_{18}$; 1%-formic acid (methanoic acid) aqueous solution/acetonitrile=from 70% to 5%) and concentrated by passage through an SPE cartridge (PL-HCO$_3$ resin) to afford the desired compound 1223 (0.002 g, 2.0%) as a white solid.

$^1$H NMR (400 MHz, CD$_3$OD) δ 7.48-7.44 (m, 4H), 7.04 (t, 4H, J=8.8 Hz), 6.44 (t, 1H, J=5.3 Hz), 4.31 (s, 1H), 3.39 (t, 4H, J=5.0 Hz), 3.16-3.12 (m, 2H), 2.36 (t, 4H, J=5.0 Hz), 2.09 (t, 2H, J=7.4 Hz), 1.64-1.61 (m, 2H), 1.51-1.48 (m, 2H), 1.35-1.33 (m, 4H); MS (ESI) m/z 475.3 (M$^+$+H).

EXAMPLE 12

Synthesis of Compound 1224

Step 1: Synthesis of 4,4'-(chloromethylene)bis(chlorobenzene) (Formula 2-4)

(2-4)

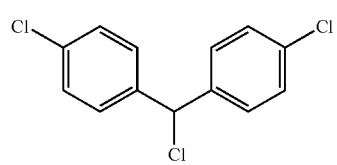

Bis(4-chlorophenyl)methanol (10.000 g, 39.507 mmol) was dissolved in methylene chloride (100 mL) at 0° C., and thionyl chloride (3.153 mL, 43.458 mmol) was added to the solution, followed by stirring at room temperature for 5 hours. The reaction mixture was concentrated under reduced pressure to remove the solvent. The desired compound of formula 2-4 (10.700 g, 99.7%) was obtained as a white solid without additional purification.

Step 2: Synthesis of methyl 7-(4-(bis(4-chlorophenyl)methyl)piperazine-1-carboxamido)heptanoate (Formula 2-6)

(2-6)

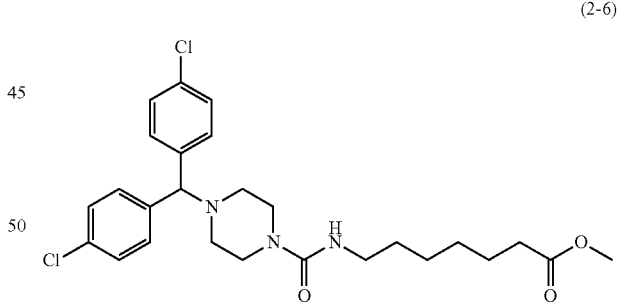

The compound of formula 2-4 (0.265 g, 0.975 mmol) prepared in step 1, the compound of formula 2-5 (0.200 g, 0.650 mmol) and potassium carbonate (0.449 g, 3.249 mmol) were dissolved in N,N-dimethylformamide (4 mL) at room temperature, and the solution was stirred at 80° C. for 17 hours, and then cooled to temperature to terminate the reaction. The reaction mixture was concentrated under reduced pressure to remove the solvent, and water was added to the concentrate, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) and concentrated to afford the desired compound of formula 2-6 (0.271 g, 82.4%) as a light yellow oil.

Step 3: Synthesis of 4-(bis(4-chlorophenyl)methyl)-N-(7-(hydroxyamino)-7-oxoheptyppiperazine-1-carboxamide (Compound 1224)

(Compound 1224)

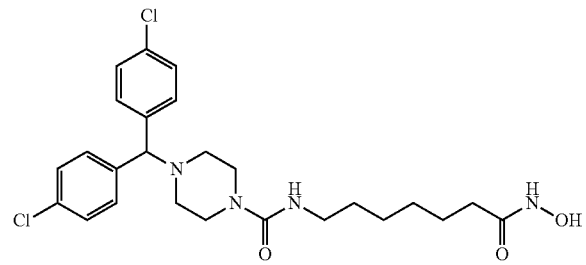

The compound of formula 2-6 (0.271 g, 0.535 mmol) prepared in step 2, hydroxylamine (50.00% aqueous solution, 0.655 mL, 10.702 mmol) and potassium hydroxide (0.300 g, 5.351 mmol) were dissolved in methanol (3 mL) at room temperature, and the solution was stirred at the same temperature for 1 hour. The reaction mixture was concentrated under reduced pressure to remove the solvent, and the concentrate was purified by column chromatography (Waters, C$_{18}$; 1%-formic acid (methanoic acid) aqueous solution/acetonitrile=from 70% to 5%) and concentrated by passage through an SPE cartridge (PL-HCO$_3$ resin) to afford the desired compound 1224 (0.035 g, 12.9%) as a white solid.

$^1$H NMR (400 MHz, DMSO-d$_6$) δ 10.34 (brs, 1H), 8.69 (brs, 1H), 7.43 (d, 4H, J=8.6 Hz), 7.37 (d, 4H, J=8.4 Hz), 6.41 (t, 1H, J=5.3 Hz), 4.40 (s, 1H), 3.28-3.27 (m, 4H), 2.96 (q, 2H, J=6.4 Hz), 2.22-2.21 (m, 4H), 1.92 (t, 2H, J=7.4 Hz), 1.48-1.44 (m, 2H), 1.37-1.35 (m, 2H), 1.24-1.21 (m, 4H); MS (ESI) m/z 507.4 (M$^+$+H).

EXAMPLE 13

Synthesis of Compound 1240

Step 1: Synthesis of methyl 8-(4-benzhydrylpiperazine-1-carboxyamido)octanoate (Formula 1-3)

(1-3)

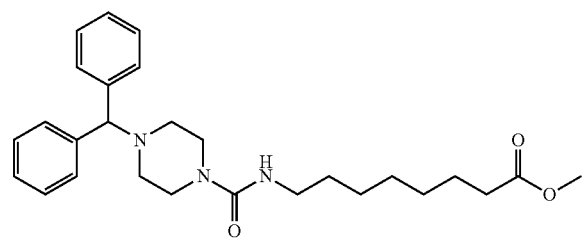

Triphosgene (0.118 g, 0.396 mmol) and diisopropylamine (0.830 mL, 4.755 mmol) were dissolved in methylene chloride (5 mL) at 0° C., and methyl 8-aminoctanoate hydrochloride (0.166 g, 0.793 mmol) was added to the solution, followed by stirring for 1 hour. A starting material (0.200 g, 0.793 mmol) was added to the reaction mixture, followed by stirring at the same temperature for 1 hour. A saturated aqueous solution of sodium bicarbonate was added to the reaction mixture, followed by extraction with methylene chloride. The extract was filtered through a plastic filter to remove the solid residue and the aqueous layer, and then concentrated under reduced pressure. The concentrate was purified by column chromatography (SiO$_2$, 4 g cartridge; ethyl acetate/hexane=from 10% to 70%) and concentrated to afford the desired compound of formula 1-3 (0.158 g, 44.1%) as a light yellow solid.

Step 2: Synthesis of 4-benzhydryl-N-(8-(hydroxyamino)-8-oxoethyl)piperazine-1-carboxamide (Compound 1240)

(Compound 1240)

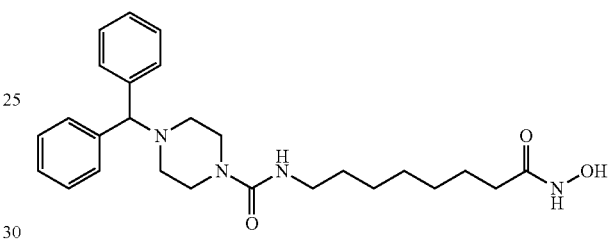

The compound of formula 1-3 (0.158 g, 0.350 mmol) prepared in step 1, hydroxylamine (50.00% aqueous solution, 0.428 mL, 6.997 mmol) and potassium hydroxide (0.196 g, 3.499 mmol) were dissolved in methanol (3 mL) at room temperature, and the solution was stirred at the same temperature for 30 minutes. The reaction mixture was concentrated under reduced pressure to remove the solvent, and a saturated aqueous solution of sodium bicarbonate (20 mL) was added to the concentrate, followed by stirring. The precipitated solid was filtered, washed with water and dried to afford the desired compound 1240 (0.074 g, 46.7%) as a white solid.

$^1$H NMR (400 MHz, DMSO-d$_6$) δ 9.49 (brs, 2H), 7.43 (d, 4H, J=7.5 Hz), 7.30 (t, 4H, J=7.6 Hz), 7.19 (t, 2H, J=7.3 Hz), 6.42 (t, 1H, J=5.2 Hz), 4.29 (s, 1H), 3.28-3.27 (m, 4H), 2.97 (q, 2H, J=6.4 Hz), 2.23-2.22 (m, 4H), 1.90 (t, 2H, J=7.3 Hz), 1.47-1.44 (m, 2H), 1.37-1.34 (m, 2H), 1.22 (brs, 4H); MS (ESI) m/z 453.6 (M$^+$+H).

EXAMPLE 14

Synthesis of Compound 1241

Step 1: Synthesis of methyl 7-(4-(1-phenylethyl)piperazine-1-carboxamido)heptanoate (Formula 9-2)

(9-2)

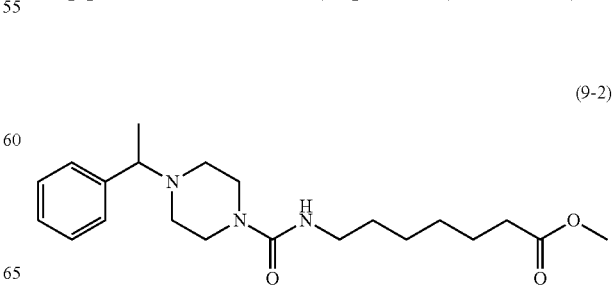

The compound of formula 2-5 (0.150 g, 0.553 mmol) and acetophenone (0.100 g, 0.829 mmol) were dissolved in methylene chloride (3 mL), and the solution was stirred at room temperature for 10 minutes. Then, NaBH(OAc)₃ (0.234 g, 1.106 mmol) was added to the solution, followed by stirring at the same temperature for 17 hours. A saturated aqueous solution of sodium bicarbonate was added to the reaction mixture, followed by extraction with methylene chloride. The extract was filtered through a plastic filter to remove the solid residue and the aqueous layer, and then concentrated under reduced pressure. The concentrate was purified by column chromatography (SiO₂, 4 g cartridge; methanol/methylene chloride=from 0% to 5%) and concentrated to afford the desired compound of formula 9-2 (0.038 g, 18.3%) as a colorless oil.

Step 2: Synthesis of N-(7-(hydroxyamino)-7-oxo-heptyl)-4-(1-phenylethyl)piperazine-1-carboxamide (Compound 1241)

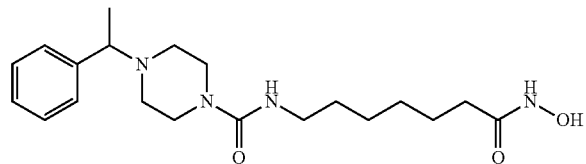

(Compound 1241)

The compound of formula 9-2 (0.038 g, 0.101 mmol) prepared in step 1, hydroxylamine (50.00% aqueous solution, 0.124 mL, 2.024 mmol) and potassium hydroxide (0.057 g, 1.012 mmol) were dissolved in methanol (3 mL) at room temperature, and the solution was stirred at the same temperature for 30 minutes. The reaction mixture was concentrated under reduced pressure to remove the solvent, and a saturated aqueous solution of sodium bicarbonate was added to the concentrate, followed by extraction with methylene chloride. The extract was filtered through a plastic filter to remove the solid residue and the aqueous layer, and then concentrated under reduced pressure. The desired compound 1241 (0.013 g, 34.1%) was obtained as a light orange solid without additional purification.

¹H NMR (400 MHz, DMSO-d₆) δ 7.32-7.30 (m, 4H), 7.26-7.23 (m, 1H), 3.71-3.34 (m, 5H), 3.11 (t, 2H, J=7.1 Hz), 2.50-2.45 (m, 2H), 2.37-2.32 (m, 2H), 2.05 (t, 2H, J=7.4 Hz), 1.61-1.56 (m, 2H), 1.49-1.44 (m, 2H), 1.37 (d, 3H, J=7.6 Hz), 1.33-1.29 (m, 4H); MS (ESI) m/z 477.2 (M⁺+H).

EXAMPLE 15

Synthesis of Compound 1243

Step 1: Synthesis of ethyl 1-(1-phenylethyl)piperidine-4-carboxylate (Formula 10-2)

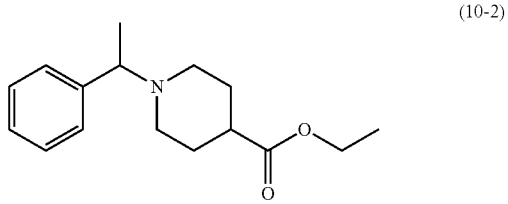 [SMILES: CCOC(=O)C1CCN(C(C)c2ccccc2)CC1]

(10-2)

Acetophenone (1.050 g, 8.739 mmol) and ethyl piperidine-4-carboxylate (1.751 mL, 11.361 mmol) were dissolved in methylene chloride (10 mL) at room temperature, and STAB (2.408 g, 11.361 mmol) was added to the solution, followed by stirring at the same temperature for 12 hours. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 12 g cartridge; ethyl acetate/hexane=from 0% to 50%) and concentrated to afford the desired compound of formula 10-2 (0.700 g, 30.6%) as a colorless oil.

Step 2: Synthesis of 1-(1-phenylethyl)piperidine-4-carboxylic acid (Formula 10-3)

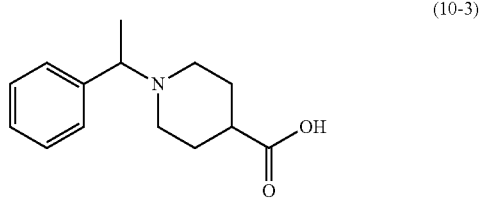 [SMILES: CC(c1ccccc1)N1CCC(C(=O)O)CC1]

(10-3)

The compound of formula 10-2 (0.700 g, 2.678 mmol) prepared in step 1 and LiOH (0.096 g, 4.017 mmol) were dissolved in methanol (3 mL)/water (1 mL) at 40° C., and the solution was stirred at the same temperature for 5 hours, and then cooled to room temperature. Then, 1 M HCl was added to the reaction mixture at 0° C., followed by stirring for 10 minutes. After completion of the reaction, water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The product (0.500 g, 69.2%, white foam solid) was used without additional purification.

Step 3: Synthesis of methyl 7-(1-(1-phenylethyl)piperidine-4-carboxamido)heptanoate (Formula 10-4)

(10-4)

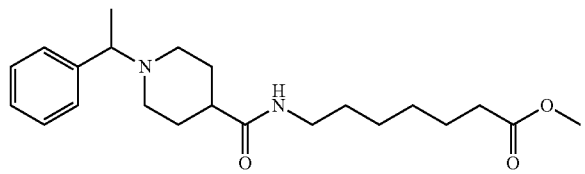

The compound of formula 10-3 (0.300 g, 1.286 mmol) prepared in step 2, methyl 7-aminoheptanoate hydrochloride (0.503 g, 2.572 mmol), EDC (0.493 g, 2.572 mmol), HOBt (0.347 g, 2.572 mmol) and diisopropylamine (1.123 mL, 6.429 mmol) were dissolved in methylene chloride (4 mL)/N,N-dimethylformamide (1 mL) at room temperature, and the solution was stirred at the same temperature for 17 hours. A saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 10%) and concentrated to afford the desired compound of formula 10-4 (0.122 g, 25.3%) as a brown oil.

Step 4: Synthesis of N-(7-(hydroxyamino)-7-oxoheptyl)-1-(1-phenylethyl)piperidine-4-carboxamide (Compound 1243)

(Compound 1243)

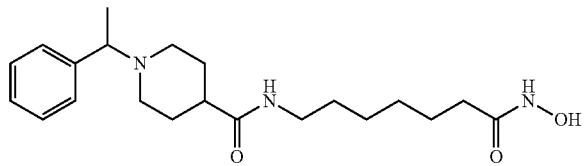

The compound of formula 10-4 (0.122 g, 0.326 mmol) prepared in step 3, hydroxylamine (50.00% aqueous solution, 0.398 mL, 6.515 mmol) and potassium hydroxide (0.183 g, 3.257 mmol) were dissolved in methanol (3 mL) at room temperature, and the solution was stirred at the same temperature for 30 minutes. The reaction mixture was concentrated under reduced pressure to remove the solvent, and a saturated aqueous solution of sodium bicarbonate was added to the concentrate, followed by extraction with methylene chloride. The extract was filtered through a plastic filter to remove the solid residue and the aqueous layer, and then concentrated under reduced pressure. The desired compound 1243 (0.074 g, 60.5%) was obtained as an orange solid without additional purification.

$^1$H NMR (400 MHz, DMSO-d$_6$) δ 10.19 (brs, 1H), 8.71 (brs, 1H), 7.64 (t, 1H, J=5.6 Hz), 7.32-7.27 (m, 4H), 7.23-7.20 (m, 1H), 3.40-3.37 (m, 1H), 3.00-2.95 (m, 3H); MS (ESI) m/z 376.3 (M$^+$+H).

EXAMPLE 16

Synthesis of Compound 1256

Step 1: Synthesis of methyl 7-(1-benzhydryl-N-methylpiperidine-4-carboxamido)heptanoate (Formula 5-5)

(5-5)

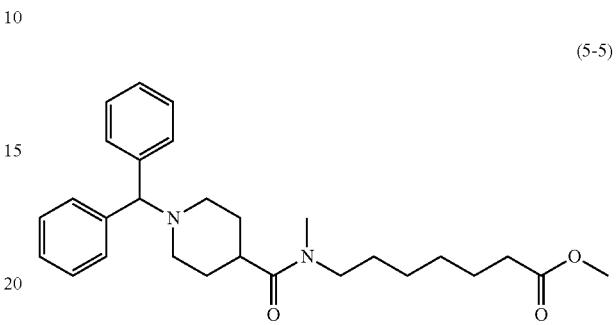

Methyl 7-(1-benzhydrylpiperidine-4-carboxamido)heptanoate (0.200 g, 0.458 mmol) and sodium hydride (60.00%, 0.092 g, 2.290 mmol) were dissolved in N,N-dimethylformamide (5 mL), and the solution was stirred at room temperature for 10 minutes. Then, iodomethane (0.143 mL, 2.290 mmol) was added to the stirred solution, followed by stirring at the same temperature for 17 hours. A saturated aqueous solution of sodium bicarbonate was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 10% to 70%) and concentrated to afford the desired compound of formula 5-5 (0.089 g, 43.1%) as a light yellow oil.

Step 2: Synthesis of 1-benzhydryl-N-(7-(hydroxyamino)-7-oxoheptyl)-N-methylpiperidine-4-carboxamide (Compound 1256)

(Compound 1256)

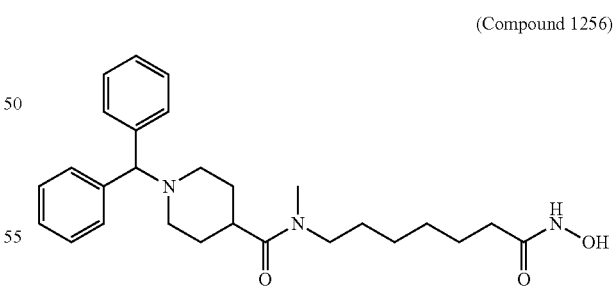

The compound of formula 5-5 (0.089 g, 0.198 mmol) prepared in step 1, hydroxylamine (50.00% aqueous solution, 0.242 mL, 3.950 mmol) and potassium hydroxide (0.111 g, 1.975 mmol) were dissolved in methanol (3 mL) at room temperature, and the solution was stirred at the same temperature for 1 hour. The reaction mixture was concentrated under reduced pressure to remove the solvent, and a saturated aqueous solution of sodium bicarbonate was added to the concentrate, followed by extraction with methylene chloride. The extract was filtered through a plastic filter to remove the solid residue and the aqueous layer, and then concentrated under reduced pressure. The desired compound 1256 (0.089 g, 99.8%) was obtained as a white solid without additional purification.

$^1$H NMR (400 MHz, DMSO-$d_6$) δ 9.50 (brs, 2H), 7.40 (d, 4H, J=7.2 Hz), 7.29 (t, 4H, J=7.6 Hz), 7.18 (t, 2H, J=7.3 Hz), 4.30 (s, 1H), 3.23 (q, 2H, J=7.5 Hz), 2.94 (s, 2H), 2.81 (d, 2H, J=11.4 Hz), 2.76 (s, 1H), 1.91-1.83 (m, 4H), 1.69-1.53 (m, 4H), 1.46-1.37 (m, 4H), 1.24-1.19 (m, 4H); MS (ESI) m/z 452.6 (M$^+$+H).

EXAMPLE 17

Synthesis of Compound 1257

Step 1: Synthesis of methyl 6-(4-benzhydrylpiperazine-1-carboxamido)hexanoate (Formula 1-3)

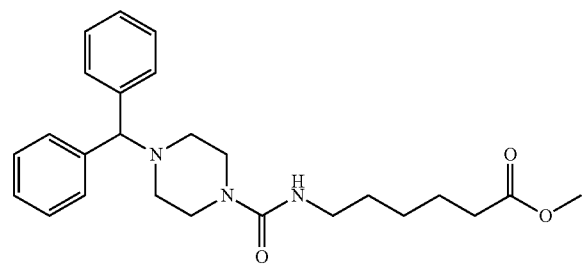

(1-3)

Triphosgene (0.294 g, 0.991 mmol) and diisopropylamine (2.076 mL, 11.888 mmol) were dissolved in methylene chloride (10 mL) at 0° C., and methyl 6-aminohexanoate hydrochloride (0.360 g, 1.981 mmol) was added to the solution, followed by stirring at the same temperature. 1-Benzhydrylpiperazine (0.500 g, 1.981 mmol) was added to the reaction mixture, followed by stirring at the same temperature for 1 hour. A saturated aqueous solution of sodium bicarbonate was added to the reaction mixture, followed by extraction with methylene chloride. The extract was filtered through a plastic filter to remove the solid residue and the aqueous layer, and then concentrated under reduced pressure. The concentrate was purified by column chromatography (SiO$_2$, 12 g cartridge; ethyl acetate/hexane=from 0% to 40%) and concentrated to afford the desired compound of formula 1-3 (0.320 g, 38.1%) as a yellow oil.

Step 2: Synthesis of 4-benzhydryl-N-(6-(hydroxyamino)-6-oxohexyl)piperazine-1-carboxamide (Compound 1257)

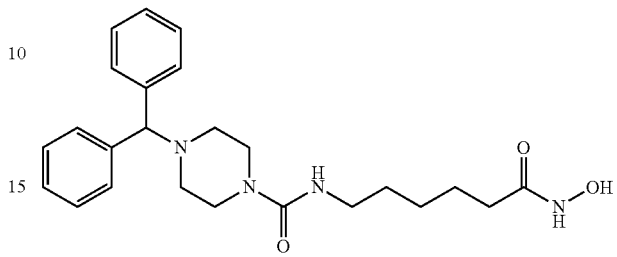

(Compound 1257)

The compound of formula 1-3 (0.200 g, 0.472 mmol) prepared in step 1, hydroxylamine (50.00% aqueous solution, 0.578 mL, 9.444 mmol) and potassium hydroxide (0.265 g, 4.722 mmol) were dissolved in methanol (5 mL) at room temperature, and the solution was stirred at the same temperature for 1 hour. The reaction mixture was concentrated under reduced pressure to remove the solvent, and a saturated aqueous solution of sodium bicarbonate was added to the concentrate, followed by extraction with methylene chloride. The extract was filtered through a plastic filter to remove the solid residue and the aqueous layer, and then concentrated under reduced pressure. The desired compound 1257 (0.049 g, 24.4%) was obtained as a light yellow solid without additional purification.

$^1$H NMR (400 MHz, DMSO-$d_6$) δ 7.43 (d, 4H, J=7.2 Hz), 7.30 (t, 4H, J=7.6 Hz), 7.19 (t, 2H, J=7.3 Hz), 6.42 (t, 1H, J=5.4 Hz), 4.29 (s, 1H), 3.27 (t, 4H, J=4.5 Hz), 2.96 (q, 2H, J=6.4 Hz), 2.23 (t, 4H, J=4.6 Hz), 1.90 (t, 2H, J=7.4 Hz), 1.47-1.44 (m, 2H), 1.38-1.34 (m, 2H), 1.20-1.16 (m, 2H); MS (ESI) m/z 425.5 (M$^+$+H).

EXAMPLE 18

Synthesis of Compound 1316

Step 1: Synthesis of methyl 6-(1-benzhydrylpiperidine-4-carboxamido)hexanoate (Formula 5-4)

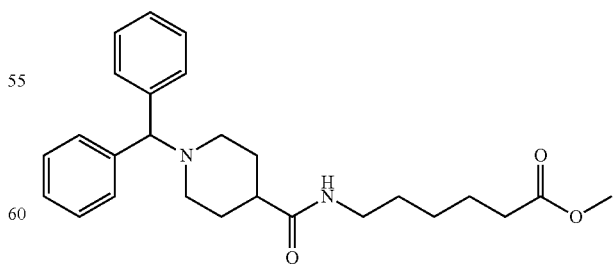

(5-4)

The compound of formula 5-3 (0.300 g, 1.016 mmol), methyl 6-aminohexanoate hydrochloride (0.369 g, 2.031 mmol), EDC (0.389 g, 2.031 mmol), HOBt (0.274 g, 2.031 mmol) and diisopropylamine (0.887 mL, 5.078 mmol) were dissolved in methylene chloride (3 mL)/N,N-dimethylformamide (0.5 mL) at room temperature, and the solution was stirred at the same temperature for 17 hours. A saturated aqueous solution of sodium bicarbonate was added to the reaction mixture, followed by extraction with ethyl acetate. The organic layer was washed with a saturated aqueous solution of sodium chloride, dried with anhydrous magnesium sulfate, filtered and then concentrated under reduced pressure. The concentrate was purified by column chromatography (SiO$_2$, 12 g cartridge; ethyl acetate/hexane=from 0% to 30%) and concentrated to afford the desired compound of formula 5-4 (0.161 g, 37.5%) as a light yellow oil.

Step 2: Synthesis of 1-benzhydryl-N-(6-(hydroxyamino)-6-oxohexyl)piperidine-4-carboxamide (Compound 1316)

(Compound 1316)

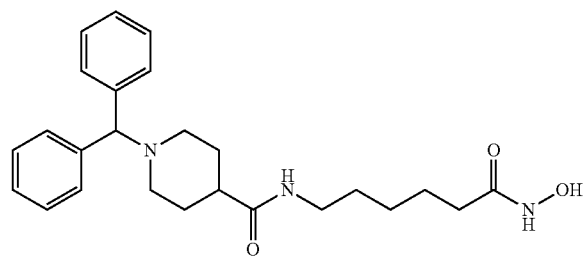

The compound of formula 5-4 (0.161 g, 0.381 mmol) prepared in step 1, hydroxylamine (50.00% aqueous solution, 0.466 mL, 7.620 mmol) and potassium hydroxide (0.214 g, 3.810 mmol) were dissolved in methanol (3 mL) at room temperature, and the solution was stirred at the same temperature for 1 hour. The reaction mixture was concentrated under reduced pressure to remove the solvent, and a saturated aqueous solution of sodium bicarbonate was added to the concentrate, followed by extraction with methylene chloride. The organic layer was washed with a saturated aqueous solution of sodium chloride, dried with anhydrous magnesium sulfate, filtered and then concentrated under reduced pressure. The desired compound 1316 (0.056 g, 34.7%) was obtained as a white solid without additional purification.

$^1$H NMR (400 MHz, DMSO-d$_6$) δ 10.33 (brs, 1H), 8.66 (brs, 1H), 7.70 (t, 1H, J=5.6 Hz), 7.41 (d, 4H, J=7.4 Hz), 7.17 (t, 2H, J=7.4 Hz), 4.26 (s, 2H), 2.99~2.28 (m, 2H), 2.80 (d, 2H, J=11.5 Hz), 2.09~2.02 (m, 1H), 1.91 (t, 2H, J=7.5 Hz), 1.80~1.75 (m, 2H), 1.68~1.59 (m, 4H).

EXAMPLE 19

Synthesis of Compound 1317

Step 1: Synthesis of methyl 8-(1-benzhydrylpiperidine-4-carboxamido)octanoate (Formula 5-4)

(5-4)

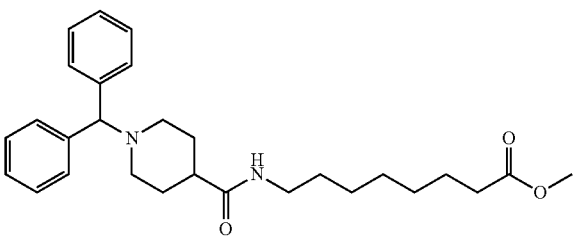

The compound of formula 5-3 (0.300 g, 1.016 mmol), methyl 8-aminooctanoate hydrochloride (0.426 g, 2.031 mmol), EDC (0.389 g, 2.031 mmol), HOBt (0.274 g, 2.031 mmol) and diisopropylamine (0.887 mL, 5.078 mmol) were dissolved in methylene chloride (3 mL)/N,N-dimethylformamide (0.5 mL) at room temperature, and the solution was stirred at the same temperature for 17 hours. A saturated aqueous solution of sodium bicarbonate was added to the reaction mixture, followed by extraction with ethyl acetate. The organic layer was washed with a saturated aqueous solution of sodium chloride, dried with anhydrous magnesium sulfate, filtered and then concentrated under reduced pressure. The concentrate was purified by column chromatography (SiO$_2$, 12 g cartridge; ethyl acetate/hexane=from 0% to 30%) and concentrated to afford to the desired compound of formula 5-4 (0.220 g, 49.6%) as a colorless oil.

Step 2: Synthesis of 1-benzhydryl-N-(8-(hydroxyamino)-8-oxoethyl)piperidine-4-carboxamide (Compound 1317)

(Compound 1317)

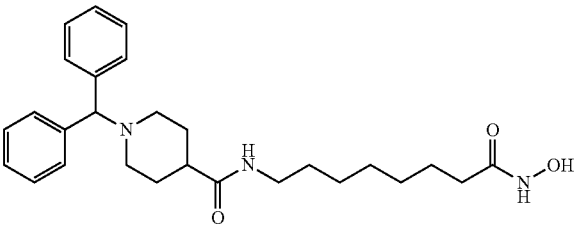

The compound of formula 5-4 (0.220 g, 0.488 mmol) prepared in step 1, hydroxylamine (50.00% aqueous solution, 0.597 mL, 9.764 mmol) and potassium hydroxide (0.274 g, 4.882 mmol) were dissolved in methanol (5 mL) at room temperature, and the solution was stirred at the same temperature for 1 hour. The reaction mixture was concentrated under reduced pressure to remove the solvent, and a saturated aqueous solution of sodium bicarbonate (20 mL) was added to the concentrate, followed by stirring. The precipitated solid was filtered, washed with water and dried to afford the desired compound 1317 (0.189 g, 85.7%) as a white solid.

¹H NMR (400 MHz, DMSO-d₆) δ 9.46 (brs, 2H), 7.73 (t, 1H, J=5.3 Hz), 7.41 (d, 4H, J=8.0 Hz), 7.28 (t, 4H, J=7.5 Hz), 7.17 (t, 2H, J=7.3 Hz), 4.26 (s, 1H), 2.99 (q, 2H, J=6.4 Hz), 2.80 (d, 2H, J=11.1 Hz), 2.10-2.04 (m, 1H), 1.87 (t, 2H, J=7.3 Hz), 1.78 (t, 2H, J=10.0 Hz), 1.67-1.56 (m, 4H), 1.46-1.42 (m, 2H), 1.36-1.33 (m, 2H), 1.21 (brs, 6H).

EXAMPLE 20

Synthesis of Compound 1647

Step 1: Synthesis of 2,2'-(chloromethylene)bis(fluorobenzene) (Formula 2-4)

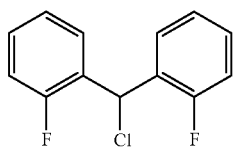

(2-4)

Bis(2-fluorophenyl)methanol (0.500 g, 2.270 mmol) and triethylamine (0.348 mL, 2.498 mmol) were dissolved in methylene chloride (5 mL) at room temperature, and methanesulfonyl chloride (0.193 mL, 2.498 mmol) was added to the solution, followed by stirring at the same temperature for 18 hours. Water was added to the reaction mixture, followed by extraction with methylene chloride. The extract was filtered through a plastic filter to remove the solid residue and the aqueous layer, and then concentrated under reduced pressure. The concentrate was purified by column chromatography (SiO₂, 12 g cartridge; ethyl acetate/hexane=from 0% to 5%) and concentrated to afford the desired compound of formula 2-4 (0.290 g, 53.5%) as a colorless oil.

Step 2: Synthesis of methyl 7-(4-(bis(2-fluorophenyl)methyl)piperazine-1-carboxamido)heptanoate (Formula 2-6)

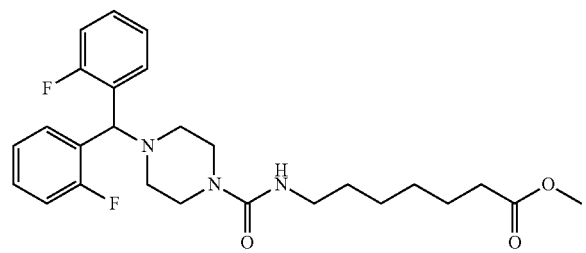

(2-6)

The compound of formula 2-4 (0.448 g, 1.877 mmol) prepared in step 1, methyl 7-(piperazin-1-yl)heptanoate hydrochloride (0.746 g, 2.816 mmol) and potassium carbonate (1.297 g, 9.386 mmol) were dissolved in N,N-dimethylformamide (8 mL) at 80° C., and the solution was stirred at the same temperature for 16 hours, and then cooled to room temperature to terminate the reaction. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO₂, 12 g cartridge; ethyl acetate/hexane=from 0% to 60%) and concentrated to afford the desired compound of formula 2-6 (0.170 g, 19.1%) as a bright yellow solid.

Step 3: Synthesis of 4-(bis(2-fluorophenyl)methyl)-N-(7-(hydroxyamino)-7-oxoheptyl)piperazine-1-carboxamide (Compound 1647)

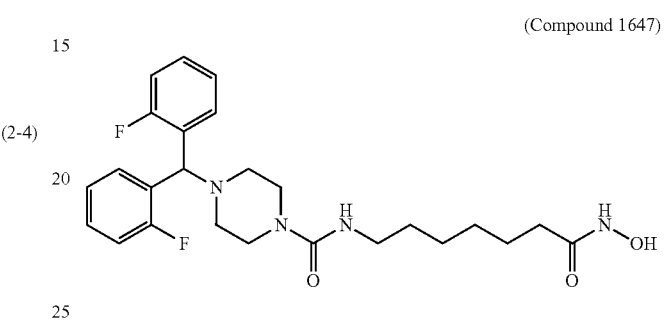

(Compound 1647)

The compound of formula 2-6 (0.200 g, 0.422 mmol) prepared in step 2 and hydroxylamine (50.00% aqueous solution, 0.258 mL, 4.223 mmol) were dissolved in methanol (5 mL) at 0° C., and the solution was stirred at room temperature for 3 hours. The reaction mixture was concentrated under reduced pressure to remove the solvent, and methanol (10 mL) and a saturated aqueous solution of sodium bicarbonate (90 mL) were added to the concentrate, followed by stirring. The precipitated solid was filtered, washed with water and dried to afford the desired compound 1647 (0.200 g, 99.8%) as a white solid.

¹H NMR (400 MHz, DMSO-d₆) δ 7.59-7.55 (m, 2H), 7.31-7.26 (m, 2H), 7.23-7.19 (m, 2H), 7.16-7.11 (m, 2H), 6.42 (t, 1H, J=5.5 Hz), 4.96 (s, 1H), 3.29-3.28 (m, 4H), 2.99-2.94 (m, 2H), 2.28-2.26 (m, 4H), 1.93-1.89 (m, 2H), 1.47-1.43 (m, 2H), 1.37-1.33 (m, 2H), 1.19-1.20 (m, 4H); MS (ESI) m/z 475.4 (M⁺+H).

EXAMPLE 21

Synthesis of Compound 1648

Step 1: Synthesis of 3,3'-(chloromethylene)bis(fluorobenzene) (Formula 2-4)

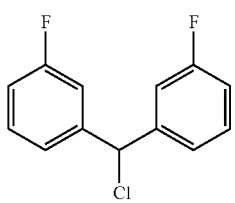

(2-4)

Bis(3-fluorophenyl)methanol (1.000 g, 4.541 mmol) and triethylamine (0.696 mL, 4.995 mmol) were dissolved in methylene chloride (10 mL), and methanesulfonyl chloride (0.387 mL, 4.995 mmol) was added to the solution, followed by stirring at the same temperature for 18 hours. Water was added to the reaction mixture, followed by extraction with methylene chloride. The extract was filtered through a plastic filter to remove the solid residue and the aqueous layer, and then concentrated under reduced pressure. The concentrate was purified by column chromatography (SiO$_2$, 12 g cartridge; ethyl acetate/hexane=from 0% to 5%) and concentrated to afford the desired compound of formula 2-4 (0.670 g, 61.8%) as a colorless oil.

Step 2: Synthesis of 7-(4-(bis(3-fluorophenyl)methyl)piperazine-1-carboxamido)heptanoate (Formula 2-6)

(2-6)

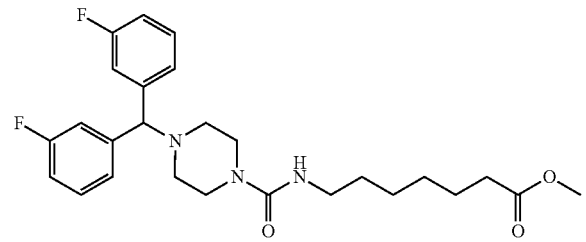

The compound of formula 2-4 (0.670 g, 2.807 mmol) prepared in step 1, methyl 7-(piperazin-1-yl)heptanoate hydrochloride (1.115 g, 4.211 mmol) and potassium carbonate (1.940 g, 14.037 mmol) were dissolved in N,N-dimethylformamide (10 mL) at 80° C., and the solution was stirred at the same temperature for 16 hours, and then cooled to room temperature to terminate the reaction. Water was added to the reaction mixture, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 24 g cartridge; ethyl acetate/hexane=from 0% to 50%) and concentrated to afford the desired compound of formula 2-6 (0.294 g, 22.1%) as a white solid.

Step 3: Synthesis of 4-(bis(3-fluorophenyl)methyl)-N-(7-(hydroxyamino)-7-oxoheptyppiperazine-1-carboxamide (Compound 1648)

(Compound 1648)

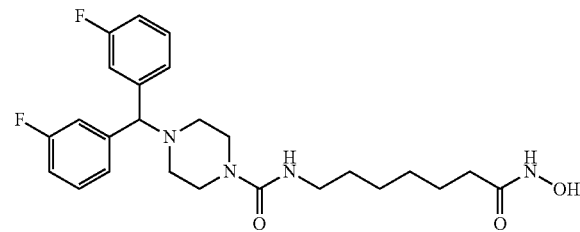

The compound of formula 2-6 (0.100 g, 0.211 mmol) prepared in step 2 and hydroxylamine (50.00% aqueous solution, 0.129 mL, 2.112 mmol) were dissolved in methanol (3 mL) at 0° C., and the solution was stirred at room temperature for 3 hours. The reaction mixture was concentrated under reduced pressure to remove the solvent, and methanol (10 mL) and a saturated aqueous solution of sodium bicarbonate (90 mL) were added to the concentrate, followed by stirring. The precipitated solid was filtered, washed with water and dried to afford the desired compound 1648 (0.097 g, 97.1%) as a white solid.

$^1$H NMR (400 MHz, DMSO-d$_6$) δ 10.34 (s, 1H), 8.72 (s, 1H), 7.38-7.33 (m, 2H), 7.28-7.25 (m, 4H), 7.06-7.01 (m, 2H), 6.40 (t, 1H, J=5.5 Hz), 4.41 (s, 1H), 3.29-3.27 (m, 4H), 2.99-2.94 (m, 2H), 2.24-2.22 (m, 4H), 1.93-1.90 (m, 2H), 1.47-1.44 (m, 2H), 1.37-1.33 (m, 2H), 1.21-1.20 (m, 4H); MS (ESI) m/z 475.4 (M$^+$+H).

EXAMPLE 22

Synthesis of Compound 1649

Step 1: Synthesis of methyl 7-(4-(hydroxydiphenylmethyl)piperidine-1-carboxamido)heptanoate (Formula 7-4)

(7-4)

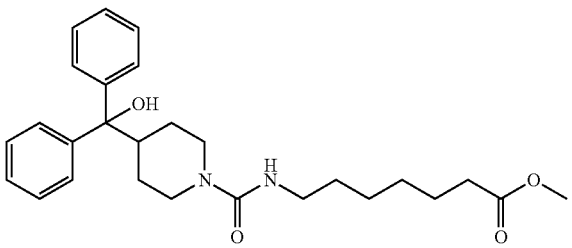

Methyl 7-aminoheptanoate hydrochloride (0.366 g, 1.870 mmol) and triphosgene (0.277 g, 0.935 mmol) were dissolved in methylene chloride (10 mL) at 0° C., and N,N-diisopropylethylamine (0.977 mL, 5.610 mmol) was added to the solution, followed by stirring for 1 hour. Diphenyl(piperidin-4-yl)methanol (0.500 g, 1.870 mmol) was added to the reaction mixture, followed by stirring at the same temperature for 1 hour. Water was added to the reaction mixture, followed by extraction with methylene chloride. The extract was filtered through a plastic filter to remove the solid residue and the aqueous layer, and then concentrated under reduced pressure. The concentrate was purified by column chromatography (SiO$_2$, 12 g cartridge; ethyl acetate/hexane=from 0% to 50%) and concentrated to afford the desired compound of formula 7-4 (0.609 g, 71.9%) as a colorless oil.

Step 2: Synthesis of methyl 7-(4-(fluorodiphenylmethyl)piperidine-1-carboxamido)heptanoate (Formula 7-5)

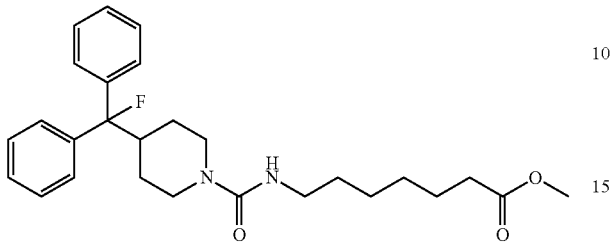

(7-5)

The compound of formula 7-4 (0.300 g, 0.663 mmol) prepared in step 1 was dissolved in methylene chloride (5 mL) at 0° C., and diethylaminosulfur trifluoride (DAST, 0.114 mL, 0.862 mmol) was added to the solution, followed by stirring at room temperature for 16 hours. Water was added to the reaction mixture, followed by extraction with methylene chloride. The extract was filtered through a plastic filter to remove the solid residue and the aqueous layer, and then concentrated under reduced pressure. The concentrate was purified by column chromatography (Sift, 12 g cartridge; ethyl acetate/hexane=from 0% to 50%) and concentrated to afford the desired compound of formula 7-5 (0.143 g, 47.5%) as a white solid.

Step 3: Synthesis of 4-(fluorodiphenylmethyl)-N-(7-(hydroxyamino)-7-oxoheptyl)piperidine-1-carboxamide (Compound 1649)

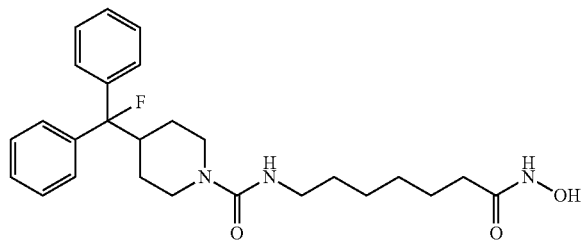

(Compound 1649)

The compound of formula 7-5 (0.140 g, 0.308 mmol) prepared in step 2 and hydroxylamine (50.00% aqueous solution, 0.188 mL, 3.080 mmol) was dissolved in methanol (3 mL) at 0° C., and the solution was stirred at room temperature for 3 hours. The reaction mixture was concentrated under reduced pressure to remove the solvent, and methanol (10 mL) and a saturated aqueous solution of sodium bicarbonate (90 mL) were added to the concentrate, followed by stirring. The precipitated solid was filtered, washed with water and dried to afford the desired compound 1649 (0.122 g, 87.0%) as a white solid.

$^1$H NMR (400 MHz, DMSO-$d_6$) δ 7.49-7.47 (m, 4H), 7.37-7.33 (m, 4H), 7.26-7.22 (m, 2H), 6.36 (t, 1H, J=5.5 Hz), 3.95-3.92 (m, 2H), 2.98-2.79 (m, 3H), 2.65-2.59 (m, 2H), 1.93-1.89 (m, 2H), 1.47-1.44 (m, 2H), 1.36-1.33 (m, 2H), 1.29-1.20 (m, 8H); MS (ESI) m/z 456.6 (M$^+$+H).

EXAMPLE 23

Synthesis of Compound 1719

Step 1: Synthesis of tert-butyl 4-(phenylamino)piperidine-1-carboxylate (Formula 6-2)

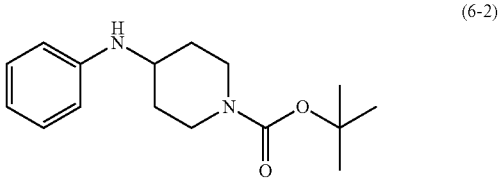 [SMILES: CC(C)(C)OC(=O)N1CCC(Nc2ccccc2)CC1]

(6-2)

Tert-butyl 4-oxopiperidine-1-carboxylate (5.000 g, 25.094 mmol), aniline (2.749 mL, 30.113 mmol) and acetic acid (2.155 mL, 37.641 mmol) were dissolved in methylene chloride (50 mL) at room temperature, and sodium triacetoxyborohydride (5.850 g, 27.604 mmol) was added to the solution, followed by stirring at the same temperature for 16 hours. A saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. Ethyl acetate (100 mL) was added to the concentrate, followed by stirring. The precipitated solid was filtered, washed with hexane and dried to afford the desired compound of formula 6-2 (4.640 g, 66.9%) as a white solid.

Step 2: Synthesis of tert-butyl 4-((3-fluorophenyl)(phenyl)amino)piperidine-1-carboxylate (Formula 6-3)

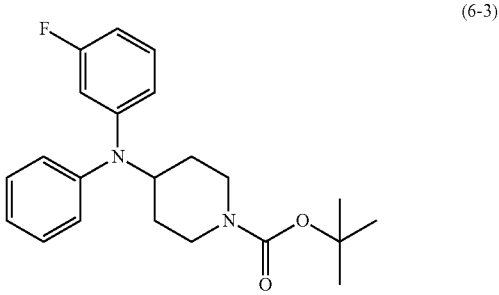 [SMILES: CC(C)(C)OC(=O)N1CCC(N(c2ccccc2)c2cccc(F)c2)CC1]

(6-3)

The compound of formula 6-2 (0.500 g, 1.809 mmol) prepared in step 1, 1-fluoro-3-iodobenzene (0.422 g, 1.900 mmol), palladium acetate (II, 0.016 g, 0.072 mmol), 2,2'-bis(diphenylphosphino)-1,1'-binaphthyl (0.051 g, 0.081 mmol) and potassium tert-butoxide (0.254 g, 2.261 mmol) were dissolved in toluene (5 mL) at 110° C., and the solution was stirred at the same temperature for 16 hours, and then cooled to room temperature to terminate the reaction. The reaction mixture was filtered through a celite pad to remove solids, and a saturated aqueous solution of sodium chloride was added to the filtrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 10%) and concentrated to afford the desired compound of formula 6-3 (0.292 g, 43.6%) as a yellow solid.

Step 3: Synthesis of N-(3-fluorophenyl)-N-phenylpiperidine-4-amine hydrochloride (Formula 6-4)

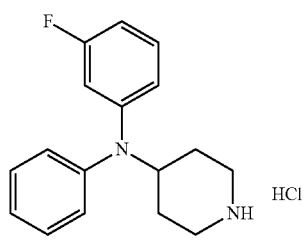

(6-4)

The compound of formula 6-3 (0.285 g, 0.769 mmol) prepared in step 2 was dissolved in methylene chloride (10 mL) at the same temperature, and hydrogen chloride (4.00 M solution in dioxane, 0.962 mL, 3.846 mmol) was added to the solution, followed by stirring at the same temperature for 16 hours. The reaction mixture was concentrated under reduced pressure to remove the solvent. The product (0.212 g, 89.8%, yellow solid) was used without additional purification.

Step 4: Synthesis of methyl 7-(4-((3-fluorophenyl)(phenyl)amino)piperidine-1-carboxamido)heptanoate (Formula 6-6)

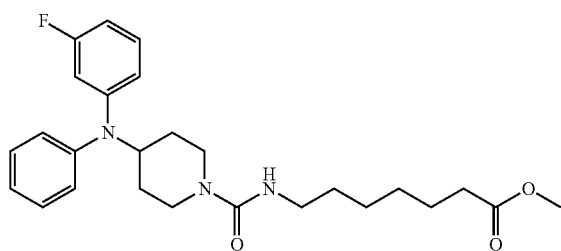

(6-6)

Methyl 7-aminoheptanoate hydrochloride (0.135 g, 0.691 mmol) and triphosgene (0.103 g, 0.345 mmol) were dissolved in methylene chloride (10 mL) at 0° C., and N,N-diisopropylethylamine (0.361 mL, 2.073 mmol) was added to the solution, followed by stirring at the same temperature. To the reaction mixture, the compound of formula 6-4 (0.212 g, 0.691 mmol) prepared in step 3 was added, followed by stirring at room temperature for 3 hours. Then, a saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) and concentrated to afford the desired compound of formula 6-6 (0.219 g, 69.6%) as a colorless oil.

Step 5: Synthesis of 4-((3-fluorophenyl)(phenyl)amino)-N-(7-(hydroxyamino)-7-oxoheptyl)piperidine-1-carboxamide (compound 1719)

(Compound 1719)

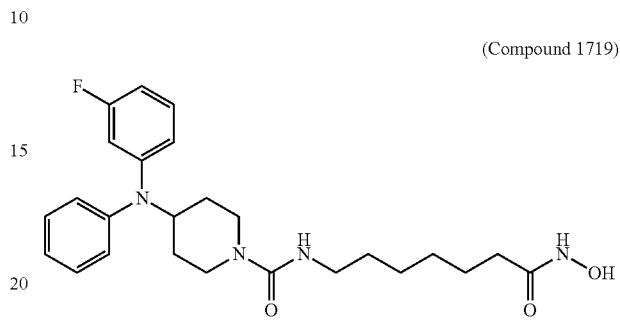

The compound of formula 6-6 (0.219 g, 0.481 mmol) prepared in step 4, hydroxylamine (50.00% aqueous solution, 0.294 mL, 4.807 mmol) and potassium hydroxide (0.270 g, 4.807 mmol) were dissolved in methanol (5 mL) at 0° C., and the solution was stirred at room temperature for 3 hours. The reaction mixture was concentrated under reduced pressure to remove the solvent, and methanol (1 mL) and a saturated aqueous solution of sodium bicarbonate (30 mL) were added to the concentrate, followed by stirring. The precipitated solid was filtered, washed with hexane and dried to afford the desired compound 1719 (0.196 g, 89.3%) as a white solid.

$^1$H NMR (400 MHz, DMSO-d$_6$) δ 7.44-7.42 (m, 2H), 7.32-7.28 (m, 1H), 7.16-7.10 (m, 1H), 7.05-7.03 (m, 2H), 6.51-6.46 (m, 1H), 6.37-6.32 (m, 3H), 4.10-4.08 (m, 1H), 3.97-3.94 (m, 2H), 2.92-2.87 (m, 2H), 2.83-2.77 (m, 2H), 1.92-1.88 (m, 2H), 1.85-1.52 (m, 2H), 1.45-1.41 (m, 2H), 1.30-1.27 (m, 2H), 1.16-1.08 (m, 4H), 1.06-1.00 (m, 2H); MS (ESI) m/z 457.5 (M$^+$+H).

EXAMPLE 24

Synthesis of Compound 1726

Step 1: Synthesis of tert-butyl 4-(phenyl(4-(trifluoromethyl)phenyl)amino)piperidine-1-carboxylate (Formula 6-3)

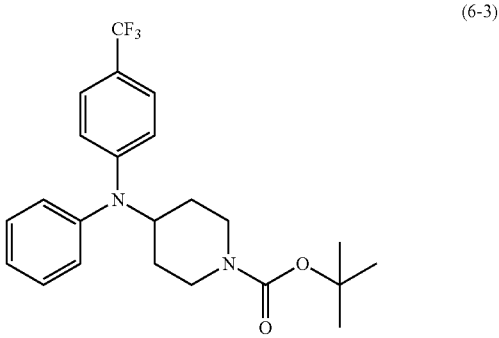 [SMILES: CC(C)(C)OC(=O)N1CCC(N(c2ccccc2)c2ccc(C(F)(F)F)cc2)CC1]

(6-3)

Tert-butyl 4-(phenylamino)piperidine-1-carboxylate (1.000 g, 3.618 mmol), 1-iodo-4-(trifluoromethyl)benzene (1.033 g, 3.799 mmol), palladium acetate (II, 0.032 g, 0.145 mmol), 2,2'-bis(diphenylphosphino)-1,1'-binaphthyl (0.101 g, 0.163 mmol) and potassium tert-butoxide (0.507 g, 4.523 mmol) were dissolved in toluene (5 mL) at 110° C., and the solution was stirred at the same temperature for 16 hours, and then cooled to room temperature to terminate the reaction. The reaction mixture was filtered through a celite pad to remove solids, and water was added to the filtrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 10%) and concentrated to afford the desired compound of formula 6-3 (0.040 g, 2.9%) as a brown oil.

Step 2: Synthesis of N-phenyl-N-(4-(trifluoromethyl)phenyl)piperidine-4-amine hydrochloride (Formula 6-4)

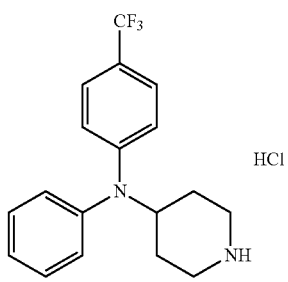

(6-4)

The compound of formula 6-3 (0.890 g, 2.494 mmol) prepared in step 1 was dissolved in methylene chloride (20 mL) at room temperature, and hydrochloric acid (4.00 M solution, 3.118 mL, 12.471 mmol) was added to the solution, followed by stirring at the same temperature for 16 hours. The reaction mixture was concentrated under reduced pressure to remove the solvent. The product (0.890 g, 100.0%, yellow solid) was used without additional purification.

Step 3: Synthesis of methyl 7-(4-(phenyl(4-(trifluoromethyl)phenyl)amino)piperidine-1-carboxamido) heptanoate (Formula 6-6)

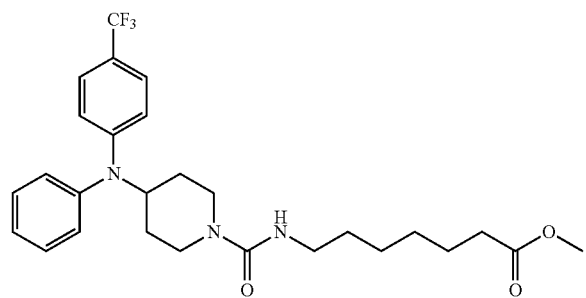

(6-6)

Methyl 7-aminoheptanoate hydrochloride (0.219 g, 1.121 mmol) and triphosgene (0.166 g, 0.561 mmol) were dissolved in methylene chloride (10 mL) at 0° C., and N,N-diisopropylethylamine (0.586 mL, 3.363 mmol) was added to the solution, followed by stirring at the same temperature. To the reaction mixture, the compound of formula 6-4 (0.400 g, 1.121 mmol) was added, followed by stirring at room temperature for 3 hours. A saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 50%) and concentrated to afford the desired compound of formula 6-6 (0.277 g, 48.9%) as a colorless oil.

Step 4: Synthesis of N-(7-(hydroxyamino)-7-oxo-heptyl)-4-(phenyl(4-(trifluoromethyl)phenyl)amino) piperidine-1-carboxamie (Compound 1726)

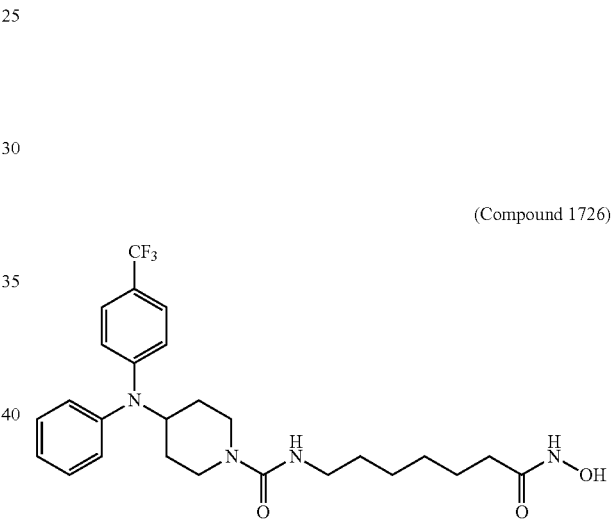

(Compound 1726)

The compound of formula 6-6 (0.170 g, 0.336 mmol) prepared in step 3 and hydroxylamine (50.00% aqueous solution, 0.205 mL, 3.356 mmol) were dissolved in methanol (5 mL) at room temperature, and potassium hydroxide (0.188 g, 3.356 mmol) was added to the solution, followed by stirring at the same temperature for 18 hours. The reaction mixture was concentrated under reduced pressure to remove the solvent, and the precipitated solid was filtered, washed with hexane and dried to afford the desired compound 1726 (0.139 g, 81.8%) as a white solid.

$^1$H NMR (400 MHz, DMSO-d$_6$) δ 10.33 (s, 1H), 8.66 (s, 1H), 7.21-7.16 (m, 4H), 6.97-6.93 (m, 2H), 6.84-6.80 (m, 1H), 6.67-6.65 (m, 2H), 6.36-6.34 (m, 1H), 4.07-4.02 (m, 1H), 3.98-3.95 (m, 2H), 2.93-2.88 (m, 2H), 2.81-2.75 (m, 2H), 1.93-1.89 (m, 2H), 1.85-1.82 (m, 2H), 1.45-1.43 (m, 2H), 1.31-1.27 (m, 2H), 1.18-1.15 (m, 4H), 1.05-1.01 (m, 2H); MS (ESI) m/z 457.5 (M$^+$+H).

EXAMPLE 25

Synthesis of Compound 1734

Step 1: Synthesis of tert-butyl 4-((4-fluorophenyl)(phenyl)amino)piperidine-1-carboxylate (Formula 6-3)

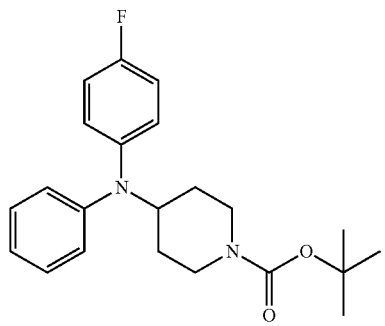

(6-3)

Tert-butyl 4-(phenylamino)piperidine-1-carboxylate (0.820 g, 2.967 mmol), 1-fluoro-4-iodobenzene (0.358 mL, 3.115 mmol), palladium acetate (II, 0.027 g, 0.119 mmol), 2,2'-bis(diphenylphosphino)-1,1'-binaphthayl (0.083 g, 0.134 mmol) and potassium tert-butoxide (0.416 g, 3.709 mmol) were dissolved in toluene (5 mL) at 110° C., and the solution was stirred at the same temperature for 16 hours, and then cooled to room temperature to terminate the reaction. The reaction mixture was filtered through a celite pad to remove solids, and water was added to the filtrate, followed by extraction with ethyl acetate. The organic layer was washed with a saturated aqueous solution of sodium chloride, dried with anhydrous magnesium sulfate, filtered, and then concentrated under reduced pressure. The concentrate was purified by column chromatography (SiO$_2$, 12 g cartridge; ethyl acetate/hexane=from 0% to 10%) and concentrated to afford the desired compound of formula 6-3 (0.352 g, 32.0%) as a bright yellow solid.

Step 2: Synthesis of N-(4-fluorophenyl)-N-phenylpiperidine-4-amine hydrochloride (Formula 6-4)

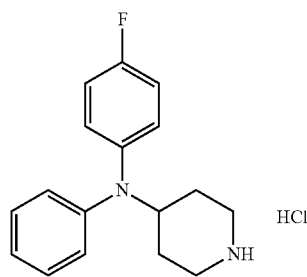

(6-4)

The compound of formula 6-3 (0.340 g, 0.918 mmol) prepared in step 1 and hydrochloric acid (4.00 M solution, 1.147 mL, 4.589 mmol) were dissolved in methylene chloride (5 mL) at room temperature, and the solution was stirred at the same temperature for 18 hours. The reaction mixture was concentrated under reduced pressure to remove the solvent. The product (0.281 g, 99.8%, yellow solid) was used without additional purification.

Step 3: Synthesis of methyl 7-(4-((4-fluorophenyl)(phenyl)amino)piperidine-1-carboxamido)heptanoate (Formula 6-6)

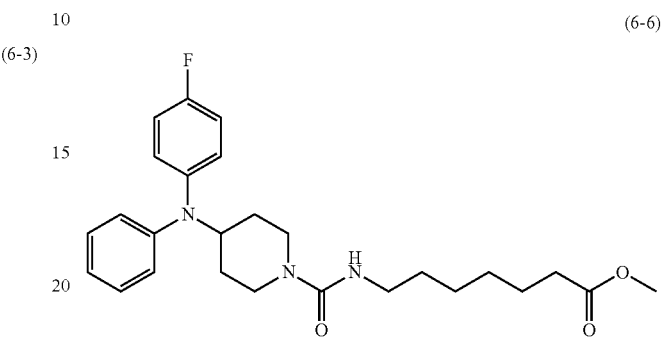

(6-6)

Methyl 7-aminoheptanoate hydrochloride (0.179 g, 0.913 mmol) and triphosgene (0.135 g, 0.456 mmol) were dissolved in methylene chloride (10 mL) at 0° C., and N,N-diisopropylethylamine (0.477 mL, 2.738 mmol) was added to the solution, followed by stirring at the same temperature. To the reaction mixture, the compound of formula 6-4 (0.280 g, 0.913 mmol) prepared in step 2 was added, followed by stirring at room temperature for 3 hours. Then, a saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; ethyl acetate/hexane=from 0% to 50%) and concentrated to afford the desired compound of formula 6-6 (0.185 g, 44.5%) as a colorless oil.

Step 4: Synthesis of 4-((4-fluorophenyl)(phenyl)amino)-N-(7-(hydroxyamino)-7-oxoheptyl)piperidine-1-carboxamide (Compound 1734)

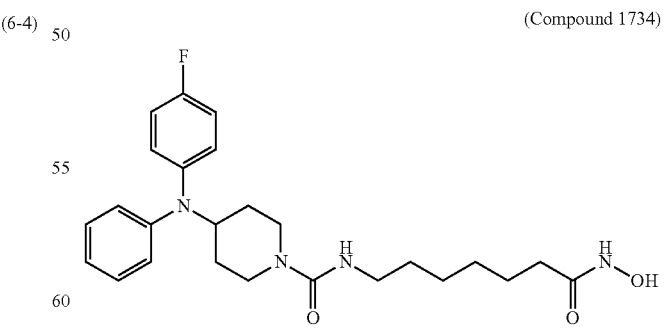

(Compound 1734)

The compound of formula 6-6 (0.260 g, 0.569 mmol) prepared in step 3 and hydroxylamine (50.00% aqueous solution, 0.348 mL, 5.695 mmol) were dissolved in methanol (5 mL) at 0° C., and the solution was stirred at room temperature for 3 hours. The reaction mixture was concentrated under reduced pressure to remove the solvent, and the precipitated solid was filtered, washed with hexane and dried to afford the desired compound 1734 (0.185 g, 71.2%) as a white solid.

$^1$H NMR (400 MHz, DMSO-$d_6$) δ 10.33 (s, 1H), 8.66 (s, 1H), 7.21-7.16 (m, 4H), 6.97-6.93 (m, 2H), 6.84-6.80 (m, 1H), 6.67-6.65 (m, 2H), 6.36-6.34 (m, 1H), 4.07-4.02 (m, 1H), 3.98-3.95 (m, 2H), 2.93-2.88 (m, 2H), 2.81-2.75 (m, 2H), 1.93-1.89 (m, 2H), 1.85-1.82 (m, 2H), 1.45-1.43 (m, 2H), 1.31-1.27 (m, 2H), 1.18-1.15 (m, 4H), 1.05-1.01 (m, 2H); MS (ESI) m/z 457.5 (M$^+$+H).

EXAMPLE 26

Synthesis of Compound 1763

Step 1: Synthesis of tert-butyl 7-benzhydryl-2,7-diazaspiro[3.5]nonane-2-carboxylate (Formula 4-5)

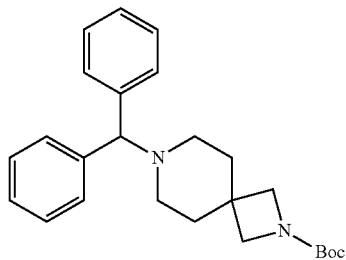

(4-5)

(Chloromethylene)dibenzene (0.439 mL, 2.467 mmol), tert-butyl 2,7-diazaspiro[3.5]nonane-2-carboxylate (0.614 g, 2.714 mmol) and potassium carbonate (1.705 g, 12.335 mmol) were dissolved in N,N-dimethylformamide (10 mL) at 80° C., and the solution was stirred at the same temperature for 16 hours, and then cooled to room temperature to terminate the reaction. A saturated aqueous solution of sodium bicarbonate was added to the reaction mixture, followed by extraction with ethyl acetate. The organic layer was washed with a saturated aqueous solution of sodium chloride, dried with anhydrous magnesium sulfate, filtered and then concentrated under reduced pressure. Then, ethyl acetate (100 mL) was added to the concentrate, followed by stirring, and the precipitated solid was filtered, washed with ethyl acetate and dried to afford the desired compound of formula 4-5 (0.411 g, 42.4%) as a white solid.

Step 2: Synthesis of 7-benzhydryl-2,7-diazaspiro[3.5]nonane hydrochloride (Formula 4-6)

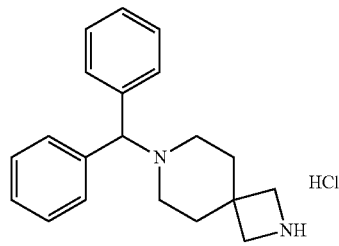

(4-6)

The compound of formula 4-5 (0.411 g, 1.047 mmol) prepared in step 1 was dissolved in methylene chloride (8 mL) at room temperature, and hydrochloric acid (4.00 M solution in dioxane, 1.309 mL, 5.235 mmol) was added to the solution, followed by stirring at the same temperature for 16 hours. The reaction mixture was concentrated under reduced pressure to remove the solvent, and the product (0.344 g, 99.9%, white solid) was used without additional purification.

Step 3: Synthesis of methyl 6-(7-benzhydryl-2,7-diazaspiro[3.5]nonane-2-carboxamido)hexanoate (Formula 4-7)

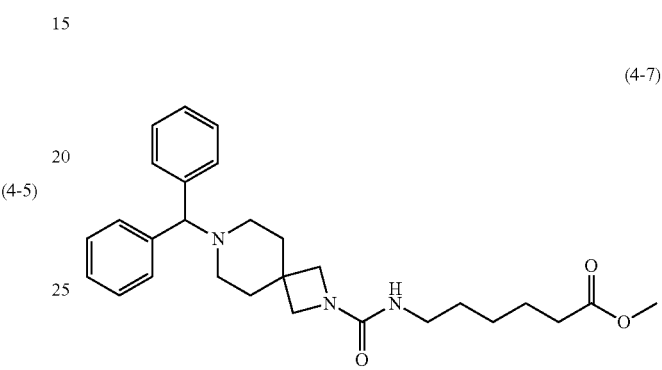

(4-7)

Methyl 6-aminohexanoate hydrochloride (0.100 g, 0.549 mmol) and triphosgene (0.078 g, 0.261 mmol) were dissolved in methylene chloride (5 mL) at 0° C., and N,N-diisopropylethylamine (0.273 mL, 1.569 mmol) was added to the solution, followed by stirring at the same temperature. To the reaction mixture, the compound of formula 4-6 (0.172 g, 0.523 mmol) prepared in step 2 was added, followed by stirring at room temperature for 3 hours. Then, a saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 3%) and concentrated to afford the desired compound of formula 4-7 (0.148 g, 61.0%) as a bright red solid.

Step 4: Synthesis of 7-benzhydryl-N-(6-(hydroxyamino)-6-oxohexyl)-2,7-diazaspiro[3.5]nonane-2-carboxamide (Compound 1763)

(Compound 1763)

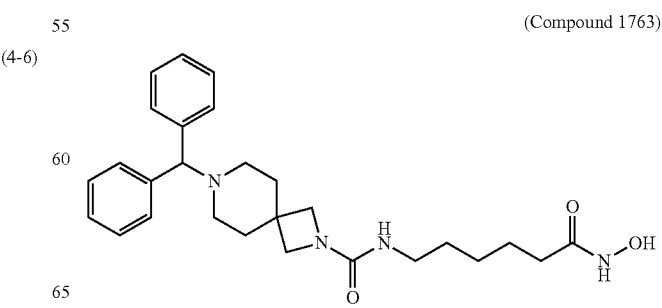

The compound of formula 4-7 (0.148 g, 0.319 mmol) prepared in step 3 and hydroxylamine (50.00% aqueous solution, 0.195 mL, 3.192 mmol) was dissolved in methanol (5 mL) at room temperature, and the solution was stirred at the same temperature for 3 hours. The reaction mixture was concentrated under reduced pressure to remove the solvent, and methanol (1 mL) and a saturated aqueous solution of sodium bicarbonate (30 mL) were added to the concentrate, followed by stirring. The precipitated solid was filtered, washed with hexane and dried, and the resulting material was recrystallized from ethyl acetate (10 mL) at 25° C. and filtered. The obtained solid was washed with hexane and dried to afford the desired compound 1763 (0.044 g, 29.7%) as a white solid.

$^1$H NMR (400 MHz, DMSO-$d_6$) δ 7.40-7.38 (m, 4H), 7.29-7.25 (m, 4H), 7.18-7.14 (m, 2H), 6.18-6.17 (m, 1H), 4.26 (s, 1H), 3.42-3.33 (m, 4H), 2.91-2.90 (m, 2H), 2.20-2.19 (m, 4H), 1.85-1.82 (m, 2H), 1.65-1.64 (m, 4H), 1.43-1.40 (m, 2H), 1.33-1.30 (m, 2H), 1.19-1.15 (m, 2H); MS (ESI) m/z 465.3 (M$^+$+H).

EXAMPLE 27

Synthesis of Compound 1764

Step 1: Synthesis of methyl 7-(7-benzhydryl-2,7-diazaspiro[3.5]nonane-2-carboxamido)heptanoate (Formula 4-7)

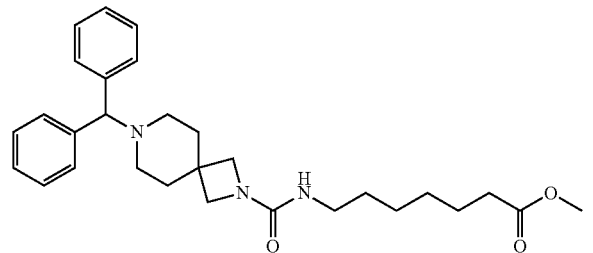

(4-7)

Methyl 7-aminoheptanoate hydrochloride (0.107 g, 0.549 mmol) and triphosgene (0.078 g, 0.261 mmol) were dissolved in methylene chloride (5 mL) at 0° C., and N,N-diisopropylethylamine (0.273 mL, 1.569 mmol) was added to the solution, followed by stirring at the same temperature. To the reaction mixture, the compound of formula 4-6 (0.172 g, 0.523 mmol) prepared in step 2 of Example 26 was added, followed by stirring at room temperature for 3 hours. Then, a saturated aqueous solution of sodium bicarbonate was added to the reaction mixture, followed by extraction with methylene chloride. The organic layer was washed with a saturated aqueous solution of sodium chloride, dried with anhydrous magnesium sulfate, filtered, and then concentrated under reduced pressure. The concentrate was purified by column chromatography (SiO$_2$, 4 g cartridge; methanol/methylene chloride=from 0% to 3%) and concentrated to afford the desired compound of formula 4-7 (0.136 g, 54.4%) as a bright red solid.

Step 2: Synthesis of 7-benzhydryl-N-(7-(hydroxyamino)-7-oxoheptyl)-2,7-diazaspiro[3.5]nonane-2-carboxamide (Compound 1764)

(Compound 1764)

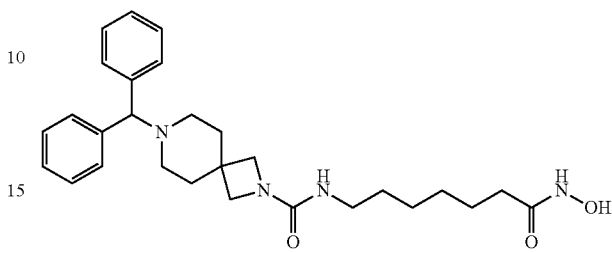

The compound of formula 4-7 (0.136 g, 0.285 mmol) prepared in step 1 and hydroxylamine (50.00%, 0.188 g, 2.847 mmol) were dissolved in methanol (5 mL) at room temperature, and the solution was stirred at the same temperature for 3 hours. The reaction mixture was concentrated under reduced pressure to remove the solvent, and methanol (1 mL) and a saturated aqueous solution of sodium bicarbonate (30 mL) were added to the concentrate, followed by stirring. The precipitated solid was filtered, washed with hexane and dried, and the resulting material was recrystallized from ethyl acetate (10 mL) at 25° C. and filtered. The obtained solid was washed with hexane and dried to afford the desired compound 1764 (0.021 g, 15.4%) as a white solid.

$^1$H NMR (400 MHz, DMSO-$d_6$) δ 7.40-7.38 (m, 4H), 7.29-7.25 (m, 4H), 7.18-7.14 (m, 2H), 6.16 (t, 1H, J=5.5 Hz), 4.26 (s, 1H), 3.42-3.41 (m, 4H), 2.92-2.88 (m, 2H), 2.19-2.18 (m, 4H), 1.88-1.84 (m, 2H), 1.65-1.64 (m, 4H), 1.43-1.42 (m, 2H), 1.32-1.31 (m, 2H), 1.19-1.18 (m, 4H); MS (ESI) m/z 479.6 (M$^+$+H).

Measurement of Activities of Compounds According to the Present Invention and Analytical Protocol

EXPERIMENTAL EXAMPLE 1

Confirmation (In Vitro) on Inhibition of HDAC Enzyme Activities

Because selective HDAC6 inhibitors are important for the selectivity of inhibition of HDAC1 that causes side effects, HDAC1/6 enzyme selectivities and cell selectivities (HDAC1: histone acetylation; HDAC6: tubulin acetylation) were analyzed.

1. Experimental Method

Using a HDAC1 fluorimetric drug discovery assay kit (Enzolifesciences: BML-AK511) and a HDAC6 human recombinant (Calbiochem: 382180), the HDAC enzyme inhibitory abilities of test compounds were measured. It was treated with 100, 1000 and 10000 nM concentrations for HDAC1 assay, and 0.1, 1, 10, 100 and 1000 nM concentrations for HDAC6 assay. It was allowed to react at 37° C. for 60 minutes, and then was treated with a developer and allowed to react at 37° C. for 30 minutes, after which the fluorescence intensity (Ex 390 nm; Em 460 nm) was measured using FlexStatin3 (Molecular Device).

2. Experimental Results
The results of the experiment are shown in Table 4 below.

TABLE 4

Abilities to inhibit the activities of HDAC enzymes (HDAC 1 and 6)

| Compound | HDAC6 (μM) | HDAC1 (μM) |
|---|---|---|
| ACY-1215 | 0.010 | 0.48 |
| 1102 | 0.004 | 3.84 |
| 1124 | 0.024 | 4.09 |
| 1188 | 0.014 | 1.68 |
| 1189 | 0.025 | 0.84 |
| 1190 | 0.065 | 1.34 |
| 1209 | 0.006 | 1.16 |
| 1210 | 0.07 | 1.19 |
| 1213 | 0.044 | 0.704 |
| 1221 | 0.079 | 1.88 |
| 1222 | 0.085 | 0.71 |
| 1223 | 0.073 | 1.16 |
| 1224 | 0.087 | 3.96 |
| 1240 | 0.07 | 0.41 |
| 1241 | 0.025 | 0.72 |
| 1243 | 0.017 | 0.54 |
| 1256 | 0.038 | 0.08 |
| 1257 | 0.063 | 0.159 |
| 1316 | 0.456 | 0.236 |
| 1317 | 0.336 | 0.023 |
| 1647 | 0.019 | 0.466 |
| 1648 | 0.029 | 0.729 |
| 1649 | 0.033 | 0.463 |
| 1719 | 0.116 | 1.729 |
| 1726 | 0.228 | 3.699 |
| 1734 | 0.094 | 0.886 |
| 1763 | 0.201 | 0.023 |
| 1764 | 0.04 | 0.236 |

As shown in Table 4 above, the control compound ACY-1215 showed 48-fold selectivity (0.01 μM for HDAC6, and 0.48 μM for HDAC1), compound 1102 showed 960-fold selectivity (0.004 μM for HDAC6, and 3.84 μM for HDAC1), compound 1124 showed 170-fold selectivity (0.024 μM for HDAC6, and 4.09 μM for HDAC1), and compound 1209 showed 193-fold selectivity (0.006 μM for HDAC6, and 1.16 μM for HDAC1), suggesting that the novel derivatives of the present invention show excellent selectivity for HDAC1/6 enzymes.

EXPERIMENTAL EXAMPLE 2

Effect of Compound 1102 in Adjuvant-Induced Arthritis Models

1. Experimental Method
100 μM of complete Freund's adjuvant (Chondrex) was injected intradermally into the tail of each Lewis rat to induce animal models. From one day before induction, the rats were divided into groups based on body weight, and the test compound was administered orally to the rats at various doses once a day, followed by evaluation.
Clinical score and body weight were measured twice a week from the day of first administration of the test compound. The clinical score was recorded as 0-4 points, and the total clinical score was evaluated after observing the foot of each rat (0: normal; and 16: the most severe edema).
2. Experimental Results
The results of the experiment are shown in FIG. 1. The medicinal effect of the test compound in the arthritis models was evaluated based on the degree of joint edema, and a higher clinical score indicates a more severe degree of edema.

As shown in FIG. 1, the group not treated with the compound (vehicle) showed a score of 9-11 (severe edema), whereas the group administered with 1 mg/kg of compound 1102 showed a score of 6-8, the group administered with 10 mg/kg of compound 1102 showed a score of 4-6, and the group administered with 50 mg/kg of compound 1102 showed a score of 1-3, indicating that compound 1102 of the present invention alleviates arthritis symptoms.

INDUSTRIAL APPLICABILITY

The compounds represented by formula I according to the present invention, optical isomers thereof or pharmaceutically acceptable salts thereof can selectively inhibit HDAC, and thus can be effectively used for the prevention or treatment of histone deacetylase-mediated diseases.

The invention claimed is:
1. A compound represented by the following formula I, an optical isomer thereof or a pharmaceutically acceptable salt thereof:

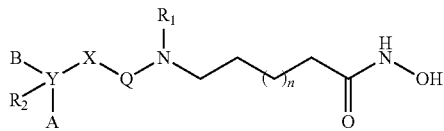

[Formula I]

wherein,
X is a heterocyclic alkyl selected from the group consisting of

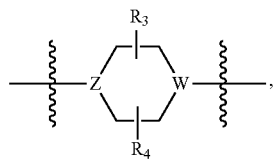

wherein when X is

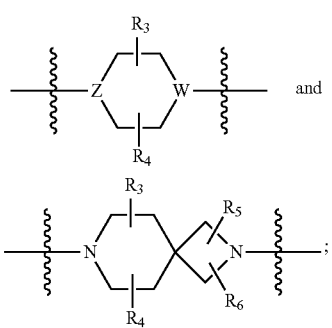

Z and W are each independently CH or N, at least one of Z and W is N, and $R_3$ and $R_4$ are each independently —H or —$C_1$-$C_4$ alkyl, wherein when X is

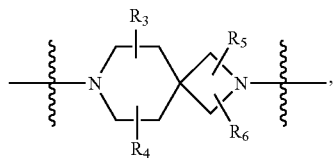

$R_3$, $R_4$, $R_5$, and $R_6$ are each independently —H or —$C_1$-$C_4$ alkyl;

Y is C or N;

each of A and B is independently —$C_1$-$C_4$ alkyl, —$C_6$-$C_{10}$ aryl, —$C_3$-$C_{12}$ heteroaryl, —$C_3$-$C_{10}$ cycloalkyl, —$C_2$-$C_{10}$ heterocycloalkyl, or —$C_3$-$C_{10}$ cycloalkenyl, wherein one or more hydrogen atoms of the —$C_1$-$C_4$ alkyl is optionally substituted with —OH or halogen, and each —$C_6$-$C_{10}$ aryl, —$C_3$-$C_{12}$ heteroaryl, —$C_3$-$C_{10}$ cycloalkyl, —$C_2$-$C_{10}$ heterocycloalkyl and —$C_3$-$C_{10}$ cycloalkenyl is independently optionally substituted with —OH, —$C_1$-$C_4$ alkyl, —$OC_1$-$C_4$ alkyl, —$CF_3$ or halogen;

Q is C=O or $SO_2$;

$R_1$ is —H or —$C_1$-$C_4$ alkyl;

$R_2$ is —H, —OH, —$C_1$-$C_4$ alkyl, —$C_1$-$C_4$ alkylhydroxy, halogen or null provided that when Y is C, $R_2$ is —H, —OH, —$C_1$-$C_4$ alkyl, —$C_1$-$C_4$ alkylhydroxy, or halogen and when Y is N, $R_2$ is null; and n is 1, 2, 3, or 4.

2. The compound represented by formula I, optical isomer thereof or pharmaceutically acceptable salt thereof according to claim 1, wherein X is a heterocyclic alkyl selected from the group consisting of

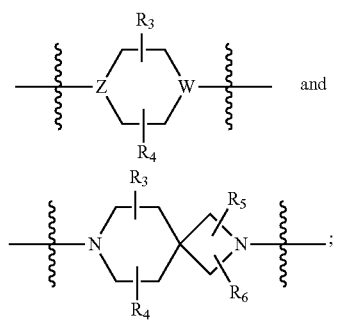

wherein when X is

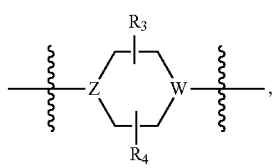

Z and W are each independently CH or N, at least one of Z and W is N, and $R_3$ and $R_4$ are each independently —H or —$C_1$-$C_4$ alkyl, wherein when X is

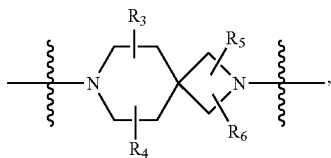

$R_3$, $R_4$, $R_5$ and $R_6$ are each independently —H or —$C_1$-$C_4$ alkyl;

Y is C or N;

each of A and B is independently —$C_1$-$C_4$ alkyl, —$C_6$-$C_{10}$ aryl, —$C_3$-$C_{12}$ heteroaryl, —$C_3$-$C_{10}$ cycloalkyl, —$C_2$-$C_{10}$ heterocycloalkyl, or —$C_3$-$C_{10}$ cycloalkenyl, wherein one or more hydrogen atoms of the —$C_1$-$C_4$ alkyl is optionally substituted with —OH or halogen, and each —$C_6$-$C_{10}$ and —$C_3$-$C_{12}$ heteroaryl is independently optionally substituted with —OH, —$C_1$-$C_4$ alkyl, —$OC_1$-$C_4$ alkyl, —$CF_3$ or halogen;

Q is C=O or $SO_2$;

$R_1$ is —H or —$C_1$-$C_4$ alkyl;

$R_2$ is —H, —OH, halogen or null, provided that when Y is C, $R_2$ is —H, —OH, or halogen, and when Y is N, $R_2$ is null; and n is 1, 2, 3, or 4.

3. The compound represented by formula I, optical isomer thereof or pharmaceutically acceptable salt thereof according to claim 2, wherein X is

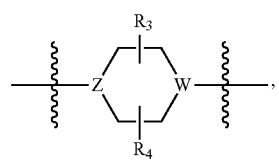

wherein each Z and W is independently CH or N, at least one of Z and W is N, and each of $R_3$ and $R_4$ is independently —H or $C_1$-$C_4$ alkyl;

Y is C or N;

each of A and B is independently —$C_1$-$C_4$ alkyl, —$C_6$-$C_{10}$ aryl or —$C_3$-$C_{12}$ heteroaryl, wherein one or more hydrogen atoms of the —$C_1$-$C_4$ alkyl is optionally substituted with —OH or halogen, and each $C_6$-$C_{10}$ aryl and $C_3$-$C_{12}$ heteroaryl is independently optionally substituted with —OH, —$C_1$-$C_4$ alkyl, —$OC_1$-$C_4$ alkyl, —$CF_3$ or halogen;

Q is C=O;

$R_1$ is —H or —$C_1$-$C_4$ alkyl;

$R_2$ is —H, —OH, halogen or null provided that when Y is C, $R_2$ is —H, —OH or halogen, and when Y is N, $R_2$ is null; and n is 3.

4. The compound represented by formula I, optical isomer thereof or pharmaceutically acceptable salt thereof according to claim 1, wherein the compound represented by formula I is selected from the group consisting of compounds described in the following table:

| Compound | Structure |
|---|---|
| 1102 | 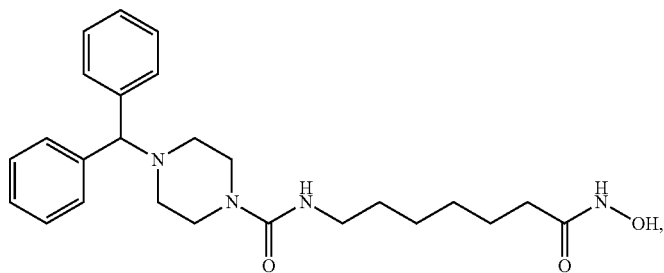 [SMILES: O=C(CCCCCCNC(=O)N1CCN(C(c2ccccc2)c2ccccc2)CC1)NO] |
| 1124 | 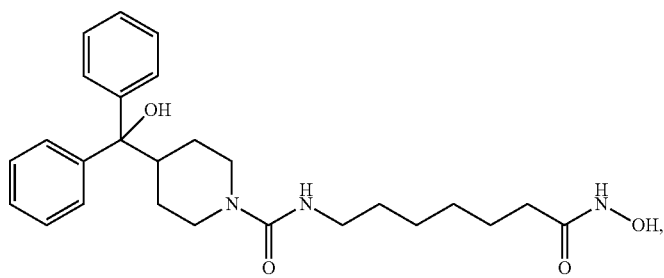 [SMILES: O=C(CCCCCCNC(=O)N1CCC(C(O)(c2ccccc2)c2ccccc2)CC1)NO] |
| 1188 | 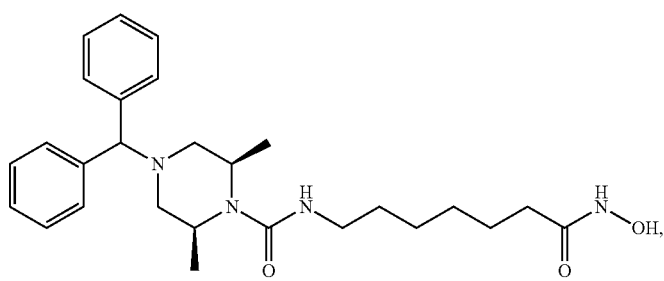 [SMILES: C[C@@H]1CN(C(c2ccccc2)c2ccccc2)C[C@H](C)N1C(=O)NCCCCCCC(=O)NO] |
| 1189 | 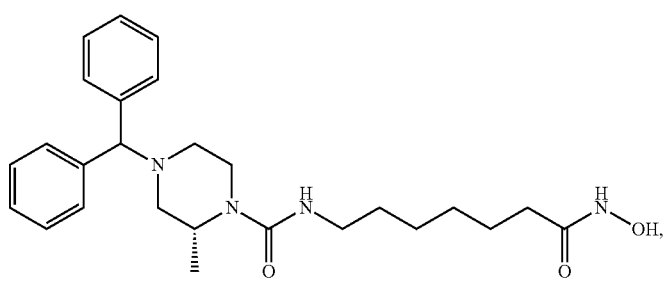 [SMILES: C[C@@H]1CN(C(c2ccccc2)c2ccccc2)CCN1C(=O)NCCCCCCC(=O)NO] |
| 1190 | 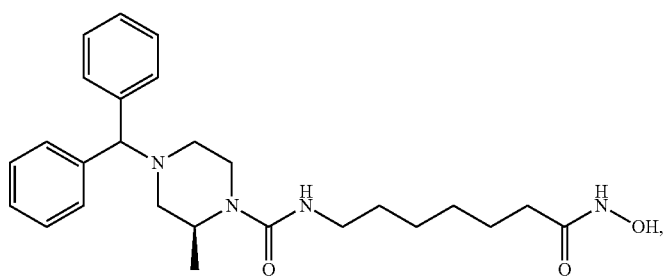 [SMILES: C[C@H]1CN(C(c2ccccc2)c2ccccc2)CCN1C(=O)NCCCCCCC(=O)NO] |

| Compound | Structure |
|---|---|
| 1209 | 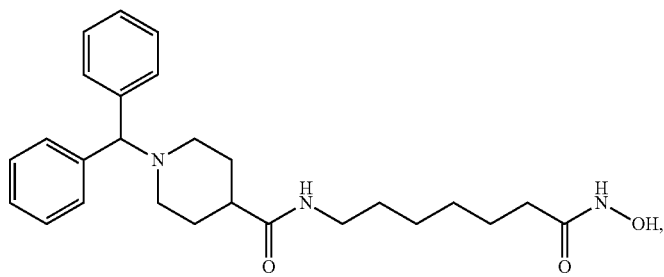 |
| 1210 | 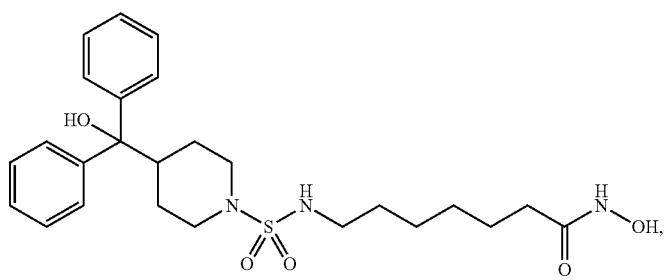 [SMILES: O=C(CCCCCCNS(=O)(=O)N1CCC(C(O)(c2ccccc2)c2ccccc2)CC1)NO] |
| 1213 | 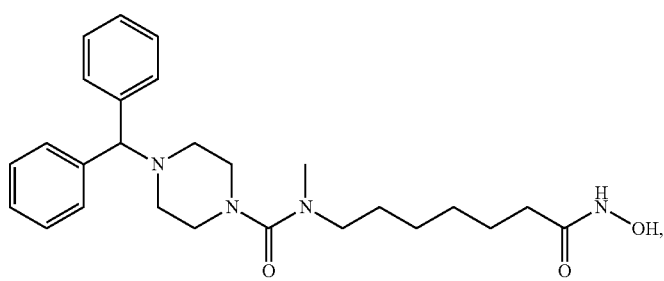 [SMILES: CN(CCCCCCC(=O)NO)C(=O)N1CCN(C(c2ccccc2)c2ccccc2)CC1] |
| 1221 | 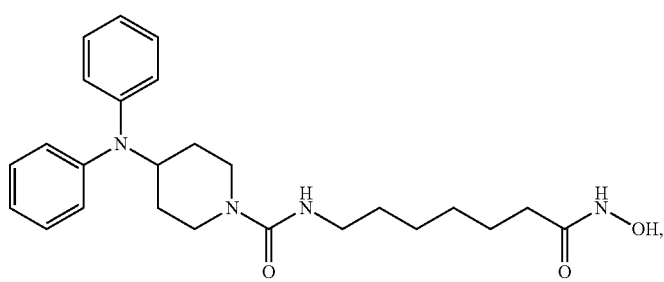 [SMILES: O=C(CCCCCCNC(=O)N1CCC(N(c2ccccc2)c2ccccc2)CC1)NO] |
| 1222 | 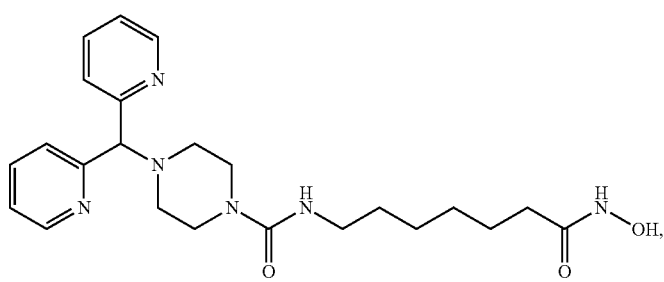 [SMILES: O=C(CCCCCCNC(=O)N1CCN(C(c2ccccn2)c2ccccn2)CC1)NO] |

| Compound | Structure |
|---|---|
| 1223 | 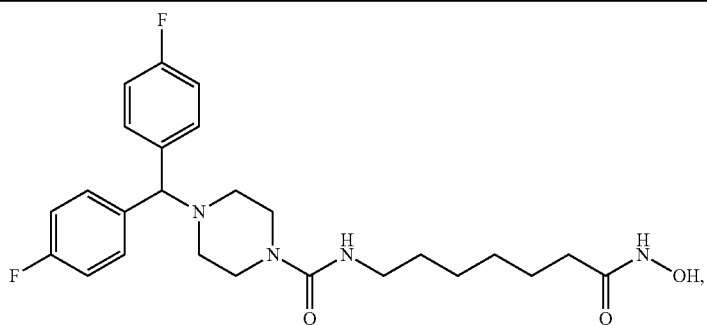 |
| 1224 | 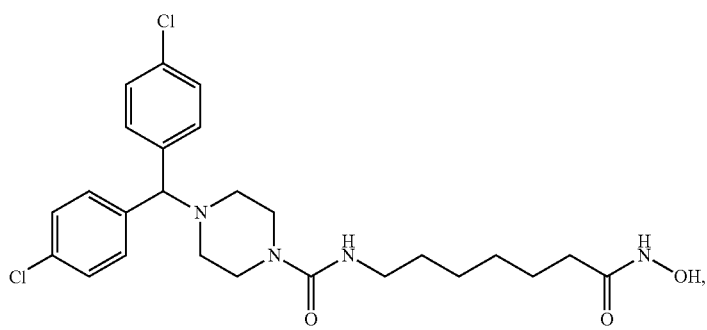 [SMILES: O=C(CCCCCCNC(=O)N1CCN(C(c2ccc(F)cc2)c2ccc(F)cc2)CC1)NO] |
| 1240 | 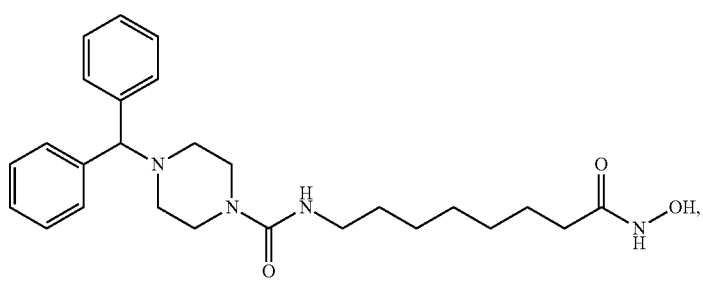 |
| 1241 | 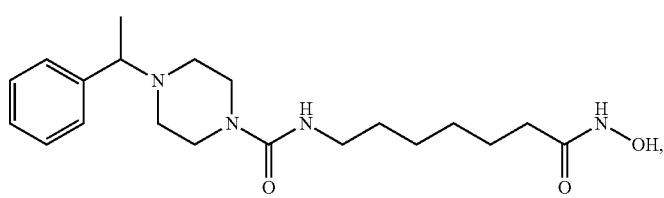 [SMILES: CC(c1ccccc1)N1CCN(C(=O)NCCCCCCC(=O)NO)CC1] |
| 1243 | 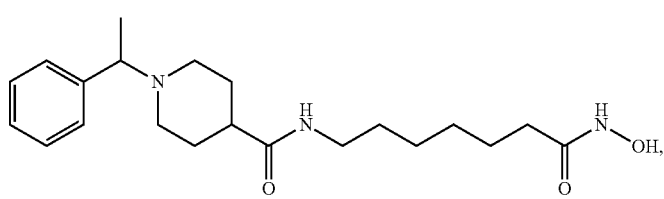 [SMILES: CC(c1ccccc1)N1CCC(C(=O)NCCCCCCC(=O)NO)CC1] |
| 1256 | 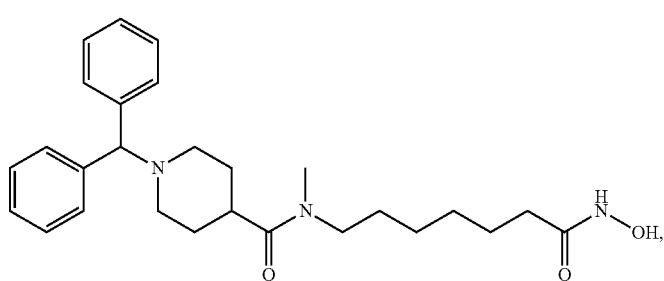 [SMILES: CN(CCCCCCC(=O)NO)C(=O)C1CCN(C(c2ccccc2)c2ccccc2)CC1] |

-continued
| Compound | Structure |
|---|---|
| 1257 | 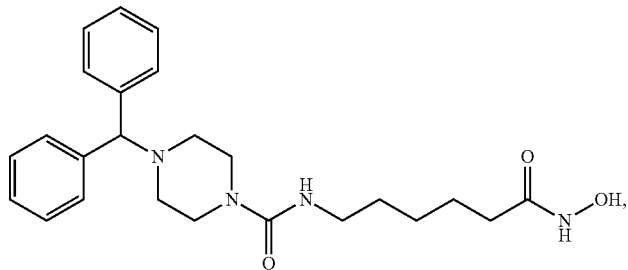 [SMILES: O=C(CCCCCNC(=O)N1CCN(C(c2ccccc2)c2ccccc2)CC1)NO] |
| 1316 | 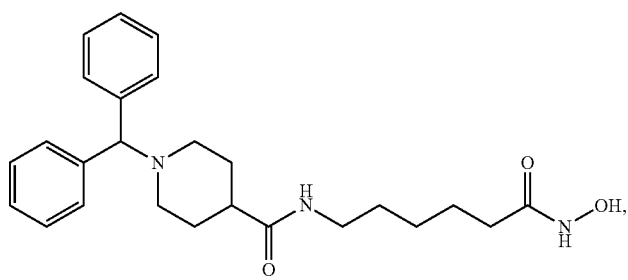 [SMILES: O=C(CCCCCNC(=O)C1CCN(C(c2ccccc2)c2ccccc2)CC1)NO] |
| 1317 | 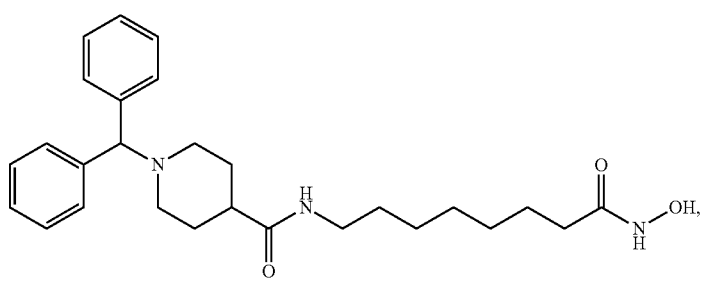 [SMILES: O=C(CCCCCCCNC(=O)C1CCN(C(c2ccccc2)c2ccccc2)CC1)NO] |
| 1647 | 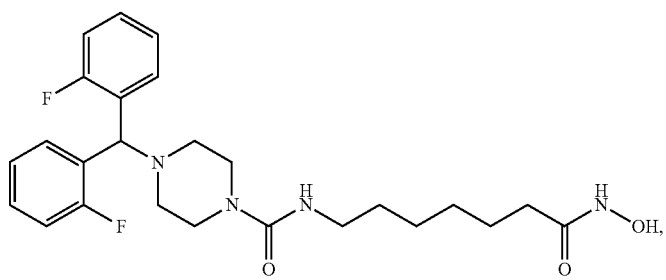 [SMILES: O=C(CCCCCCNC(=O)N1CCN(C(c2ccccc2F)c2ccccc2F)CC1)NO] |
| 1648 | 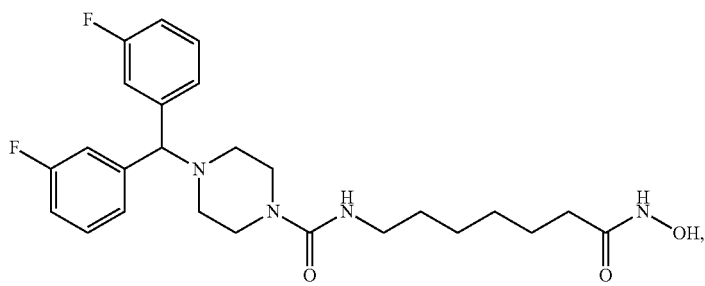 [SMILES: O=C(CCCCCCNC(=O)N1CCN(C(c2cccc(F)c2)c2cccc(F)c2)CC1)NO] |

-continued
| Compound | Structure |
|---|---|
| 1649 | 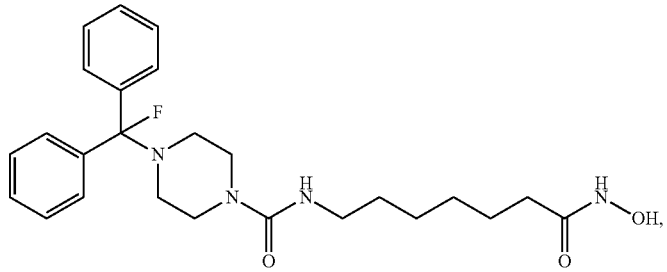 [SMILES: O=C(CCCCCCNC(=O)N1CCN(C(F)(c2ccccc2)c2ccccc2)CC1)NO] |
| 1719 | 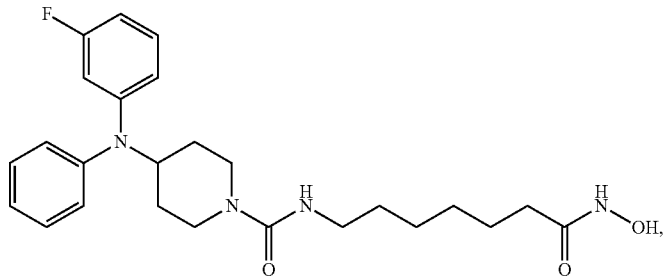 [SMILES: O=C(CCCCCCNC(=O)N1CCC(N(c2ccccc2)c2cccc(F)c2)CC1)NO] |
| 1726 | 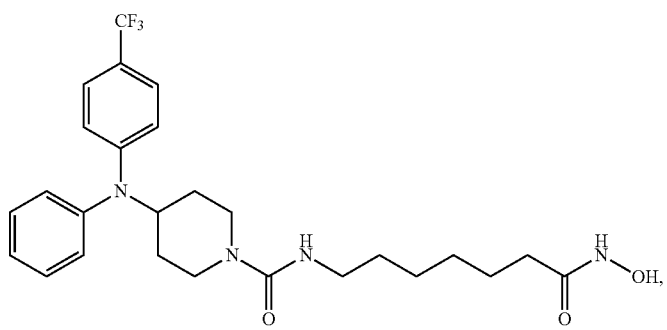 [SMILES: O=C(CCCCCCNC(=O)N1CCC(N(c2ccccc2)c2ccc(C(F)(F)F)cc2)CC1)NO] |
| 1734 | 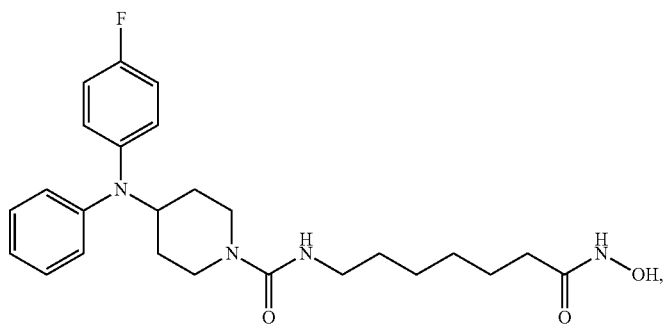 [SMILES: O=C(CCCCCCNC(=O)N1CCC(N(c2ccccc2)c2ccc(F)cc2)CC1)NO] |
| 1763 | 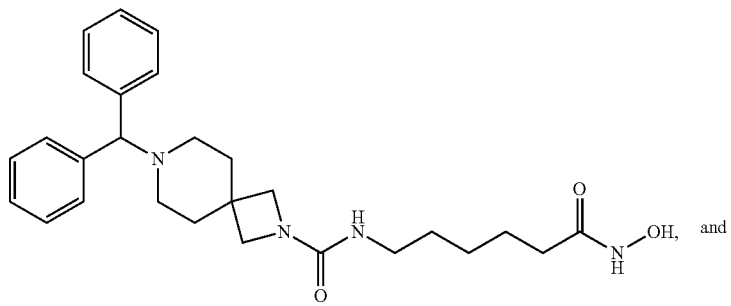 [SMILES: O=C(CCCCCNC(=O)N1CC2(CCN(C(c3ccccc3)c3ccccc3)CC2)C1)NO] and |

| Compound | Structure |
|---|---|
| 1764 | 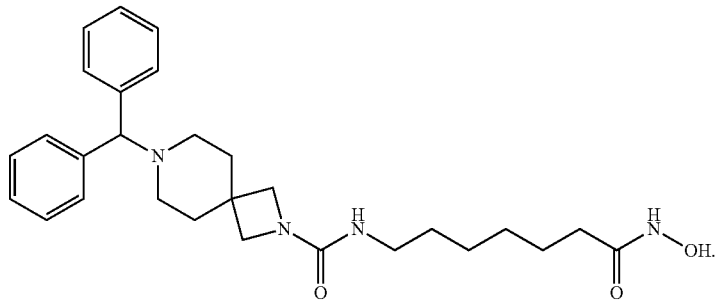 [SMILES: O=C(CCCCCCNC(=O)N1CC2(CCN(C(c3ccccc3)c3ccccc3)CC2)C1)NO] |
5. The compound represented by formula I, optical isomer thereof or pharmaceutically acceptable salt thereof according to claim 4, wherein the compound represented by formula I is selected from the group consisting of compounds described in the following table:
| Compound | Structure |
|---|---|
| 1102 | 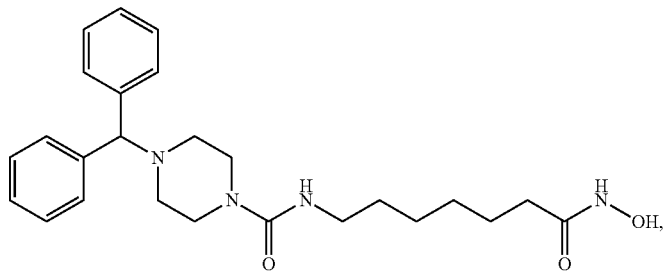 [SMILES: O=C(CCCCCCNC(=O)N1CCN(C(c2ccccc2)c2ccccc2)CC1)NO] |
| 1124 | 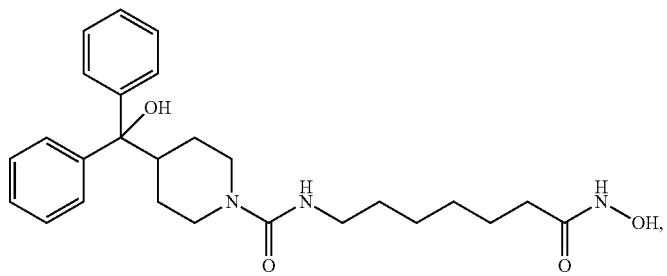 [SMILES: O=C(CCCCCCNC(=O)N1CCC(C(O)(c2ccccc2)c2ccccc2)CC1)NO] |
| 1188 | 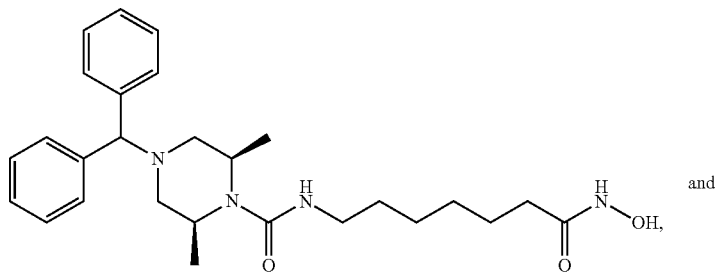 [SMILES: C[C@@H]1CN(C(c2ccccc2)c2ccccc2)C[C@H](C)N1C(=O)NCCCCCCC(=O)NO] and |

| Compound | Structure |
|---|---|
| 1209 | 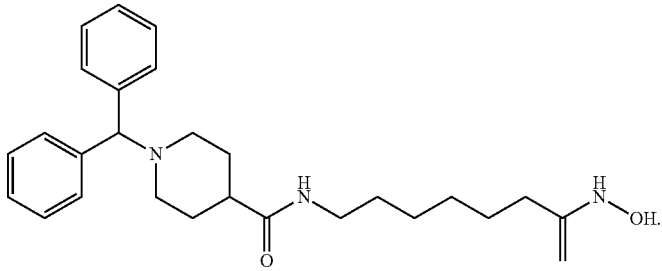 [SMILES: C=C(CCCCCCNC(=O)C1CCN(C(c2ccccc2)c2ccccc2)CC1)NO] |

6. A pharmaceutical composition for treating histone deacetylase-mediated disease, comprising, as an active ingredient, the compound represented by formula I, optical isomer thereof or pharmaceutically acceptable salt thereof according to claim 1, wherein the histone deacetylase-mediated disease is cell proliferative disease, inflammatory disease, autosomal dominant disease, genetic metabolic disease, autoimmune disease, acute/chronic neurological disease, hypertrophy, heart failure, ocular disease, or neurodegenerative disease.

* * * * *

UNITED STATES PATENT AND TRADEMARK OFFICE
CERTIFICATE OF CORRECTION

PATENT NO. : 11,420,950 B2  
APPLICATION NO. : 15/575672  
DATED : August 23, 2022  
INVENTOR(S) : Changsik Lee et al.

Page 1 of 1

It is certified that error appears in the above-identified patent and that said Letters Patent is hereby corrected as shown below:

In the Claims

Column 90, Claim 1, after the formula between Lines 40-45, delete "," and then insert --and

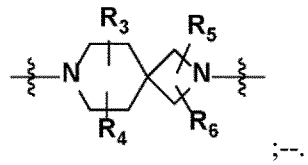

;--.

Column 90, Claim 1, after the formula between Lines 50-55, insert --,-- and then delete "and

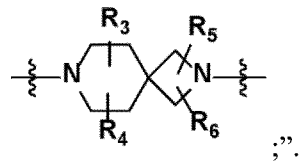

;".

Signed and Sealed this  
Seventeenth Day of January, 2023

Katherine Kelly Vidal  
*Director of the United States Patent and Trademark Office*